(12) United States Patent
Sabol et al.

(10) Patent No.: US 7,187,790 B2
(45) Date of Patent: Mar. 6, 2007

(54) DATA PROCESSING AND FEEDBACK METHOD AND SYSTEM

(75) Inventors: John M. Sabol, Sussex, WI (US); Gopal B. Avinash, New Berlin, WI (US); Matthew J. Walker, New Berlin, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 775 days.

(21) Appl. No.: 10/323,204

(22) Filed: Dec. 18, 2002

(65) Prior Publication Data

US 2004/0120557 A1    Jun. 24, 2004

(51) Int. Cl.
*G06K 9/00* (2006.01)
*G06K 9/68* (2006.01)

(52) U.S. Cl. .................. 382/128; 382/130; 382/218
(58) Field of Classification Search ............ 382/128, 382/130, 218
See application file for complete search history.

(56) References Cited

U.S. PATENT DOCUMENTS

| | | | |
|---|---|---|---|
| 5,019,976 A * | 5/1991 | Chiu et al. ............... 382/203 |
| 5,452,367 A * | 9/1995 | Bick et al. ............... 382/128 |
| 5,740,267 A * | 4/1998 | Echerer et al. ........... 382/132 |
| 6,011,862 A * | 1/2000 | Doi et al. ................ 382/132 |
| 6,058,322 A * | 5/2000 | Nishikawa et al. ....... 600/408 |
| 6,067,373 A * | 5/2000 | Ishida et al. ............. 382/130 |
| 6,628,743 B1 * | 9/2003 | Drummond et al. ......... 378/8 |
| 6,738,499 B1 * | 5/2004 | Doi et al. ................ 382/128 |
| 2003/0215120 A1 * | 11/2003 | Uppaluri et al. ......... 382/128 |
| 2005/0207630 A1 * | 9/2005 | Chan et al. ............. 382/131 |

* cited by examiner

*Primary Examiner*—Bhavesh M. Mehta
*Assistant Examiner*—Utpal Shah
(74) *Attorney, Agent, or Firm*—Fletcher Yoder

(57) ABSTRACT

A technique is provided for offering feedback, including feedback for patient care and for training purposes for medical professionals and human operators. The technique includes accessing data, such as image data, for evaluation by a human operator. The data is then analyzed via a computer-assisted data operating algorithm, and the analysis may further include analysis of supplemental data accessed from an integrated knowledge base. Based upon the analysis feedback is provided to the operator, such as for completing or complementing the evaluation, correcting analysis by the human operator, or otherwise informing the human operator of similarities or differences between the analyses.

25 Claims, 31 Drawing Sheets

| | TYPE | | | | |
|---|---|---|---|---|---|
| ELECTRICAL DATA | IMAGING DATA | CLINICAL LABORATORY DATA | HISTOLOGIC DATA | PHARMACO-KINETIC DATA | MISCELLANEOUS DATA |
| EEG | X-RAY | BLOOD | TISSUE ANALYSIS | THERAPEUTIC DRUG MONITORING | PHYSICAL EXAM |
| ECG | MR | URINE | CYTOLOGY | RECEPTOR CHARACTERIZATION AND MEASUREMENT | MEDICAL HISTORY |
| EMG | CT | SALIVA | TISSUE TYPING | COMBINATION | PSYCHIATRIC |
| EIT | PET | GASTROINTESTINAL FLUIDS | IMMUNO-CYTOCHEMISTRY | | PSYCHIATRIC HISTORY |
| NERVE CONDUCTION TESTS | FLUOROGRAPHY | REPRODUCTIVE FLUIDS | HISTO-PATHOLOGICAL ANALYSIS | | BEHAVIORAL PATTERNS |
| ENG | MAMMOGRAPHY | CEREBROSPINAL FLUID | ELECTRON MICROSCOPY | | BEHAVIORAL TESTING |
| | SONOGRAPHY | PCR | IS SITU HYBRIDATION | | DEMOGRAPHIC DATA |
| COMBINATION | INFRARED | GENE MARKERS | COMBINATION | | DRUG USE |
| | NUCLEAR | RADIOIMMUNO-ASSY, ELISA | | | FOOD INTAKE |
| | THERMO-ACOUSTIC | CHROMATOGRAPHY | | | ENVIRONMENTAL FACTORS |
| | COMB. | RECEPTOR ASSAYS | | | GROSS PATHOLOGY |
| | | COMBINATION | | | INFORMATION FROM NON-BIOLOGIC MODELS |
| | | | | | COMBINATION |

FIG. 8

DATA PROCESSING AND FEEDBACK METHOD AND SYSTEM

BACKGROUND OF THE INVENTION

The present invention relates generally to field of medical data processing, acquisition and analysis. More particularly, the invention relates to techniques for drawing upon a wide range of available medical data for informing decisions related to diagnosis, treatment, further data processing, acquisition and analysis.

In the medical field many different tools are available for learning about and treating patient conditions. Traditionally, physicians would physically examine patients and draw upon a vast array of personal knowledge gleaned from years of study to identify problems and conditions experienced by patients, and to determine appropriate treatments. Sources of support information traditionally included other practitioners, reference books and manuals, relatively straightforward examination results and analyses, and so forth. Over the past decades, and particularly in recent years, a wide array of further reference materials have become available to the practitioner that greatly expand the resources available and enhance and improve patient care.

Among the diagnostic resources currently available to physicians and other caretakers are databases of information as well as sources which can be prescribed and controlled. The databases, are somewhat to conventional reference libraries, are know available from many sources and provide physicians with detailed information on possible disease states, information on how to recognize such states, and treatment of the states within seconds. Similar reference materials are, of course, available that identify such considerations as drug interactions, predispositions for disease and medical events, and so forth. Certain of these reference materials are available at no cost to care providers, while other are typically associated with a subscription or community membership.

Specific data acquisition techniques are also known that can be prescribed and controlled to explore potential physical conditions and medical events, and to pinpoint sources of potential medical problems. Traditional prescribable data sources included simple blood tests, urine tests, manually recorded results of physical examinations, and the like. Over recent decades, more sophisticated techniques have been developed that include various types of electrical data acquisition which detect and record the operation of systems of the body and, to some extent, the response of such systems to situations and stimuli. Even more sophisticated systems have been developed that provide images of the body, including internal features which could only be viewed and analyzed through surgical intervention before their development, and which permit viewing and analysis of other features and functions which could not have been seen in any other manner. All of these techniques have added to the vast array of resources available to physicians, and have greatly improved the quality of medical care.

Despite the dramatic increase and improvement in the sources of medical-related information, the prescription and analysis of tests and data, and the diagnosis and treatment of medical events still relies to a great degree upon the expertise of trained care providers. Input and judgment offered by human experience will not and should not be replaced in such situations. However, further improvements and integration of the sources of medical information are needed. While attempts have been made at allowing informed diagnosis and analysis in a somewhat automated fashion, these attempts have not even approached the level of integration and correlation which would be most useful in speedy and efficient patient care.

Current methods of analyzing and integrating available data provide very little feedback to medical professional based upon their evaluation of data. In a medical imaging field, for example, it has become common for radiologist to access and view images electronically, even annotating the images via automated systems. However, automated techniques have not been extended or have been integrated into this process, such that feedback to the medical professions is extremely limited based upon data processing algorithms carried out on the same datasets as those used to reconstruct images. Even less integration has been provided in other types of environments, such as the analysis of in vitro test samples, patient records, and so forth. Such feedback could serve the purpose of improving patient care, as well as for training of medical professionals or further honing skills as new techniques and data become available. There is a need, therefore, for improved techniques designed to assist in providing feedback to human operators, particularly medical professionals, based upon computer-assisted analysis of available data.

The present invention provides novel techniques designed to respond to such needs. In accordance with a first aspect of the invention, a method is provided for performing an operation on data that includes steps of accessing data from a repository, the data including a feature of interest identifiable from the data, and receiving an assessment from a human operator regarding the feature of interest in the accessed data. Supplemental data is accessed including a known correct assessment of a similar feature of interest identifiable from the supplemental data. The accessed data, the received assessment, and the supplemental data are then analyzed via a computer-assisted data operating algorithm, and feedback is provided to the human operator based upon the analysis.

In accordance with a further aspect of the invention, a method is provided for processing medical data that includes accessing first image data from a repository, and reconstructing displaying a medical diagnostic image based upon the first image data. Data is then received from a human image reader regarding a reader feature of interest in the displayed image. Second image data is accessed that is derived from integrated knowledge base including data from a plurality of controllable and prescribable data resources. The first and second image data are analyzed via a computer-assisted data operating algorithm to generate a result dataset identifying a computer feature of interest in the image data. The result dataset is then compared to the data from the human image reader, and feedback is provided to the human image reader based upon the analysis.

In accordance with a further aspect of the invention, systems and computer programs are provided for carrying out similar functions.

The present invention provides novel techniques for handling of medical data designed to provide such enhanced care. The techniques may draw upon the full range of available medical data, which may be considered to be included in an integrated knowledge base. The integrated knowledge base, itself, may be analytically subdivided into certain data resources and other controllable and prescribable resources. The data resources may include such things as databases which are patient-specific, population-specific, condition-specific, or that group any number of factors, including physical factors, genetic factors, financial and economic factors, and so forth. The controllable and prescribable resources may include any available medical data acquisition systems, such as electrical systems, imaging systems, systems based upon human and machine analyses of patients and tissues, and so forth. Based upon such data, routines executed by one or a network of computer systems, defining a general processing system, can identify and diagnose potential medical events. Moreover, the processing system may prescribe additional data acquisition from the controllable and prescribable resources, including additional or different types of data during a single time period, or the same or different types of data over extended periods of time.

The analyses of the medical data available to the logic engine may be employed for a number of purposes, first and foremost for the diagnosis and treatment of medical events. Thus, patient care can be improved by more rapid and informed identification of disease states, medical conditions, predispositions for future conditions and events, and so forth. Moreover, the system allows for more rapid, informed, targeted and efficient data acquisition, based upon such factors as the medical events or conditions which are apt to be of greatest priority or importance. The system enables other uses, however. For example, based upon knowledge programmed or gained over time, the system provides useful training tools for honing the skills of practitioners. Similarly, the system offers great facility in providing high-quality medical care in areas or in situations where the most knowledgeable care provider and most appropriate information gathering systems may simply be unavailable.

In short, it is believed that the present techniques provide the highest level of integration of both data resources, and prescribable and controllable resources currently possible in the field. This system may be implemented in a more limited fashion, such as to integrate only certain types of resources or for the purposes of data acquisition and analysis alone. However, even in such situations, the system may be further expanded by the inclusion of software, firmware or hardware modules, or by the coupling of additional or different data sources along with their correlation to other data sources in the analyses performed by the processing system. The resulting system, in conjunction with existing and even future sources of medical data, provides a compliment and an extremely useful linking tool for the experienced practitioner, as well as for the less experienced clinician in identifying and treating medical events and conditions. This system may be further employed for targeting very specific conditions and events as desired.

BRIEF DESCRIPTION OF THE INVENTION

The foregoing and other advantages and features of the invention will become apparent upon reading the following detailed description and upon reference to the drawings in which:

FIG. 8 is a tabulated representation of a range of exemplary prescribable and controllable medical data resources organized by type and illustrating the various modalities of resources within the types;

DETAILED DESCRIPTION OF SPECIFIC EMBODIMENTS

Figure 1:
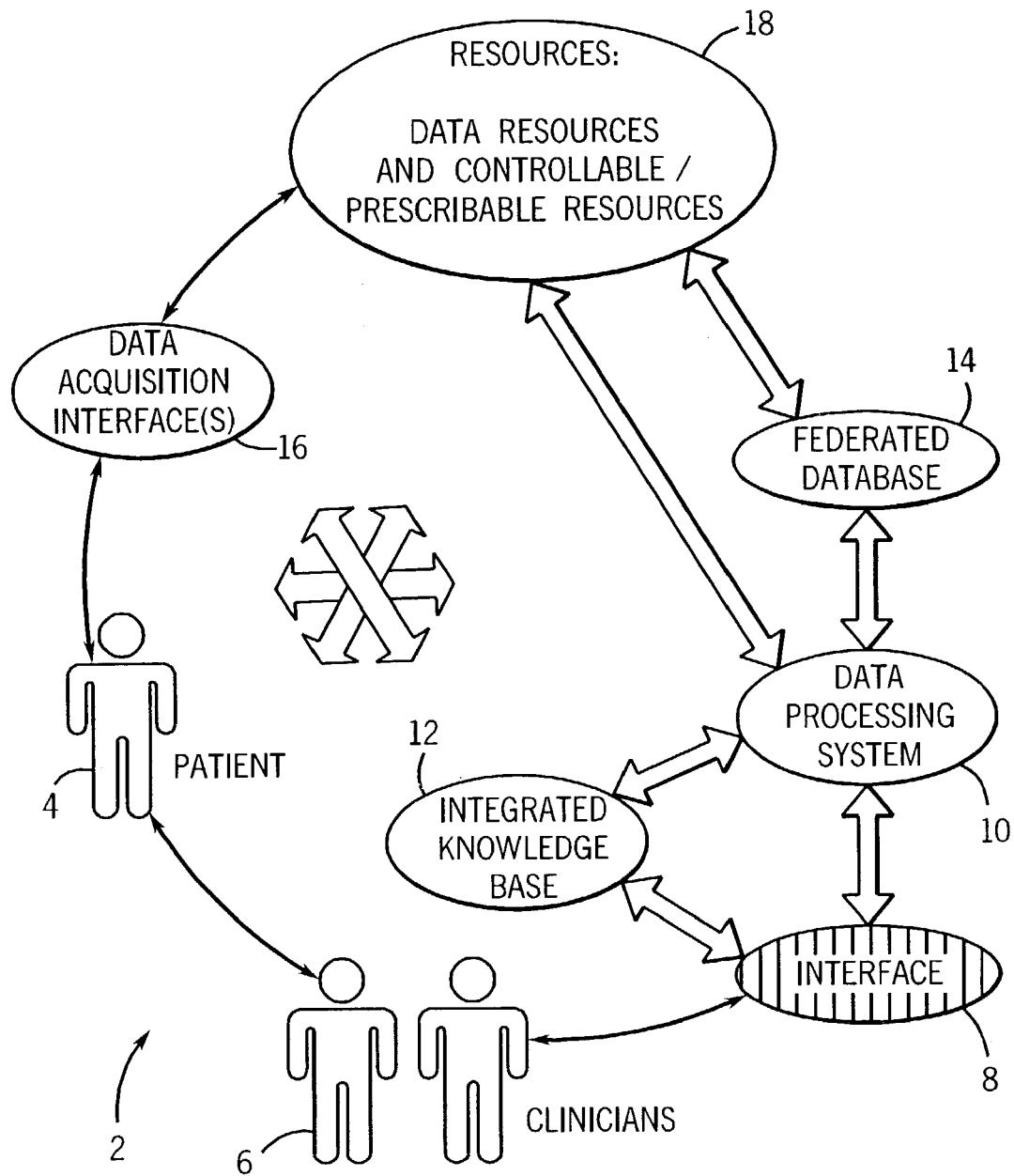
FIG. 1 is a general overview certain exemplary functional components within a computer-aided medical data handling system and of data flow between the components in accordance with aspects of the present techniques.

Turning now to the drawings, and referring first to FIG. 1, an overview of a computer aided medical data exchange system 2 is illustrated. The system 2 is designed to provide high-quality medical care to a patient 4 by facilitating the management of data available to care providers, as indicated at reference numeral 6 in FIG. 1. The care providers will typically include attending physicians, radiologist, surgeons, nurses, clinicians, various specialists, and so forth. It should be noted, however, that while general reference is made to a clinician in the present context, the care providers may also include clerical staff, insurance companies, teachers and students, and so forth.

The system illustrated in FIG. 1 provides an interface 8 which allows the clinicians to exchange data with a data processing system 10. More will be said regarding the types of information which can be exchanged between the system and the clinicians, as well as about the interfaces and data processing system, and their functions. The data processing system 10 is linked to an integrated knowledge base 12 and a federated database 14, as illustrated in FIG. 1. System 10, and the federated database 14 draw upon data from a range of data resources, as designated generally by reference numeral 18. The federated database 14 may be software-based, and includes data access tools for drawing information from the various resources as described below, or coordinating or translating the access of such information. In general, the federated database will unify raw data into a useable form. Any suitable form may be employed, and multiple forms may be employed, where desired, including hypertext markup language (HTML) extended markup language (XML), Digital Imaging and Communications in Medicine (DICOM), Health Level Seven® (HL7), and so forth. In the present context, the integrated knowledge base 12 is considered to include any and all types of available medical data which can be processed by the data processing system and made available to the clinicians for providing the desired medical care. In the simplest implementation, the resources 18 may include a single source of medical data, such as an imaging system, or more conventional data extraction techniques (e.g. forms completed by a patient or care provider). However, the resources may include many more and varied types of data as described more fully below. In general, data within the resources and knowledge base are digitized and stored to make the data available for extraction and analysis by the federated database and the data processing system. Thus, even where more conventional data gathering resources are employed, the data is placed in a form which permits it to be identified and manipulated in the various types of analyses performed by the data processing system.

As used herein, the term "integrated knowledge base" is intended to include one or more repositories of medical-related data in a broad sense, as well as interfaces and translators between the repositories, and processing capabilities for carrying out desired operations on the data, including analysis, diagnosis, reporting, display and other functions. The data itself may relate to patient-specific characteristics as well as to non-patient specific information, as for classes of persons, machines, systems and so forth. Moreover, the repositories may include devoted systems for storing the data, or memory devices that are part of disparate systems, such as imaging systems. As noted above, the repositories and processing resources making up the integrated knowledge base may be expandable and may be physically resident at any number of locations, typically linked by dedicated or open network links. Furthermore, the data contained in the integrated knowledge base may include both clinical data (i.e. data relating specifically to a patient condition) and non-clinical data. Non-clinical data may include data representative of financial resources, physical resources (as at an institution or supplier), human resources, and so forth.

The flow of information, as indicated by the arrows in FIG. 1, may include a wide range of types and vehicles for information exchange, as described more fully below. In general, the patient 4 may interface with clinicians 6 through conventional clinical visits, as well as remotely by telephone, electronic mail, forms, and so forth. The patient 4 may also interact with elements of the resources 18 via a range of patient data acquisition interfaces 16, which may include conventional patient history forms, interfaces for imaging systems, systems for collecting and analyzing tissue samples, body fluids, and so forth. Interaction between the clinicians 6 and the interface 8 may take any suitable form, typically depending upon the nature of the interface. Thus, the clinicians may interact with the data processing system 10 through conventional input devices such as keyboards, computer mice, touch screens, portable or remote input and reporting devices. Moreover, the links between the interface 8, data processing system 10, the knowledge base 12, the federated database 14 and the resources 18 will be described more fully below, but may typically include computer data exchange interconnections, network connections, local area networks, wide area networks, dedicated networks, virtual private network, and so forth.

As noted generally in FIG. 1, the data processing and interconnection of the various resources, databases, and processing components can vary greatly. For example, FIG. 1 illustrates the federated database as being linked to both the data processing system 10 and to the resources 18. Such arrangements will permit the federated database, and the software contained therein, to extract and access information from various resources, while providing the information to the data processing system 10 upon demand. The data processing system 10, in certain instances, may directly extract or store information in the resources 18 where such information can be accessed and interpreted or translated. Similarly, the data processing system 10 can be linked to the integrated knowledge base 12 and both of these components can be linked to the interface 8. The interface 8, which may be subdivided into specific interface types or components, may thus be used to access knowledge directly from the integrated knowledge base 12, or to command data processing system 10 to acquire, analyze, process or otherwise manipulate data from the integrated knowledge base or the resources. Such links between the data are illustrated diagrammatically in the figures for explanatory purposes. In specific systems, however, the high degree of integration may follow specific software modules or programs which perform specific analyses or correlations for specific patients, specific disease states, specific institutions, and so forth.

Throughout the present discussion, the resources 12 will be considered to include two primary types of resource. First, a purely data resource may consist of various types of previously-acquired, analyzed and stored data. That is, the data resources may be thought of as reference sources which may represent information regarding medical events, medical conditions, disease states, financial information, and so forth, as discussed more fully below. The data resources do not, in general, require information to be gathered directly from the patient. Rather, these resources are more general in nature and may be obtained through data reference libraries, subscriptions, and so forth. A second type of resource comprising knowledge base 12 consists of controllable and prescribable resources. These resources include any number of data gathering devices, mechanisms, and procedures which acquire data directly or indirectly from the patient. More will be said of these resources later in the present discussion, but, in general they may be thought of as clinical resources such as imaging systems, electrical parameter detection devices, data input by clinicians in fully or partially-automated or even manual procedures, and so forth.

Figure 2:
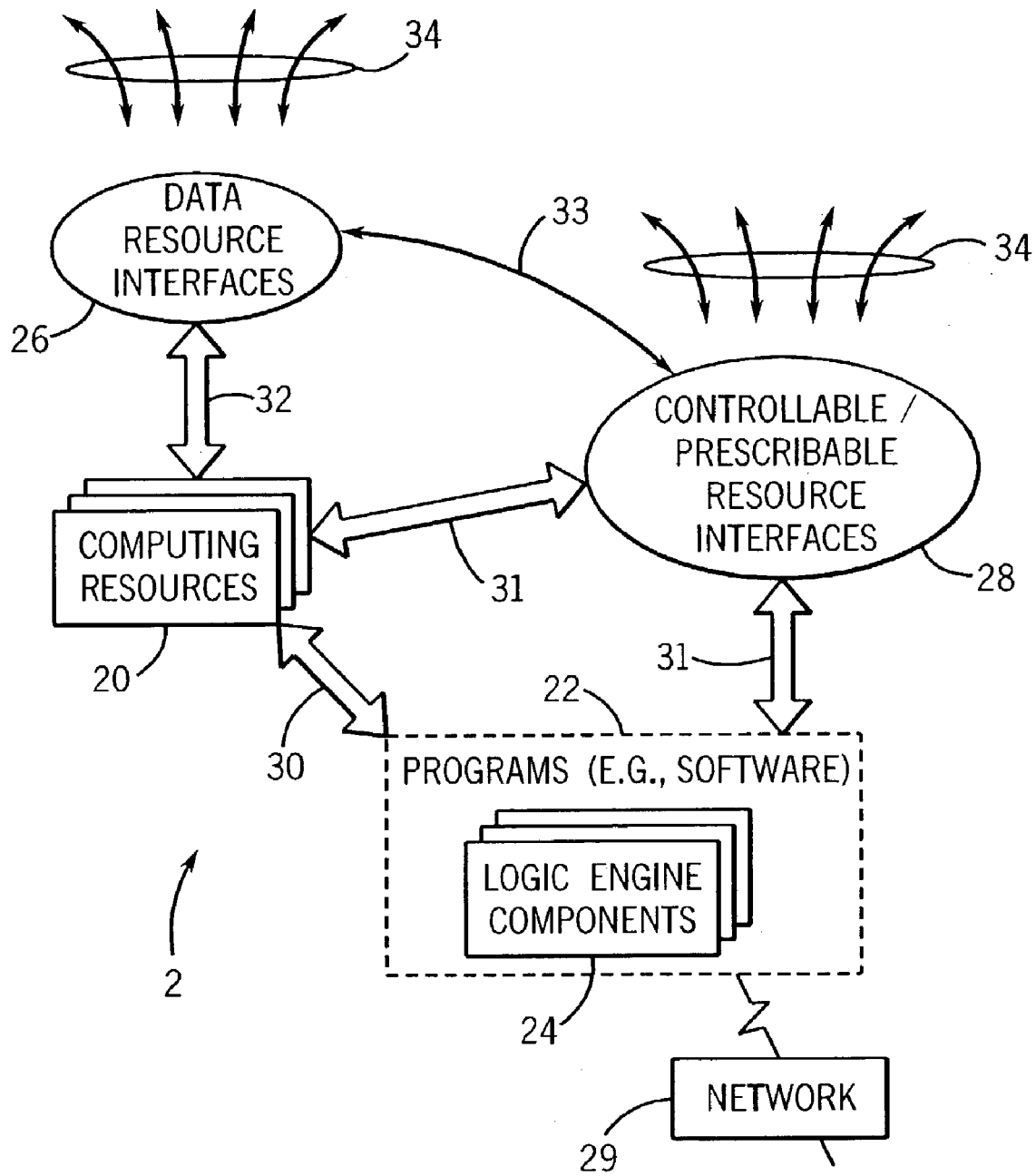
FIG. 2 is a diagrammatical representation of certain exemplary components of a data processing system of the type illustrated generally in FIG. 1.

FIG. 2 illustrates in somewhat greater detail the types of components associated with the data processing system 10. In general, the data processing system 10 may include a single computer, but for more useful and powerful implementations, a wide array of computing and interface resources. Such resources, designated generally at reference numeral 20, may include application-specific computing devices, general purpose computers, servers, data storage devices, and so forth. Such devices may be positioned at a single principle location, but also may be widely geographically placed and drawn upon as desired, such as via wide area networks, local area networks, virtual private networks, and so forth. The computing resources draw upon and implement programs, designated generally at reference numeral 22, which codify and direct the data extraction, analysis, compilation, reporting and similar functions performed by the data processing system. In general, such programs may be embodied in software, although certain programs may be hard-wired into specific components, or may constitute firmware within or between certain components. As described more fully below, the programs 22 may be considered to include certain logic engine components 24 which drive the analysis functions performed by the data processing system 10. Such logic engine components may assist in diagnosis of medical events and conditions, but may also be used for a wide range of other functions as described below. Such functions may include prescription and control of the controllable and prescribable resources, proposals for patient care, analysis of financial arrangements and conditions, analysis of patient care, teaching and instruction, to mention but a few of the possible applications.

The computing resources 20 are designed to draw upon and interface with the data resources discussed above via data resource interfaces 26, which may be part of federated database 14 (see, FIG. 1). Moreover, the data resource interfaces 26 will typically include computer code stored both at the computing resources 20 and additional code which may be stored within these specific data resources, as well as code that permits communication between the computing resources and the data resources. Accordingly, such code will permit information to be searched, extracted, transmitted, and stored for processing by the computing resources. Moreover, the data resource interfaces 26 will allow for data to be sent from the computing resources, where desired, and stored within the data resources. When necessary, the data resource interfaces will also permit translation of the data from one form to another so as to facilitate its retrieval, analysis, and storage. Such translation may include compression and decompression techniques, file formatting, and so forth.

The computing resources 20 also interface with the controllable and prescribable resources via interfaces 28, which may also be included in the federated database. Like interfaces 26, interfaces 28 may include code stored, as noted above at the computer resources, as well as codes stored at the specific locations or systems which comprise the controllable and prescribable resources. Thus, the interfaces will typically include code which identifies types of information sought, permitting location and extraction of the information, translation of the information, where necessary, manipulation of the information and storage of the information. The interfaces may also permit information to be loaded to the controllable and prescribable resources from the computing resources, such as for configurations of systems and parameters for carrying out examinations, reports, and so forth. It should also be noted that certain of the computing resources may actually be located at or even integral with certain of the controllable and prescribable resources, such as computer systems and controllers within imaging equipment, electrical data acquisition equipment, or other resource systems. Thus, certain of the operations and analysis performed by the logic engine components 24 or, more generally, by the programs 22, may be implemented directly at or local to the controllable and prescribable sources.

Also illustrated in FIG. 2 is a network 29 which is shown generally linked to the data processing system 10. The network 29, while possibly including links to the data resource interfaces, the data resources, the controllable and prescribable resources, and so forth, may provide additional links to users, institutions, patients, and so forth. Thus, the network 29 may route data traffic to and from the various components of the data processing system 10 so as to permit data collection, analysis and reporting functions more generally to a wider range of participants.

As noted by the arrows in FIG. 2, a wide range of network configurations may be available for communicating between and among the various resources and interfaces. For example, as noted by arrow 30, the computing resources 20 may draw upon program 22 both directly (e.g. internally of computer systems), or via local or remote networking. Thus, the computing resources may permit execution of routines based upon programs stored and accessed on an "as-needed" basis, in addition to programs immediately accessible from within specific computer systems.

Arrows 31 and 32 represent, generally, more varied data interchange pathways, such as configurable and dedicated networks, that allow for high-speed data exchange between the various resources. Similar communications may be facilitated between the data resource interfaces and the controllable and prescribable resource interfaces as noted at arrow 33 in FIG. 2. Such exchanges may be useful for drawing upon specific data resource information in configuring or operating the controllable and prescribable resources. By way of example, the data resource interfaces may permit extraction of population information, "best practice" system configurations, and so forth which can be stored within the controllable and prescribable resources to facilitate their operation as dictated by analysis performed by the computing resources. Arrows 34 refer generally to various data links between the interfaces 26 and 28 and the components of the knowledge base as described below, such links may include any suitable type of network connection or even internal connections within a computer system. In a case of all of the data communications 30, 31, 32, 33 and 34, any range of network or data transfer means may be envisaged, such as data busses, dial-up networks, high-speed broadband data exchanges, wireless networks, satellite communication systems, and so forth.

Data Resources

Figure 3:
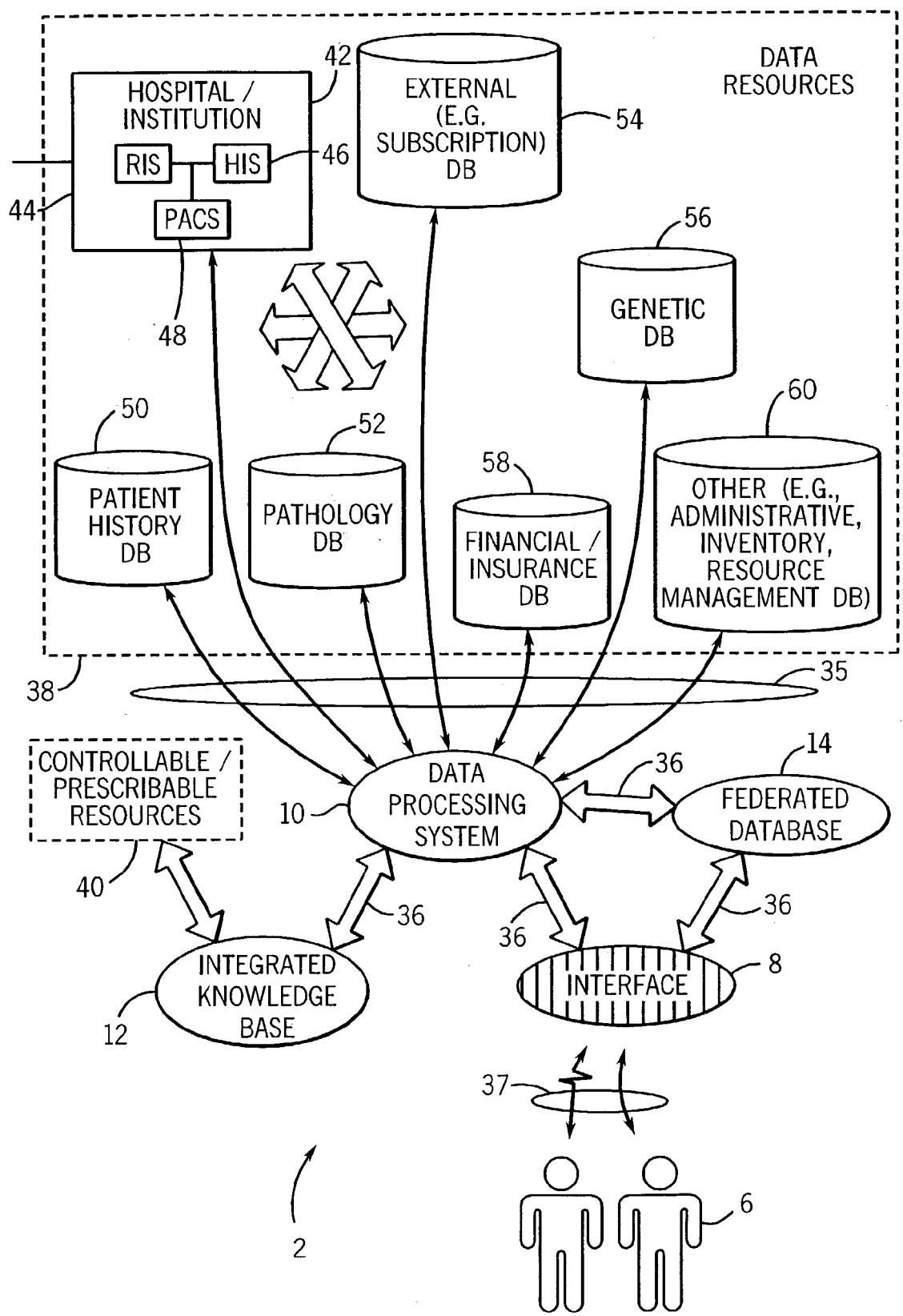
FIG. 3 is a diagrammatical representation of certain exemplary data resources that could form part of a knowledge base employed in the system of FIG. 1.

FIG. 3 illustrates certain exemplary components which may be included within the data resource segment of the resources discussed above and illustrated in FIG. 1. The data resources denoted generally at reference numeral 38 in FIG. 3, are designed to communicate with the data processing system 10 as noted above with reference to FIG. 2 and as indicated by arrows 35 in FIG. 3. In turn, the data processing system is available as a resource to clinicians 6 via interface 8 and may further communicate with the controllable and prescribable resources 40 as indicated by arrows 36. As noted in FIG. 3, the clinicians may have direct access and interface directly with the data processing system, or access to the data processing system 10 indirectly via remote networking arrangements as denoted by the straight and broken arrows 37.

The data processing system, in addition to drawing upon and communicating with the data resources 38, communicates with the controllable and prescribable resources as indicated at reference numeral 40 and discussed more fully below. As noted above, the data resources may generally be thought of as including information and data which can be identified, localized, extracted and utilized by the data processing system 10. Moreover, the data processing system may write data to the various resources where appropriate.

As illustrated in FIG. 3, the data resources 38 may include a range of information types. For example, many sources of information may be available within a hospital or institution as indicated at reference numeral 42. As will be appreciated by those skilled in the art, the information may be included within a radiology department information system 44, such as in scanners, control systems, or departmental management systems or servers. Similarly, such information may be stored in an institution within a hospital information system 46 in a similar manner. Many such institutions further include data, particularly image data, archiving systems, commonly referred to as PACS 48 in the form of compressed and uncompressed image data, data derived from such image data, data descriptive of system settings used to acquire images (such as in DICOM or other headers appended to image files), and so forth. In addition to data stored within institutions, data may be available from patient history databases as indicated at reference numeral 50. Such databases, again, may be stored in a central repository within an institution, but may also be available from remote sources to provide patient-specific historical data. Where appropriate, such patient history databases may group a range of resources searchable by the data processing system and located in various institutions or clinics.

Other data resources may include databases such as pathology databases 52. Such databases may be compiled both for patient-specific information, as well as for populations of patients or persons sharing medical, genetic, demographic, or other traits. Moreover, external databases, designated generally by reference numeral 54, may be accessed. Such external databases may be widely ranging in nature, such as databases of reference materials characterizing populations, medical events and states, treatments, diagnosis and prognosis characterizations, and so forth. Such external databases may be accessed by the data processing system on specific subscription bases, such as on ongoing subscription arrangements or pay-per-use arrangements. Similarly, genetic and similar databases 56 may be accessed. Such genetic databases may include gene sequences, specific genetic markers and polymorphisms, as well as associations of such genetic information with specific individuals or populations. Moreover, financial, insurance and similar databases 58 may be accessible for the data processing system 10. Such databases may include information such as patient financial records, institution financial records, payment and invoicing records and arrangements, Medicaid or Medicare rules and records, and so forth.

Finally, other databases, as denoted at reference numeral 60 may be accessed by the data processing system. Such other databases may, again, be specific to institutions, imaging or other controllable or prescribable data acquisition systems, reference materials, and so forth. The other databases, as before, may be available free or even internal to an institution or family of institutions, but may also be accessed on a subscription bases. Such databases may also be patient-specific, or population-specific to assist in the analysis, processing and other functions carried out by the data processing system 10. Furthermore, the other databases may include information which is clinical and non-clinical in nature. For assistance in management of financial and resource allocation, for example, such databases may include administrative, inventory, resource, physical plant, human resource, and other information which can be accessed and managed to improve patient care.

As indicated by the multiple-pointed arrow in the data resources grouping 38 in FIG. 3, the various data resources may also communicate between and among themselves. Thus, certain of the databases or database resources may be equipped for the direct exchange of data, such as to complete or compliment data stored in the various databases. While such data exchange may be thought of generally as passing through the data processing system 10, in a more general respect, the resources may facilitate such direct data exchange as between institutions, data repositories, computer systems, and the like with the data processing system 10 drawing upon such exchange data from one or more of the resources as needed.

Controllable/Prescribable Resources

Figure 4:
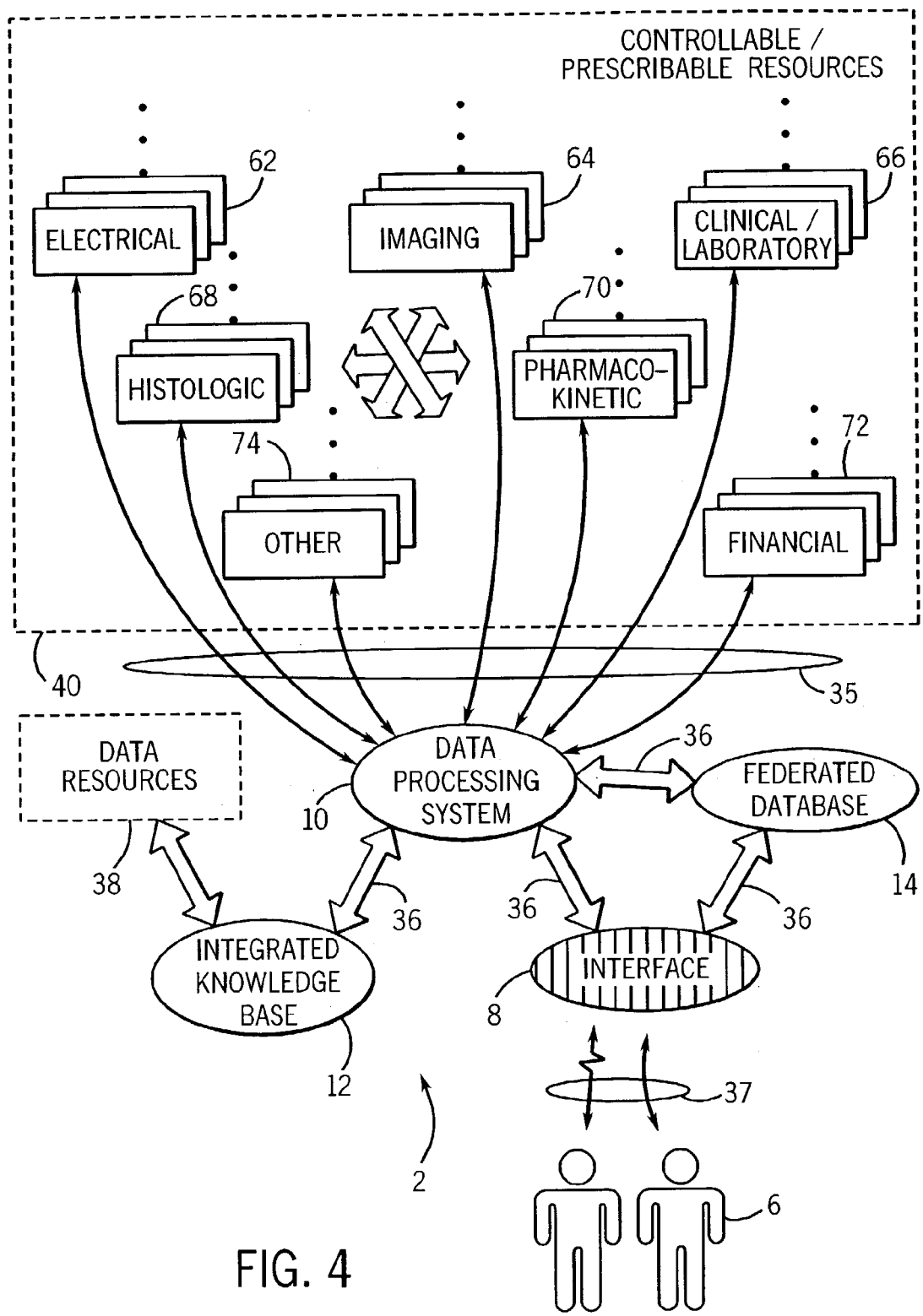
FIG. 4 is a diagrammatical representation of certain exemplary of the controllable and prescribable resources that may be employed in the system of the type illustrated in FIG. 1.

FIG. 4 similarly indicates certain of the exemplary controllable and prescribable resources which may be accessed by the data processing system 10. As before, the data processing system is designed to interface with clinicians 6 through appropriate interfaces 8, as well as with the data resources 38.

In general, the controllable and prescribable resources 40 may be patient-specific or patient-related, that is, collected from direct access either physically or remotely (e.g. via computer link) from a patient. The resource data may also be population-specific so as to permit analysis of specific patient risks and conditions based upon comparisons to known population characteristics. It should also be noted that the controllable and prescribable resources may generally be thought of as processes for generating data. Indeed, while may of the systems and resources described more fully below will themselves contain data, these resources are controllable and prescribable to the extent that they can be used to generate data as needed for appropriate treatment of the patient. Among the exemplary controllable and prescribable resources 40 are electrical resources denoted generally at reference numeral 62. Such resources, as described more fully below, may include a variety of data collection systems designed to detect physiological parameters of patients based upon sensed signals. Such electrical resources may include, for example, electroencephalography resources (EEG), electrocardiography resources (ECG), electromyography resources (EMG), electrical impedance tomography resources (EIT), nerve conduction test resources, electronystagmography resources (ENG), and combinations of such resources. Moreover, various imaging resources may be controlled and prescribed as indicated at reference numeral 64. A number of modalities of such resources are currently available, such as X-ray imaging systems, magnetic resonance (MR) imaging systems, computed tomography (CT) imaging systems, positron emission tomography (PET) systems, flouorography systems, mammography systems, sonography systems, infrared imaging systems, nuclear imaging systems, thermoacoustic systems, and so forth.

In addition to such electrical and highly automated systems, various controllable and prescribable resources of a clinical and laboratory nature may be accessible as indicated at reference numeral 66. Such resources may include blood, urine, saliva and other fluid analysis resources, including gastrointestinal, reproductive, and cerebrospinal fluid analysis system. Such resources may further include polymerase (PCR) chain reaction analysis systems, genetic marker analysis systems, radioimmunoassay systems, chromatography and similar chemical analysis systems, receptor assay systems and combinations of such systems. Histologic resources 68, somewhat similarly, may be included, such as tissue analysis systems, cytology and tissue typing systems and so forth. Other histologic resources may include immunocytochemistry and histopathological analysis systems. Similarly, electron and other microscopy systems, in situ hybridization systems, and so forth may constitute the exemplary histologic resources. Pharmacokinetic resources 70 may include such systems as therapeutic drug monitoring systems, receptor characterization and measurement systems, and so forth.

In addition to the systems which directly or indirectly detect physiological conditions and parameters, the controllable and prescribable resources may include financial sources 72, such as insurance and payment resources, grant sources, and so forth which may be useful in providing the high quality patient care and accounting for such care on an ongoing basis. Miscellaneous other resources 74 may include a wide range of data collection systems which may be fully or semi-automated to convert collected data into a useful digital form. Such resources may include physical examinations, medical history, psychiatric history, psychological history, behavioral pattern analysis, behavioral testing, demographic data, drug use data, food intake data, environmental factor information, gross pathology information, and various information from non-biologic models. Again, where such information is collected manually directly from a patient or through qualified clinicians and medical professionals, the data is digitized or otherwise entered into a useful digital form for storage and access by the data processing system.

As discussed above with respect to FIG. 3, the multi-pointed arrow shown within the controllable and prescribable resources 40 in FIG. 4 is intended to represent that certain of these resources may communicate directly between and among themselves. Thus, imaging systems may draw information from other imaging systems, electrical resources may interfaced with imaging systems for direct exchange of information (such as for timing or coordination of image data generation, and so forth). Again, while such data exchange may be thought of passing through the data processing system 10, direct exchange between the various controllable and prescribable resources may also be implemented.

Figure 5:
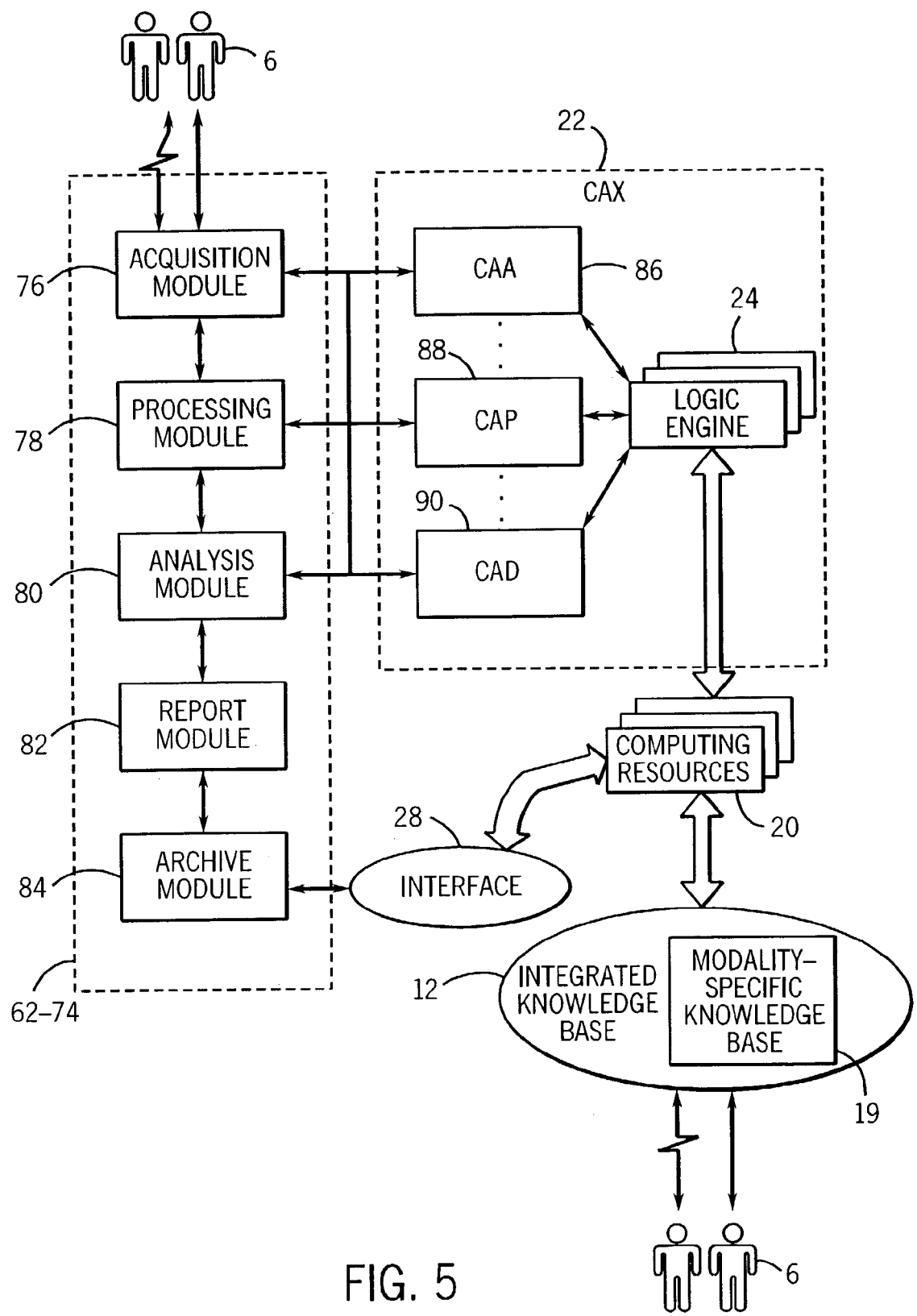
FIG. 5 is a general diagrammatical representation of exemplary modules within a controllable and prescribable resource, as well as certain modules which could be included in a data processing system in accordance with aspects of the present technique.

As noted above, the data resources may generally be thought of as information repositories which are not acquired directly from a specific patient. The controllable and prescribable resources, on the other hand, will typically include means for acquiring medical data from a patient through automated, semi-automated, or manual techniques. FIG. 5 generally represents certain of the functional modules which may be considered as included in the various controllable and prescribable resource types illustrated in FIG. 4. As shown in FIG. 5, such resources may be thought of as including certain general modules such as an acquisition module 76, a processing module 78, an analysis module 80, a report module 82, and an archive module 84. The nature of these various modules may differ widely, of course, depending upon the type of resource under consideration. Thus, the acquisition module 76 may include various types of electrical sensors, transducers, circuitry, imaging equipment, and so forth, used to acquire raw patient data. The acquisition module 76 may also include more human-based systems, such as questionnaires, surveys, forms, computerized and other input devices, and the like.

The nature and operation of the processing module 76, similarly will depend upon the nature of the acquisition module and of the overall resource type. Processing modules may thus include data conditioning, filtering, and amplification or attenuation circuits. However, the processing modules may also include such applications as spreadsheets, data compilation software, and the like. In electrical and imaging systems, the processing module may also include data enhancement circuits and software used to perform image and other types of data scaling, reconstruction, and display.

Analysis module 80 may include a wide range of applications which can be partially or fully automated. In electrical and imaging systems, for example, the analysis module may permit users to enhance or alter the display of data and reconstructed images. The analysis module may also permit some organization of clinician-collected data for evaluating the data or comparing the data to reference ranges, and the like. The report module 82 typically provides for an output or summary of the analysis performed by module 80. Reports may also provide an indication of techniques used to collect data, the number of data acquisition sequences performed, the types of sequences performed, patient conditions during such data acquisition, and so forth. Finally, archive module 84 permits the raw, semi-processed, and processed data to be stored either locally at the acquisition system or resource, or remote therefrom, such as in a database, repository, archiving system (e.g. PACS), and so forth.

The typical modules included within the controllable and prescribable resources may be interfaced with programs, as indicated at reference numeral 22, to enhance the performance of various acquisition, processing and analysis functions. As illustrated diagrammatically in FIG. 5, for example, various computer-assisted acquisition routines 86 may be available for analyzing previous acquisition sequences, and for prescribing, controlling or configuring subsequent data acquisition. Similarly, computer-assisted processing modules 88 may interface with the processing module 78 to perform additional or enhance processing, depending upon previous processing and analysis of acquired data. Finally, programs such as computer-assisted data operating algorithms (CAX) modules 90 may be used to analyze received and processed data to provide some indication of possible diagnoses that may be made from the data.

While more will be said later in the present discussion regarding the various types of controllable and prescribable resource types and modalities, as well as of the modules used to aid in the acquisition, processing, analysis and diagnosis functions performed on the data from such resources, it should be noted in FIG. 5 that various links between these components and resources are available. Thus, in a typical application, a computer-assisted acquisition module 86 may prescribe, control or configure subsequent acquisition of data, such as image data, based upon the results of enhanced processing performed by a computer-assisted processing module 88. Similarly, such acquisition prescription may result from output from a computer-assisted diagnosis module 90, such as to refine potential diagnosis made, based upon subsequent data acquisition. In a similar manner, a computer-assisted processing module 88 may command enhanced, different or subsequent processing by processing module 78 based upon output of computer-assisted module 86 or of a computer-assisted diagnosis module 90. The various modules, both of the resources, and of the programs, then, permit a high degree of cyclic and interwoven data acquisition, processing and analysis by virtue of the integration of these modules into the overall system in accordance with the present techniques.

As also illustrated in FIG. 5, for the typical controllable and prescribable resource, the programs executed on the data, and used to provide enhanced acquisition, processing and analysis, may be driven by a logic engine 24 of the programs 22. As noted above, and as discussed in greater detail below, the logic engine 24 may incorporate a wide range of algorithms which link and integrate the output of programs, such as CAX algorithms, certain of which are noted as CAA, CAP and CAD modules 86, 88 and 90 FIG. 5, and which prescribe or control subsequent acquisition, processing and analysis based upon programmed correlations, recommendations, and so forth. As also noted above, the programs 22 are accessed by and implemented via the computing resources 20. The computing resources 20 may interface generally with the archive module 84 of the particular resource modality via an appropriate interface 28 as mentioned above. Finally, the computing resources 20 interface with the integrated knowledge base 12. It should be noted from FIG. 5 that the knowledge base may also include modality-specific knowledge bases 19 which are repositories of information relating to the specific modality of the resource 62–74. Such modality-specific knowledge base data may include factors such as system settings, preferred settings for specific patients or populations, routines and protocols, data interpretation algorithms based upon the specific modality, and so forth. The knowledge bases are generally available to clinicians 6 and, where desired, may be based upon input from such clinicians. Thus, where appropriate, the knowledge base may be at least partially built by configuration input from specialists, particularly inputs relating to the specific resource modality, for purposes of enhancing and improving acquisition, processing, analysis, or multiple aspects of these processes.

Modality/Type Interaction

Figure 6:
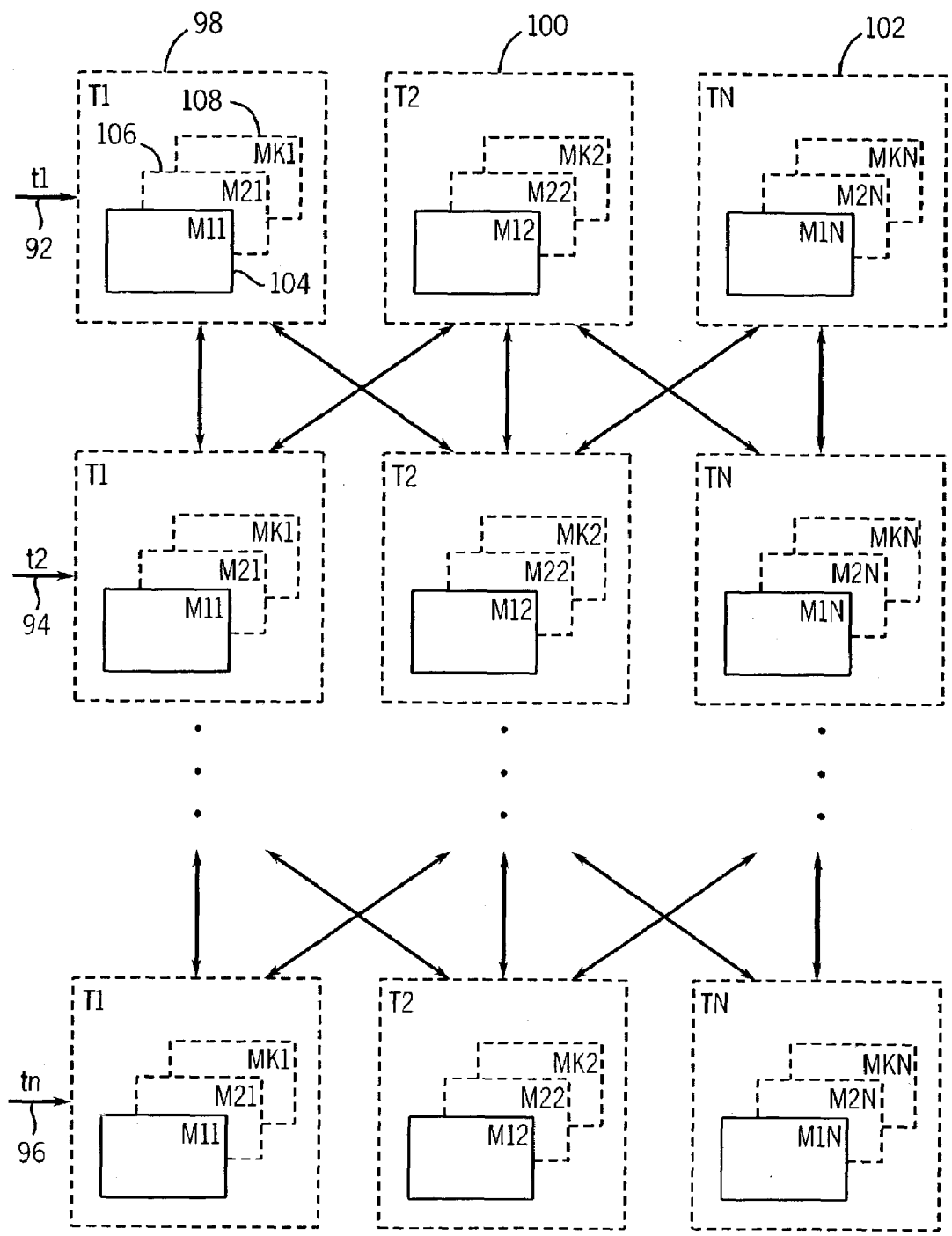
FIG. 6 is a diagrammatical representation of the overall structure of certain prescribable and controllable data resources, illustrating the availability of various modality resources within certain types and over certain time periods.

A particularly powerful aspect of the present technique resides in the ability to integrate various resource data between types of controllable and prescribable resources, between various modalities of these types, and between acquisition, processing and diagnosis made at various points in time. Such aspects of the present techniques are summarized diagrammatically in FIGS. 6 and 7. FIG. 6 illustrates, in a block form, a series of controllable and prescribable resource types 98, 100 and 102. These resource types, which may generally track the various designations illustrated in FIG. 4, and described above, may each comprise a series of modalities 104, 106 and 108. By way of example, type 98 may comprise various electrical resources denoted by reference numeral 62 in FIG. 4, while another type of resource 100 may include imaging resources 64 of FIG. 4. With each of these types the various modalities may include systems and procedures such as EEG, ECG, EMG, and so forth, for type 98, and X-ray, MRI, CT imaging systems, and so forth, for type 100.

In general, the representation of FIG. 6 illustrates that, in accordance with the present technique, the patient may have various procedures performed at a first time 92, which may include one or a range of data acquisition, processing and diagnosis functions for any one or more of the resource types 98, 100, 102, or any one or more or the modalities within each type. Based upon the results of such acquisition, processing and diagnosis, subsequent sessions of data acquisition, processing or diagnosis may be performed at a subsequent time 94. As indicated by the arrows between the blocks at these two points in time, control and prescription of subsequent data acquisition, processing and analysis may be appropriate. The subsequent operations may be performed on the same modality within a given resource type, or on a different modality of the same resource type. Similarly, the system may control or prescribe such procedures on entirely different types of resources, and for specific modalities within the different types of resources.

Subsequent procedures may then be performed at subsequent times, as indicated generally by reference numeral 96 in FIG. 6.

As will be appreciated by those skilled in the art, the technique provides a very powerful and highly integrated approach to control and prescription of medical data handling over time. For example, based upon the results of acquisition and analysis of electrical data, such as at time 92, an additional session may be scheduled for the patient wherein the system automatically or semi-automatically prescribes or controls acquisition of images via specific imaging systems. The system may also prescribe or control acquisition, processing or analysis of clinical laboratory data, histologic data, pharmacokinetic data, or other miscellaneous data types as described generally above. Over time, and between the various modalities and resource types, then, and in conjunction with data from the other data resources discussed above, the analysis may provide highly insightful feedback regarding medical events, medical conditions, disease states, treatments, predispositions for medical conditions and events, and so forth.

Figure 7:
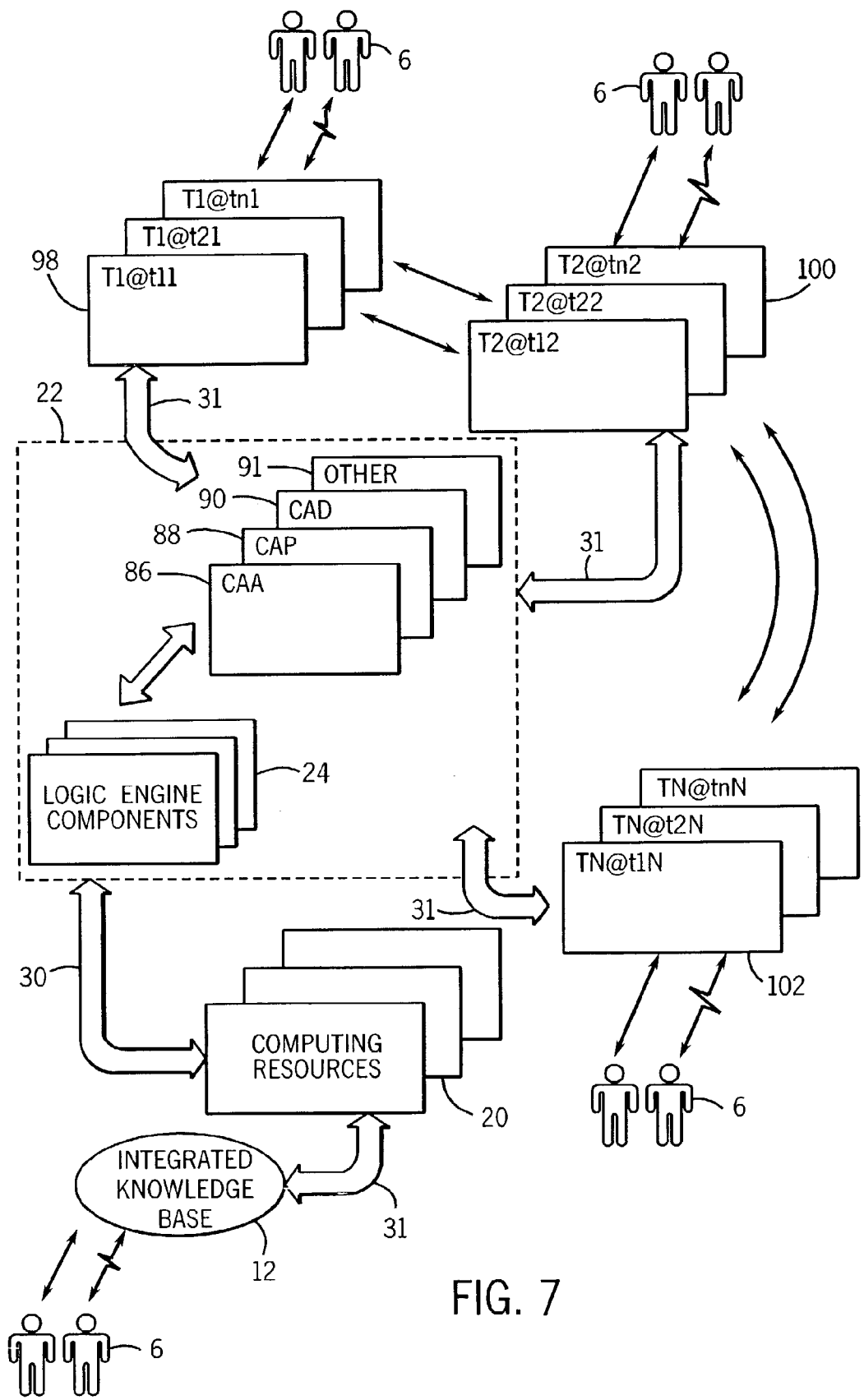
FIG. 7 is a diagrammatical representation of flow of information between certain data resource types as shown in FIG. 6, over certain time periods, and manners in which the information may be tied into the data processing system for analysis and prescription of additional data acquisition, processing or analysis.

The integration of this information over time is further illustrated in FIG. 7. As shown in FIG. 7, the various data collected, processed and analyzed at the various points in time, and from the various resource types indicated by reference numerals 98, 100, 102, are made available to and processed by the computing resources 20 via the programs 22. As noted above, such processing may include a wide range of operations performed on available data, such as for analysis, prescription and control through the use of CAX algorithms, as noted for certain such algorithms CAA 86, CAP 88, CAD 90, or other program modules made available to the computing resources 20. Other such modules may be provided as part of an application, or software suite, or added over time, as indicated generally at reference numeral 91. The logic engine components 24 aid in correlating the data and in prescribing or controlling the subsequent acquisition, processing and analysis of data from one or more of the modalities of one or more of the resource types. Ultimately, the computing resources may make the information available to the clinicians 6 as part of the integrated knowledge base 12.

Several points may be made with regards to the diagrammatical representations of FIG. 7. Firstly, the various interconnections between the elements of the system will generally be provided by direct or indirect communications links as discussed above. Moreover, interconnections and data exchange between the various resource types 98, 100 and 102 may be facilitated by direct interconnections between the components as discussed above. This is the case both between modalities of each type, as well as between various modalities of different types. The same is true for interconnections for data exchange between such types and modalities over time, as discussed above with respect to FIG. 6. Finally, while clinicians 6 are illustrated at various positions in the overall diagrammatical representation of FIG. 7, it should be noted that these may include the same or different clinicians, depending upon the modalities and types employed, and the needs of the patient. That is, specific clinicians or specialists may be provided for various resource types and even specific modalities, with different trained personnel being involved for other resource types and modalities. Ultimately, however, the general reference to clinicians 6 in the present context is intended to include all trained personnel that may, from time to time, and individually or as a team, provide inputs and care required by the medical situation.

The various types of controllable and prescribable resources, and the modalities of such resource types may include any available data resources which can be useful in performing the acquisition, processing, analysis functions offered by the present techniques. Specifically, the present technique contemplates that as few as a single resource may be provided, such as for integration of acquisition, processing and analysis over time, and, in a most useful configuration, a wide range of such resources are made available. FIG. 8 is a tabulated summary of certain exemplary resource types, designated generally by reference numeral 110, and modalities 112 within each of these types. As noted above, such controllable and prescribable resources may generally include electrical data sources, imaging data sources, clinical laboratory data sources, histologic data sources, pharmacokinetic data sources, and other miscellaneous sources of medical data. While various reference data on each of these types and modalities may be included in the data resources, the types and modalities enumerated in the table of FIG. 8 are designed to acquire data which is patient-specific and which is acquired either directly or indirectly from a patient. The following discussion relates to the various types and modalities summarized in FIG. 8 to provide a better understanding of the nature of such resources and the manner in which they may be used to evaluate medical events and conditions.

Electrical Data Resources

Figure 9:
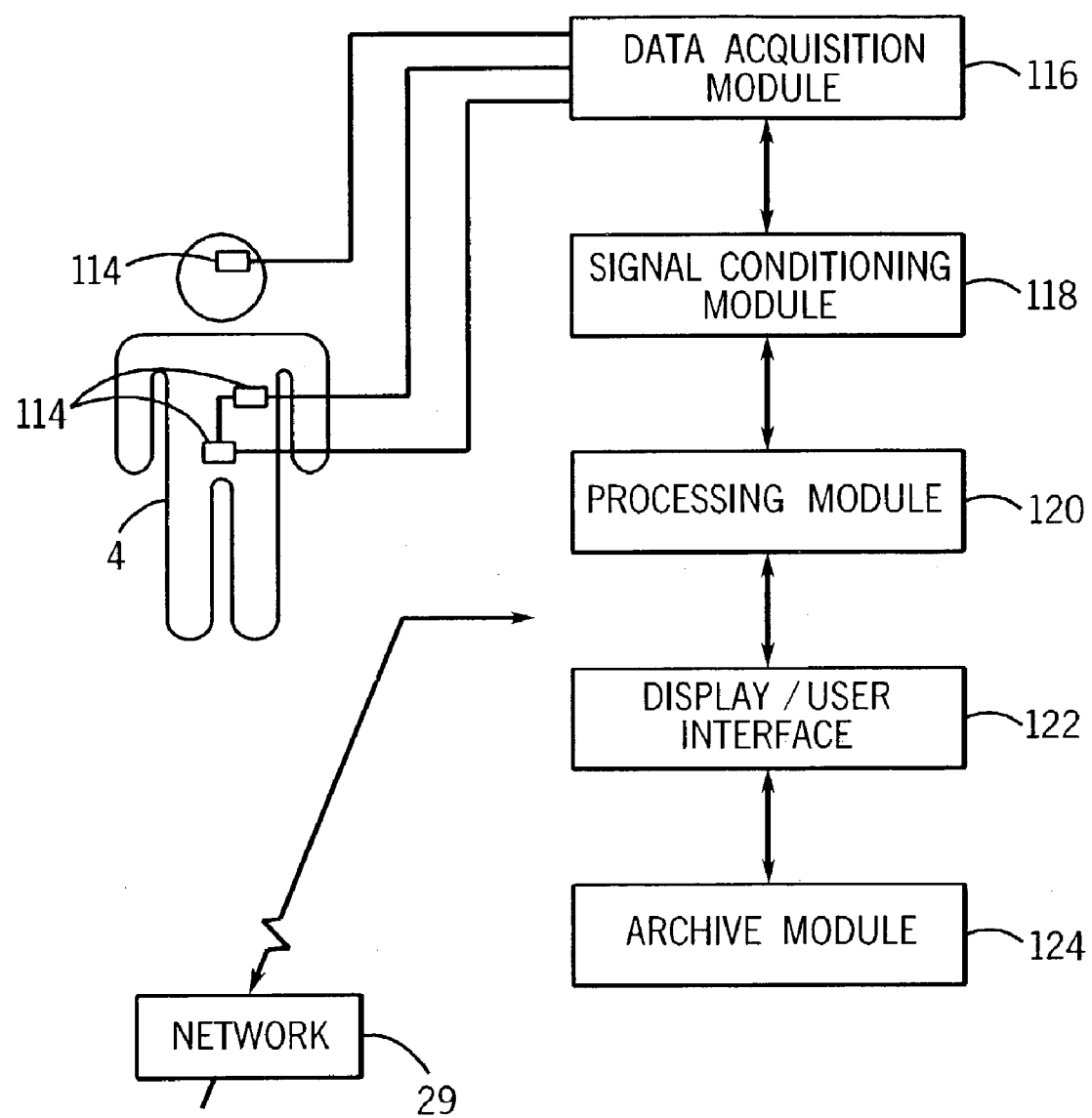
FIG. 9 is a general diagrammatical representation of a typical exemplary electrical data resource as mentioned in FIG. 8, which may include various general components or modules for acquiring electrical data representative of body function and state.

Electrical data resources of the controllable and prescribable type may be considered as including certain typical modules or components as indicated generally in FIG. 9. These components will include sensors or transducers 114 which may be placed on or about a patient to detect certain parameters of interest that may be indicative of medical events or conditions. Thus, the sensors may detect electrical signals emanating from the body or portions of the body, pressure created by certain types of movement (e.g. pulse, respiration), or parameters such as movement, reactions to stimuli, and so forth. The sensors 114 may be placed on external regions of the body, but may also include placement within the body, such as through catheters, injected or ingested means, capsules equipped with transmitters, and so forth.

The sensors generate signals or data representative of the sensed parameters. Such raw data are transmitted to a data acquisition module 116. The data acquisition module may acquire sampled or analog data, and may perform various initial operations on the data, such as filtering, multiplexing, and so forth. The data are then transmitted to a signal conditioning module 118 where further processing is performed, such as for additional filtering, analog-to-digital conversion, and so forth. A processing module 120 then receives the data and performs processing functions, which may include simple or detailed analysis of the data. A display/user interface 122 permits the data to be manipulated, viewed, and output in a user-desired format, such as in traces on screen displays, hardcopy, and so forth. The processing module 120 may also mark or analyze the data for marking such that annotations, delimiting or labeling axes or arrows, and other indicia may appear on the output produced by interface 122. Finally, an archive module 124 serves to store the data either locally within the resource, or remotely. The archive module may also permit reformatting or reconstruction of the data, compression of the data, decompression of the data, and so forth. The particular configuration of the various modules and components illustrated in FIG. 9 will, of course, vary depending upon the nature of the resource and the modality involved. Finally, as represented generally at reference numeral 29, the modules and components illustrated in FIG. 9 may be directly or indirectly linked to external systems and resources via a network link.

The following is a more detailed discussion of certain electrical data resources available for use in the present technique.

EEG

Electroencephalography (EEG) is a procedure, typically taking one to two hours, that records the electrical activity of the brain via sensors or electrodes that are attached to a patient's head and coupled to a computer system. The process records the electrical discharge of the brain as sensed by the electrodes. The computer system displays the brain electrical activity as traces or lines. Patterns that develop are recorded and can be used to analyze brain activity. Several types of brainwaves may be identified in the patterns, including alpha, beta, delta and theta waves, each of which are associated with certain characteristics and activities. Variations from normal patterns of brain activity can be indicative of certain brain abnormalities, medical events, conditions, disease states, and so forth.

In preparation for an EEG test, certain foods and medications are generally avoided as these can affect the brain activity and produce abnormal test results. The patient may also be asked to take necessary steps to avoid low blood sugar (hypoglycemia) during the test, and may be prepared to sleep if necessary as certain types of abnormal brain activity must be monitored during sleep. Performance of an EEG may take place in a hospital or clinic and the examination is typically performed by an EEG technologist. The technologist secures the electrodes, typically 16–25, at various places on the patient's head, using paste or small needles to hold the electrodes in place. A physician, typically a neurologist, analyzes the EEG record. During the procedure, the patient may be asked to simple relax, or various forms of stimulation may be introduced, such as having the patient breath rapidly (hyperventilate) or view a strobe to observe the brain response to such stimuli. An EEG is typically performed to diagnose specific potential events or conditions, such as epilepsy, or to identify various types of seizures that a patient may experience in conjunction with such disorders. EEG examinations may also be used to evaluate suspected brain tumors, inflammation, infection (such as encephalitis), or diseases of the brain. The examinations may also be used to evaluate periods of unconsciousness or dementia. The test may also evaluate the patient's prognosis for recovery after cardiac arrest or other major trauma, to confirm brain death of a comatose patient, to study sleep disorders, or to monitor brain activity while a person is receiving general anesthesia during surgery.

ECG

Electrocardiography (EKG, ECG) is a procedure, typically requiring a 10–15 minute examination, that records electrical activity of the heart via electrodes attached to a patient's skin and coupled to a data acquisition system. The electrodes detect electrical impulses and do not apply electricity to the body. The electrodes detect activity of the body's electrical system that result in cardiac activity. The electrical activity is detected, typically, through the skin on the chest, arms and legs of the patient where the electrodes are placed. The patient clothing may be removed above the waist and stockings or pants moved such that the patient's forearms and lower legs are exposed. The examination, typically performed by a specialized clinician, may be scheduled in a hospital, clinic or laboratory. After the test, a cardiologist typically analyzes the electrocardiography record. During the procedure, the patient is typically asked to lie on a bed or table, although other procedures require specific types of activities, including physical exertion. During the examination where appropriate, the patient may be asked to rest for a period of time before the test is performed. The electrodes used to detect the electrical activity, typically 12 or more, are placed at the desired locations via adhesive or other means. The areas may be cleaned and possibly shaven to facilitate placement and holding of the electrodes. Additionally, a conductive pad or paste may be employed to improve the conduction of the electrical impulses.

The acquisition system translates the electrical activity as indicated by the impulses, into traces or lines. The ECG traces will typically follow characteristic patterns of the electrical impulses generated by the heart. Various parts of the characteristic pattern may be identified and measured, including portions of a waveform typically referred to as the P-wave, the QRS complex, the ST segment and the T-wave. These traces may be analyzed by a computer or cardiologist for abnormalities which may be indicative of medical events or conditions. The ECG procedure is typically employed to identify such conditions as heart enlargement, signs of insufficient blood flow to the heart, signs of new or previous injury to the heart (e.g. resulting from heart attack), heart arrhythmias, changes in electrical activity of the heart caused by a chemical imbalance in the body, signs of inflammation of the pericardium, and so forth.

EMG

Electromyography (EMG) is a procedure, typically taking from 1–3 hours, designed to measure electrical discharges resulting from contraction of muscles. In general, as muscles contract, electrical signals are generated which can be detected by sensors placed on a patient. EMG and nerve conduction studies, summarized below, can be used to assist in the detection of the presence, location and existence of conditions and diseases that can damage muscle tissue or nerves. EMG examinations and nerve conduction studies are commonly performed together to provide more complete information.

In preparation for an EMG examination, a patient is typically called upon to avoid certain medications and stimulants for a certain time period, such as three hours, before the examination. Specific conditions such as bleeding or thinning of the blood, and practices such as the use of a cardiac stimulator are noted prior to the examination. In the EMG examination itself, a clinician in a hospital or clinic screens out extraneous electrical interference. A neurologist or physical rehabilitation specialist may also perform the test, where desired. During the procedure, the patient is generally asked to take a relaxed position, and muscles subject to the test are positioned to facilitate their access. Skin areas overlying the muscles to be tested are cleaned and electrodes are placed on the skin, including a reference electrode and a recording electrode. The reference electrode may typically include a flat metal disk which is attached to the skin near the test area, or a needle inserted just below the skin near the test area. The recording electrode typically comprises a needle, attached via conducting wires to a data acquisition device or recorder. The recording electrode is inserted into the muscle tissue to be tested. Electrical activity of the muscle is being tested is then recorded via the two electrodes both at rest and during contraction, typically with gradually increasing contraction force. Repositioning of the electrodes may be required to record activity in different areas of the muscle or in different muscles. Electrical activity data thus gathered may be displayed and typically takes the form of spiked waveforms.

The results of EMG examinations may be analyzed alone, although they typically are used in conjunction with other data to diagnose conditions. Such other data may include the patient's medical history, information regarding specific symptoms, as well as information gathered from other examinations. The EMG examination are typically performed to provide assistance in diagnosing disease that can damage muscle tissue, nerves or junctions between nerve and muscle, or to evaluate the causes of weakness, paralysis or involuntary muscle stimulation. Such examinations can also be used to diagnose conditions such as post-polio syndrome, as well as other conditions affecting normal muscle activity.

EIT

Electrical impedance tomography (EIT) is a non-invasive process designed to provide information regarding electrical parameters of the body. Specifically, the process maps the electrical conductivity and permittivity within the body. Electrical conductivity is a measure of the ease with which a material conducts electricity, while electrical permittivity is a measure of the ease with which charges within a material will separate when an imposed electric field is introduced. Materials with high conductivity allow the passage of direct and alternating current. High permittivity materials, on the other hand, allow only the passage of alternating currents. Alternate data gathering of electrical conductivity and permittivity within the body are obtained in a typical examination, by applying current to the body via electrodes attached to the patient's skin and by measuring resulting voltages. The measurements permit computations of impedance of body tissues, which may be used to create images of the tissues by reconstruction.

Because the electric current supplied during the examination will assume the path of least impedance, current flow through the tissues will depend upon the conductivity distribution of the tissues of the patient. Data obtained is then used to reconstruct images of the tissues, through various reconstruction techniques. In general, the image reconstruction process comprises a non-linear mathematical computation, and the resulting images can be used for various diagnosis and treatment purposes. For example, the process can be used to detect blood clots in the lungs or pulmonary emboli. The process can also be used to detect lung problems including collapsed lungs and accumulation of fluid. Other conditions which can be detected include internal bleeding, melanomas, cancers, such as breast cancer, as well as a variety of other medical events and conditions.

Nerve Conduction Tests

Nerve conduction studies have been used to measure how well individual nerves can transmit electrical signals. Both nerve conduction studies and EMG studies can be used to aid in the detection and location of diseases that can damage muscle tissue or nerves. Nerve conduction studies and EMG are often done together to provide more complete information for diagnosis. Nerve conduction studies are typically done first if both tests are performed together.

In preparation for a nerve conduction study, a patient is generally asked to avoid medications, as well as stimulants such as tobacco and caffeine. Additionally, issues with bleeding or blood thinning, and the use of cardiac implants are identified prior to the test. The nerve conduction study itself is generally performed by a technologist and may take place in a hospital or clinic or in a special room designed to screen electrical interference. A neurologist or physical rehabilitation specialist commonly performs the test. During the procedure, the patient is asked to recline or sit and areas of the body to be tested are relaxed. Several flat metal disk electrodes are attached to the patient's skin, and a charge-emitting electrode is placed over a nerve to be tested. A recording electrode is placed over the muscle controlled by the nerve. Electrical impulses are repeatedly administered to the nerve and the conduction velocity, or time required to obtain muscle response, is then recorded. A comparison of response times may be made between corresponding muscles on different sides of the body. The nerve conduction study may be performed, as noted above, to detect and evaluate damage to the peripheral nervous system, to identify causes of abnormal sensations, to diagnose post-polio syndrome, as well as to evaluate other symptoms.

ENG

Electronystagmography (ENG) refers to a series of tests designed to evaluate how well a patient maintains a sense of position and balance through coordinated inputs of the eyes, inner ears and brain. ENG tests can be utilized, for example, to determine whether dizziness or vertigo are caused by damage to nerve structures in the inner ear or brain. The tests utilize electrodes which are attached to the facial area and are wired to a device for monitoring eye movements. During an ENG test series, certain involuntary eye movements, referred to as nystagmus, which normally occur as the head is moved, are measured. Spontaneous or prolonged nystagmus may be indicative of certain conditions affecting the nerves or structures of the inner ear or brain.

In preparation for an ENG test series, the patient is generally asked to avoid certain medications, and stimulants for an extended period. Visual and hearing aids, as well as facial cosmetics, may need to be avoided or removed due to possible interference with electrodes used during the tests. For the examination, a series of electrodes, typically five, are attached to the patient's face using a conductive adhesive. The patient is tested in a seated position in a darkened room. During the examination, instrumentation is adjusted for measuring or monitoring how a patient follows a moving point using only the eyes. Readings are then taken while the patient performs mental tasks with the eyes closed, gazes straight ahead and to each side, follows movement of a pendulum or other object with the eyes, and moves the head and body to different positions. Additionally, eye movements may be monitored during a caloric test, which involves warm or cool air or water being placed or blown inside the patient's ears. During such tests the electrodes detect eye movement and the monitoring system translates the movement into line recordings. The caloric test may be performed with or without the use of electrodes to detect eye movement. The results of the test are analyzed to determine whether abnormal involuntary eye movements are detected, whether head movement results in vertigo, and whether eye movements have normal intensity and direction during the caloric test. If such abnormal involuntary eye movements occur during the test, or if vertigo or abnormal eye movement is detected during the caloric test, results maybe indicative of possible brain or nerve damage, or damage to structures of the ear affecting balance.

Combinations

Various combinations of the foregoing procedures maybe used in conjunction to obtain more detail or specific information. In particular, as noted above, nerve conduction tests and EMG studies are often done to compliment one another. However, based upon the results of one or more of the electrical tests described above other, more detailed tests of the same nature or of different types may be in order. The analyses may be combined or considered separately to better identify potential abnormalities, physical conditions, or disease states.

Imaging Data Resources

Figure 10:
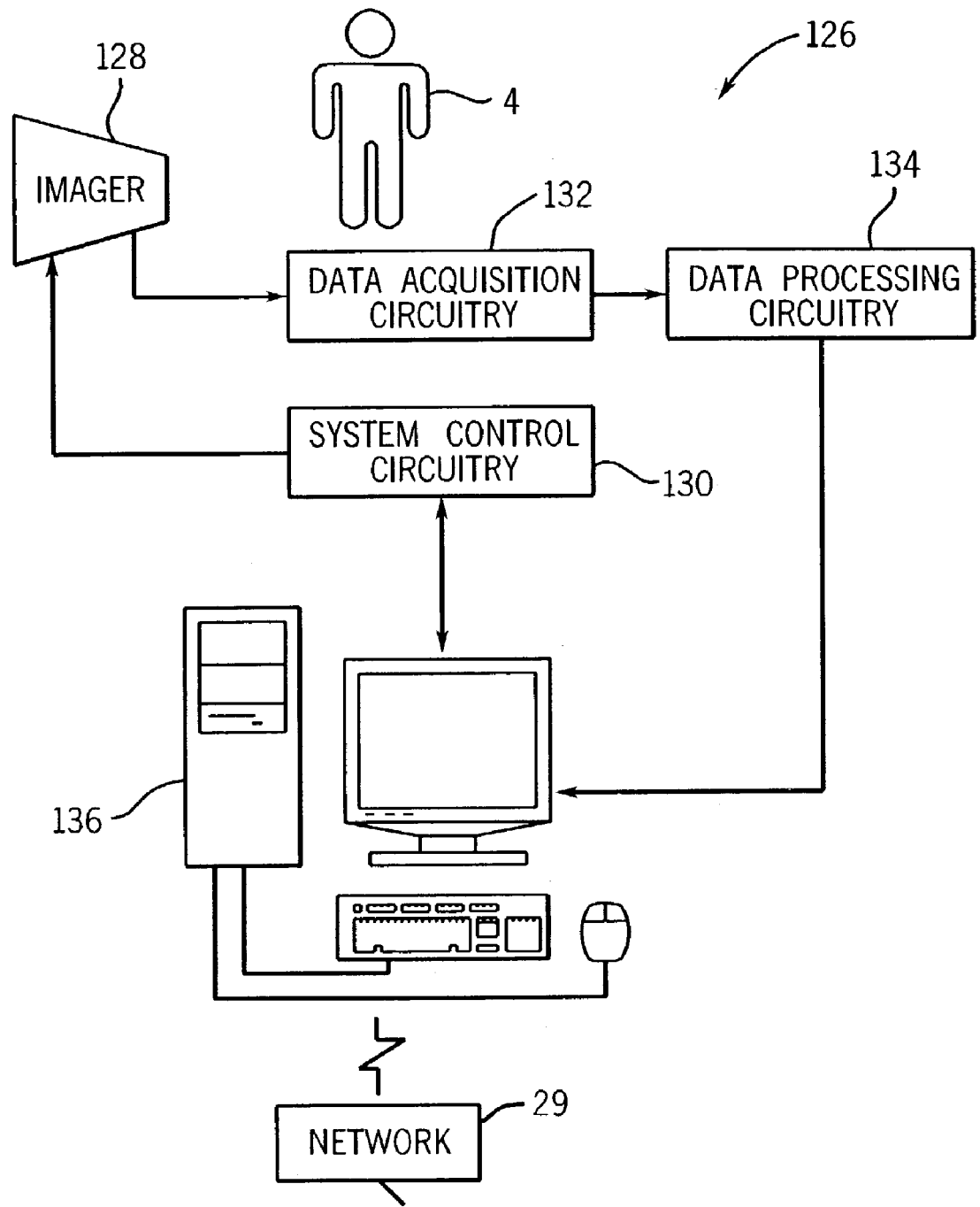
FIG. 10 is a general diagrammatical representation of certain functional components of a medical diagnostic imaging system as one of the prescribable and controllable resources mentioned in FIG. 9.

Various imaging resources may be available for diagnosing medical events and conditions in both soft and hard tissue, and for analyzing structures and function of specific anatomies. Moreover, imaging systems are available which can be used during surgical interventions, such as to assist in guiding surgical components through areas which are difficult to access or impossible to visualize. FIG. 10 provides a general overview for exemplary imaging systems, and subsequent figures offer somewhat greater detail into the major system components of specific modality systems.

Referring to FIG. 10, an imaging system 126 generally includes some type of imager 128 which detects signals and converts the signals to useful data. As described more fully below, the imager 128 may operate in accordance with various physical principles for creating the image data. In general, however, image data indicative of regions of interest in a patient are created by the imager either in a conventional support, such as photographic film, or in a digital medium.

The imager operates under the control of system control circuitry 130. The system control circuitry may include a wide range of circuits, such as radiation source control circuits, timing circuits, circuits for coordinating data acquisition in conjunction with patient or table of movements, circuits for controlling the position of radiation or other sources and of detectors, and so forth. The imager 128, following acquisition of the image data or signals, may process the signals, such as for conversion to digital values, and forwards the image data to data acquisition circuitry 132. In the case of analog media, such as photographic film, the data acquisition system may generally include supports for the film, as well as equipment for developing the film and producing hard copies that may be subsequently digitized. For digital systems, the data acquisition circuitry 132 may perform a wide range of initial processing functions, such as adjustment of digital dynamic ranges, smoothing or sharpening of data, as well as compiling of data streams and files, where desired. The data is then transferred to data processing circuitry 134 where additional processing and analysis are performed. For conventional media such as photographic film, the data processing system may apply textual information to films, as well as attach certain notes or patient-identifying information. For the various digital imaging systems available, the data processing circuitry perform substantial analyses of data, ordering of data, sharpening, smoothing, feature recognition, and so forth.

Ultimately, the image data is forwarded to some type of operator interface 136 for viewing and analysis. While operations may be performed on the image data prior to viewing, the operator interface 136 is at some point useful for viewing reconstructed images based upon the image data collected. It should be noted that in the case of photographic film, images are typically posted on light boxes or similar displays to permit radiologists and attending physicians to more easily read and annotate image sequences. The images may also be stored in short or long term storage devices, for the present purposes generally considered to be included within the interface 136, such as picture archiving communication systems. The image data can also be transferred to remote locations, such as via a network 29. It should also be noted that, from a general standpoint, the operator interface 136 affords control of the imaging system, typically through interface with the system control circuitry 130. Moreover, it should also be noted that more than a single operator interface 136 may be provided. Accordingly, an imaging scanner or station may include an interface which permits regulation of the parameters involved in the image data acquisition procedure, whereas a different operator interface may be provided for manipulating, enhancing, and viewing resulting reconstructed images.

The following is a more detailed discussion of specific imaging modalities based upon the overall system architecture outlined in FIG. 10.

X-Ray

Figure 11:
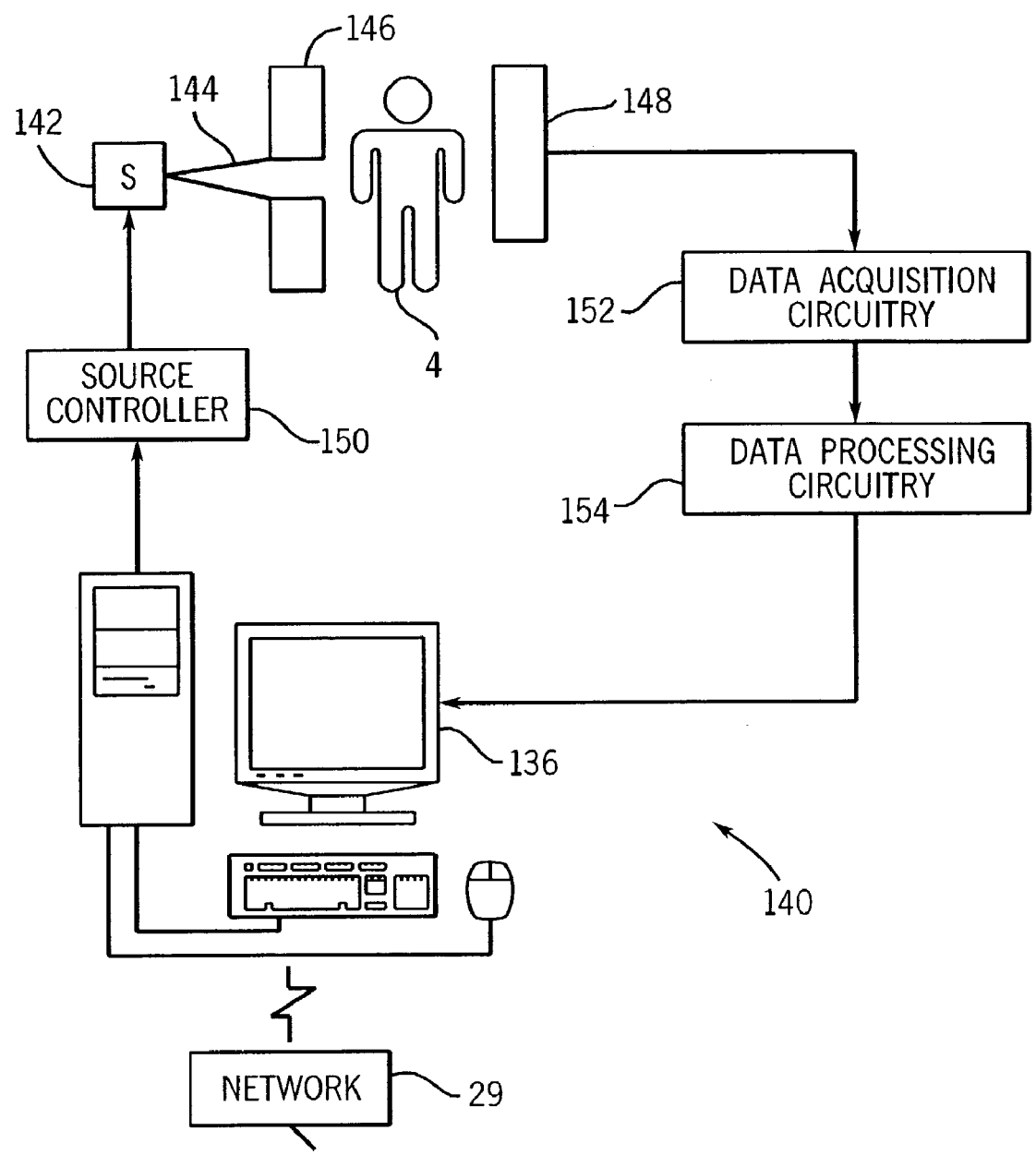
FIG. 11 is a diagrammatical representation of an exemplary X-ray imaging system which may be employed in accordance with certain aspects of the present technique.

FIG. 11 generally represents a digital X-ray system 150. It should be noted that, while reference is made in FIG. 11 to a digital system, conventional X-ray systems may, of course, be provided as controllable and prescribable resources in the present technique. In particular, conventional X-ray systems may offer extremely useful tools both in the form of photographic film, and digitized image data extracted from photographic film, such as through the use of a digitizer.

System 140 illustrated in FIG. 11 includes a radiation source 142, typically an X-ray tube, designed to emit a beam 144 of radiation. The radiation may be conditioned or adjusted, typically by adjustment of parameters of the source 142, such as the type of target, the input power level, and the filter type. The resulting radiation beam 144 is typically directed through a collimator 146 which determines the extent and shape of the beam directed toward patient 4. A portion of the patient 4 is placed in the path of beam 144, and the beam impacts a digital detector 148.

Detector 148, which typically includes a matrix of pixels, encodes intensities of radiation impacting various locations in the matrix. A scintillator converts the high energy X-ray radiation to lower energy photons which are detected by photodiodes within the detector. The X-ray radiation is attenuated by tissues within the patient, such that the pixels identify various levels of attenuation resulting in various intensity levels which will form the basis for an ultimate reconstructed image.

Control circuitry and data acquisition circuitry are provided for regulating the image acquisition process and for detecting and processing the resulting signals. In particular, in the illustration of FIG. 11, a source controller 150 is provided for regulating operation of the radiation source 142. Other control circuitry may, of course, be provided for controllable aspects of the system, such as a table position, radiation source position, and so forth. Data acquisition circuitry 152 is coupled to the detector 148 and permits readout of the charge on the photodetectors following an exposure. In general, charge on the photodetectors is depleted by the impacting radiation, and the photodetectors are recharged sequentially to measure the depletion. The readout circuitry may include circuitry for systematically reading rows and columns of the photodetectors corresponding to the pixel locations of the image matrix. The resulting signals are then digitized by the data acquisition circuitry 152 and forwarded to data processing circuitry 154.

The data processing circuitry 154 may perform a range of operations, including adjustment for offsets, gains, and the like in the digital data, as well as various imaging enhancement functions. The resulting data is then forwarded to an operator interface or storage device for short or long-term storage. The images reconstructed based upon the data may be displayed on the operator interface, or may be forwarded to other locations, such as via a network 29 for viewing. Also, digital data may be used as the basis for exposure and printing of reconstructed images on a conventional hard copy medium such as photographic film.

MR

Figure 12:
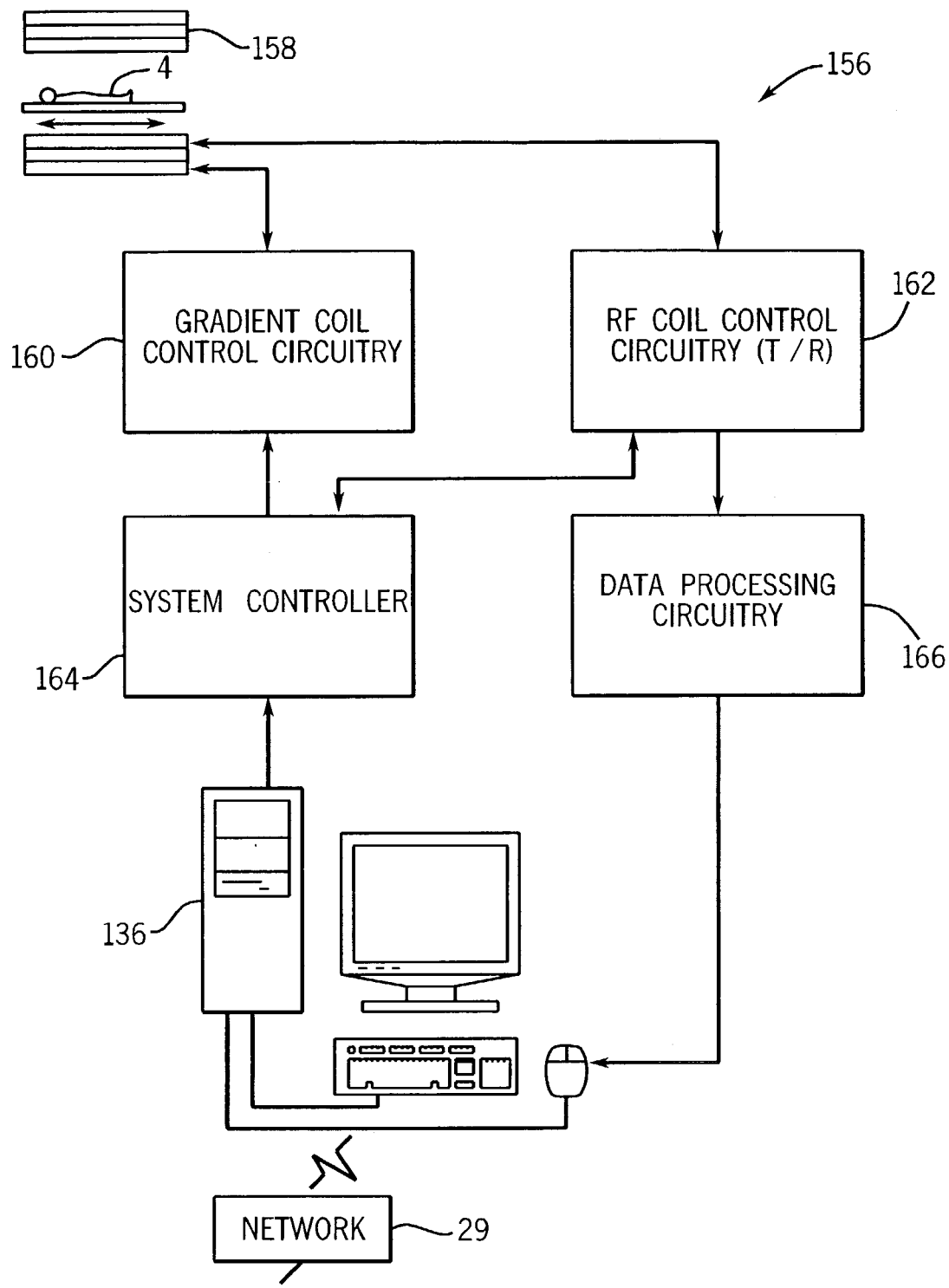
FIG. 12 is a diagrammatical representation of an exemplary magnetic resonance imaging system which may be employed in the technique.

FIG. 12 represents a general diagrammatical representation of a magnetic resonance imaging system 156. The system includes a scanner 158 in which a patient is positioned for acquisition of image data. The scanner 158 generally includes a primary magnet for generating a magnetic field which influences gyromagnetic materials within the patient's body. As the gyromagnetic material, typically water and metabolites, attempts to align with the magnetic field, gradient coils produce additional magnetic fields which are orthogonally oriented with respect to one another. The gradient fields effectively select a slice of tissue through the patient for imaging, and encode the gyromagnetic materials within the slice in accordance with phase and frequency of their rotation. A radio-frequency (RF) coil in the scanner generates high frequency pulses to excite the gyromagnetic material and, as the material attempts to realign itself with the magnetic fields, magnetic resonance signals are emitted which are collected by the radio-frequency coil.

The scanner 158 is coupled to gradient coil control circuitry 160 and to RF coil control circuitry 162. The gradient coil control circuitry permits regulation of various pulse sequences which define imaging or examination methodologies used to generate the image data. Pulse sequence descriptions implemented via the gradient coil control circuitry 160 are designed to image specific slices, anatomies, as well as to permit specific imaging of moving tissue, such as blood, and defusing materials. The pulse sequences may allow for imaging of multiple slices sequentially, such as for analysis of various organs or features, as well as for three-dimensional image reconstruction. The RF coil control circuitry 162 permits application of pulses to the RF excitation coil, and serves to receive and partially process the resulting detected MR signals. It should also be noted that a range of RF coil structures may be employed for specific anatomies and purposes. In addition, a single RF coil may be used for transmission of the RF pulses, with a different coil serving to receive the resulting signals.

The gradient and RF coil control circuitry function under the direction of a system controller 164. The system controller implements pulse sequence descriptions which define the image data acquisition process. The system controller will generally permit some amount of adaptation or configuration of the examination sequence by means of an operator interface 136.

Data processing circuitry 166 receives the detected MR signals and processes the signals to obtain data for reconstruction. In general, the data processing circuitry 166 digitizes the received signals, and performs a two-dimensional fast Fourier transform on the signals to decode specific locations in the selected slice from which the MR signals originated. The resulting information provides an indication of the intensity of MR signals originating at various locations or volume elements (voxels) in the slice. Each voxel may then be converted to a pixel intensity in image data for reconstruction. The data processing circuitry 166 may perform a wide range of other functions, such as for image enhancement, dynamic range adjustment, intensity adjustments, smoothing, sharpening, and so forth. The resulting processed image data is typically forwarded to an operator interface for viewing, as well as to short or long-term storage. As in the case of foregoing imaging systems, MR image data may be viewed locally at a scanner location, or may be transmitted to remote locations both within an institution and remote from an institution such as via a network connection 29.

CT

Figure 13:
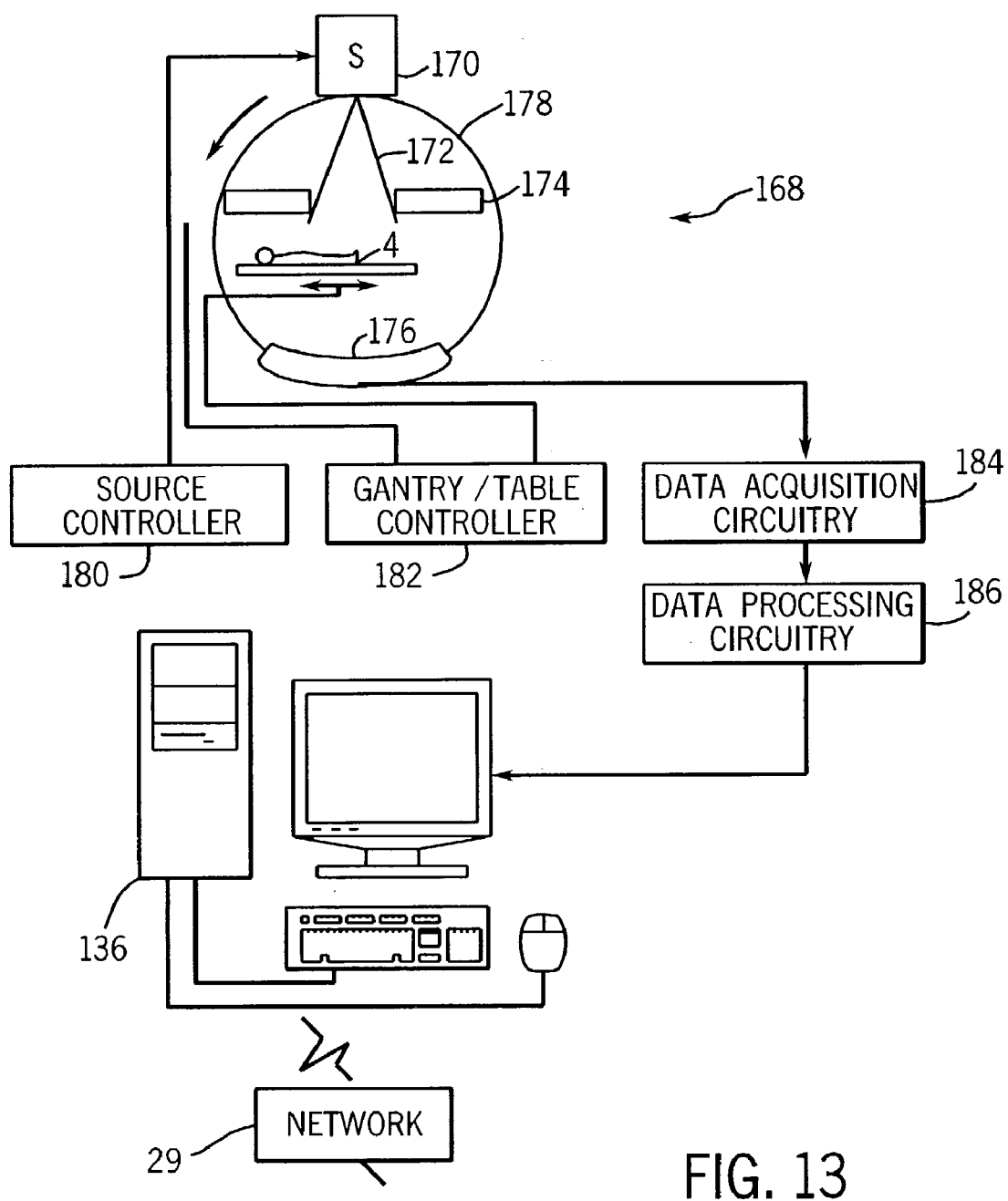
FIG. 13 is a diagrammatical representation of an exemplary computed tomography imaging system for use in the technique.

FIG. 13 illustrates the basic components of a computed tomography (CT) imaging system. The CT imaging system 168 includes a radiation source 170 which is configured to generate X-ray radiation in a fan-shaped beam 172. A collimator 174 defines limits of the radiation beam. The radiation beam 172 is directed toward a curved detector 176 made up of an array of photodiodes and transistors which permit readout of charges of the diodes depleted by impact of the radiation from the source 170. The radiation source, the collimator and the detector are mounted on a rotating gantry 178 which enables them to be rapidly rotated (such as at speeds of two rotations per second).

During an examination sequence, as the source and detector are rotated, a series of view frames are generated at angularly-displaced locations around a patient 4 positioned within the gantry. A number of view frames (e.g. between 500 and 1000) are collected for each rotation, and a number of rotations may be made, such as in a helical pattern as the patient is slowly moved along the axial direction of the system. For each view frame, data is collected from individual pixel locations of the detector to generate a large volume of discrete data. A source controller 180 regulates operation of the radiation source 170, while a gantry/table controller 182 regulates rotation of the gantry and control of movement of the patient.

Data collected by the detector is digitized and forwarded to a data acquisition circuitry 184. The data acquisition circuitry may perform initial processing of the data, such as for generation of a data file. The data file may incorporate other useful information, such as relating to cardiac cycles, positions within the system at specific times, and so forth. Data processing circuitry 186 then receives the data and performs a wide range of data manipulation and computations.

In general, data from the CT scanner can be reconstructed in a range of manners. For example, view frames for a full 360° of rotation may be used to construct an image of a slice or slab through the patient. However, because some of the information is typically redundant (imaging the same anatomies on opposite sides of a patient), reduced data sets comprising information for view frames acquired over 180° plus the angle of the radiation fan may be constructed. Alternatively, multi-sector reconstructions are utilized in which the same number of view frames may be acquired from portions of multiple rotational cycles around the patient. Reconstruction of the data into useful images then includes computations of projections of radiation on the detector and identification of relative attenuations of the data by specific locations in the patient. The raw, the partially processed, and the fully processed data may be forwarded for post-processing, storage and image reconstruction. The data may be available immediately to an operator, such as at an operator interface 136, and may be transmitted remotely via a network connection 29.

PET

Figure 14:
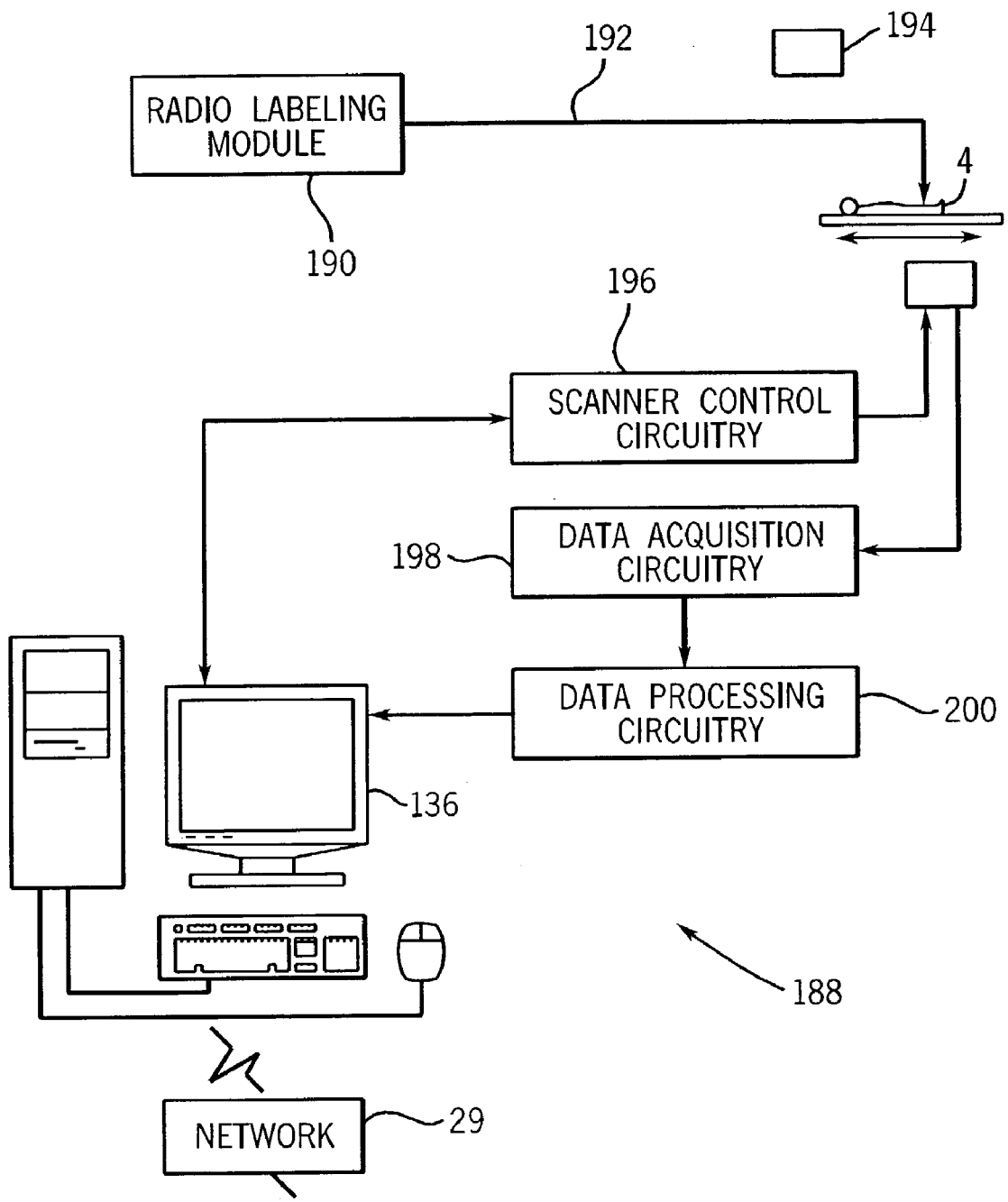
FIG. 14 is a diagrammatical representation of an exemplary positron emission tomography system for use in the technique.

FIG. 14 illustrates certain basic components of a positron emission tomography (PET) imaging system. The PET imaging system 188 includes a radio-labeling module 190 which is sometimes referred to as a cyclotron. The cyclotron is adapted to prepare certain tagged or radio-labeled materials, such as glucose, with a radioactive substance. The radioactive substance is then injected into a patient 4 as indicated at reference numeral 192. The patient is then placed in a PET scanner 194. The scanner detects emissions from the tagged substance as its radioactivity decays within the body of the patient. In particular, positrons, sometimes referred to as positive electrons, are emitted by the material as the radioactive nuclide level decays. The positrons travel short distances and eventually combine with electrons resulting in emission of a pair of gamma rays. Photomultiplier-scintillator detectors within the scanner detect the gamma rays and produce signals based upon the detected radiation.

The scanner 194 operates under the control of scanner control circuitry 196, itself regulated by an operator interface 136. In most PET scans, the entire body of the patient is scanned, and signals detected from the gamma radiation are forwarded to data acquisition circuitry 198. The particular intensity and location of the radiation can be identified by data processing circuitry 200, and reconstructed images may be formulated and viewed on operator interface 136, or the raw or processed data may be stored for later image enhancement, analysis, and viewing. The images, or image data, may also be transmitted to remote locations via a network link 29.

PET scans are typically used to detect cancers and to examine the effects of cancer therapy. The scans may also be used to determine blood flow, such as to the heart, and may be used to evaluate signs of coronary artery disease. Combined with a myocardial metabolism study, PET scans may be used to differentiate non-functioning heart muscle from heart muscle that would benefit from a procedure, such as angioplasty or coronary artery bypass surgery, to establish adequate blood flow. PET scans of the brain may also be used to evaluate patients with memory disorders of undetermined causes, to evaluate the potential for the presence of brain tumors, and to analyze potential causes for seizure disorders. In these various procedures, the PET image is generated based upon the differential uptake of the tagged materials by different types of tissue.

Fluorography

Fluoroscopic or fluorography systems consist of X-ray image intensifiers coupled to photographic and video cameras. In digital systems, the basic fluoroscopic system may be essentially similar to that described above with reference to FIG. 11. In simple systems, for example, an image intensifier with a video camera may display images on a video monitor, while more complex systems might include high resolution photographic cameras for producing still images and cameras of different resolutions for producing dynamic images. Digital detectors such as those used on digital X-ray systems are also used in such fluoroscopic systems. The collected data may be recorded for later reconstruction into a moving picture-type display. Such techniques are sometimes referred to as cine-fluorography. Such procedures are widely used in cardiac studies, such as to record movement of a living heart. Again, the studies may be performed for later reference, or may also be performed during an actual real-time surgical intervention.

As in conventional X-ray systems, the camera used for fluorography systems receives a video signal which is collected by a video monitor for immediate display. A video tape or disk recorder may be used for storage and later playback. The computer system or data processing circuitry may perform additional processing and analysis on the image data both in real-time and subsequently.

The various techniques used in fluorography systems may be referred to as video-fluoroscopy or screening, and digital fluorography. The latter technique is replacing many conventional photography-based methods and is sometimes referred to as digital spot imaging (DSI), digital cardiac imaging (DCI) and digital vascular imaging (DVI)/digital subtraction angiography (DSA), depending upon the particular clinical application. A hard-copy device, such as a laser imager, is used for to output hard copies of digital images. Moreover, fluoroscopic techniques may be used in conjunction with conventional X-ray techniques, particularly where a digital X-ray detector is employed as described above. That is, high-energy X-ray images may be taken at intervals interspersed with fluoroscopic images, the X-ray images providing a higher resolution or clarity in the images, while the fluoroscopic images provide real-time movement views.

Mammography

Mammography generally refers to specific types of imaging, commonly using low-dose X-ray systems and high-contrast, high-resolution film, or digital X-ray systems as described above, for examination of the breasts. Other mammography systems may employ CT imaging systems of the type described above, collecting sets of information which are used to reconstruct useful images. A typical mammography unit includes a source of X-ray radiation, such as a conventional X-ray tube, which may be adapted for various emission levels and filtration of radiation. An X-ray film or digital detector is placed in an oppose location from the radiation source, and the breast is compressed by plates disposed between these components to enhance the coverage and to aid in localizing features or abnormalities detectable in the reconstructed images. In general, the features of interest, which may include such anatomical features as microcalcifications, various bodies and lesions, and so forth, are visible in the collected data or on the exposed film due to differential absorption or attenuation of the X-ray radiation as compared to surrounding tissues. Mammography plays a central role in the early detection of cancers which can be more successfully treated when detected at very early stages.

Sonography

Sonography imaging techniques generally include ultrasonography, employing high-frequency sound waves rather than ionizing or other types of radiation. The systems include a probe which is placed immediately adjacent to a patient's skin on which a gel is disposed to facilitate transmission of the sound waves and reception of reflections. Reflections of the sound beam from tissue planes and structures with differing acoustic properties are detected and processed. Brightness levels in the resulting data are indicative of the intensity of the reflected sound waves.

Ultrasonography is generally performed in real-time with a continuous display of the image on a video monitor. Freeze-frame images may be captured, such as to document views displayed during the real-time study. In ultrasound systems, as in conventional radiography systems, the appearance of structures is highly dependent upon their composition. For example, water-filled structures (such as a cyst) appear dark in the resulting reconstructed images, while fat-containing structures generally appear brighter. Calcifications, such as gallstones, appear bright and produce a characteristic shadowing artifact.

When interpreting ultrasound studies, radiologists and clinicians generally use the terminology "echogeneity" to describe the brightness of an object. A "hypoechoic" structure appears dark in the reconstructed image, while a "hyperechoic" structure appears bright.

Ultrasonography presents certain advantages over other imaging techniques, such as the absence of ionizing radiation, the high degree of portability of the systems, and their relatively low cost. In particular, ultrasound examinations can be performed at a bedside or in an emergency department by use of a mobile system. The systems are also excellent at distinguishing whether objects are solid or cystic. As with other imaging systems, results of ultrasonography may be viewed immediately, or may be stored for later viewing, transmission to remote locations, and analysis.

Infrared

Clinical thermography, otherwise known as infrared imaging, is based upon a careful analysis of skin surface temperatures as a reflection of normal or abnormal human physiology. The procedure is commonly performed either by the direct application of liquid crystal plates to a part of the body, or via ultra-sensitive infrared cameras through a sophisticated computer interface. Each procedure extrapolates the thermal data and forms an image which may be evaluated for signs of possible disease or injury. Differences in the surface temperature of the body may be indicative of abnormally enhanced blood flow, for example, resulting from injury or damage to underlying tissues.

Nuclear

Nuclear medicine involves the administration of small amounts of radioactive substances and the subsequent recording of radiation emitted from the patient at specific loci where the substances accumulate. There are a wide variety of diagnostic and therapeutic applications of nuclear medicine. In general, nuclear medicine is based upon the spontaneous emission of energy in the form of radiation from specific types of nuclei. The radiation typically takes the form of alpha beta and gamma rays. The nuclei are used in radiopharmaceuticals as tracers which can be detected for imaging, or whose radiation can serve for treatment purposes.

A tracer is a substance that emits radiation and can be identified when placed in the human body. Because the tracers can be absorbed differently by different tissues, their emissions, once sensed and appropriately located in the body, can be used to image organs, and various internal tissues. Radiopharmaceuticals are typically administered orally or intravenously, and tend to localize in specific organs or tissues. Scanning instruments detect the radiation produced by the radiopharmaceuticals and images can be reconstructed based upon the detected signals. Radioactive analysis of biologic specimens may also be performed by combining samples from the patient, such as blood or urine, with radioactive materials to measure various constituents of the samples.

In treatment, radioactive materials may be employed due to the emissions they produce in specific tissues in which they are absorbed. Radioactive iodine, for example, may be trapped within cancerous tissue without excessive radiation to surrounding healthy tissue. Such compounds are used in various types of treatment, such as for thyroid cancer. Because the iodine tends to pass directly to the thyroid, small doses of radioactive iodine are absorbed in the gland for treatment or diagnostic purposes. For diagnosis, a radiologists may determine whether too little or too much iodine is absorbed, providing an indication of hypothyroidism or hyperthyroidism, respectively.

Other types of imaging in nuclear medicine may involve the use of other compounds. Technetium, for example, is a radiopharmaceutical substance which is combined with a patient's white blood cells, and may be used to identify metastasis or spread of cancer in the bone. Following a period of settling, scans of specific limbs or of the entire body may be performed to identify whether metastasis can be diagnosed. Technetium may also be used to identify abnormalities in the liver or gallbladder, such as blockages due to gallstones. The substances also used in radionuclide ventriculograms. In such procedures, a sample of the patient's blood is removed (such as approximately 10 $cm^3$) and radioactive technetium is chemically attached to the red blood cells. The blood is then injected back into the patient, and its circulation through the heart is traced and imaged.

Other uses for technetium in nuclear medicine include the diagnosis of appendicitis, due to the inflammation which occurs and the presence of white blood cells in the organ. Similarly, techniques involving technetium may be used for the diagnosis of abdominal inflammations and infections.

In radiation oncology known or possible extents tumors may be determined, and radiation employed to attack tumorous cells while avoiding major injury to surrounding healthy cells. External beam therapy, for example, involves radiation from a linear accelerator, betatron or cobalt machine that is targeted to destroy cancers at known locations. In brachytherapy, radioactive sources such as iodine, cesium or iridium are combined into or alongside a tumor. In another cancer therapy, known as boron neutron capture therapy (MNCT), alpha particles are produced by non-radioactive pharmaceuticals containing boron. Subsequent neutron beam irradiation causes neutrons to react with the boron in a tumor to generate alpha particles that aide in destroying the tumor.

Radioactive nuclides can be naturally-occurring or may be produced in reactors, cyclotrons, generators, and so forth. For radiation therapy, oncology, or other applications in nuclear medicine, radiopharmaceuticals are artificially produced. The radiopharmaceuticals have relatively short half-lives, such that they may be employed for their intended purpose, and degrade relatively rapidly to non-toxic substances.

Thermoacoustic

Thermoacoustic imaging systems are based upon application of short pulses of energy to specific tissues. The energy is created and applied to cause portions of the energy to be absorbed by a patient's tissue. Due to heating of the tissue, the tissue is caused to expand and an acoustic wave is thereby generated. Multi-dimensional image data can be obtained which is related to the energy absorption of the tissue. The energy may be applied in short pulses of radio-frequency (RF) waves. The resulting thermoacoustic emissions are then detected with an array of ultrasonic detectors (transducers).

Thermoacoustic scanners consist generally of an imaging tank, a multi-channel amplifier and an RF generator. The generator and the other components of the scanner are generally positioned in an RF-shielded room or environment. A digital acquisition system is provided along with a rotational motor for acquiring the thermoacoustic emission signals. A processing system then filters the signals, and processes them in digital form for image reconstruction. In general, the image contrast is determined by the energy delivered to the patient, and image spatial resolution is determined by the sound propagation properties and the detector geometry.

Clinical Laboratory Resources

Clinical laboratory resources include various techniques which analyze tissues of the body. Many of the resources are based upon extraction and analysis of fluids from different parts of the body, and comparison of detectable parameters of the fluids with norms for the individual patient or for a population of patients. The procedures for clinical laboratories analysis include sampling of the fluids or tissues, typically during a hospital or clinic visit. Such tissue collection may include various sampling procedures, such as to collect blood, saliva, urine, cerebrospinal fluid (CSF), and so forth. The tissues are collected and stored in specially prepared containers and forwarded to a laboratory for testing analysis.

Many different methods exist for performing clinical laboratory tests on body fluids and tissues. Some such techniques involve mixing of antibodies or antigens with the tissues being tested. The antibodies essentially consist of special proteins made by the immune system. The body produces such proteins in response to certain types of infection or the presence of foreign materials or organisms in the body. Antigens are substances which cause immune system responses in the body. Such antigens include bacteria, virus, medications, or other tissues, including, in certain circumstances, tissues of a patient's own body.

In general, where antibodies in the blood, for example, are to be detected, antigens are typically used in tests and analysis. Where the presence of antigens is to be detected, conversely, antibodies may be used. By way of example, analysis for the presence of lyme disease may be based upon placement of portions of a bacteria that causes lime disease, the antigen, in a container along with samples of a patient's blood. If antibodies against lyme disease bacteria a present, these will react with antigen and may be detected in various ways. A positive reaction would indicate that the disease may be present, whereas a negative reaction indicates that the disease is probably not present.

Blood

A complete blood count (CBC) provides important information regarding the types and numbers of cells in the blood. In general, the blood contains many components including red blood cells, white blood cells and platelets. The CBC assists physicians in evaluating symptoms, such as weakness, fatigue, bruising and to diagnose specific disease states and medical events, such as anemia, infection and many other common disorders.

CBC and other blood tests may target specific parameters of the blood constituency. In particular, such tests may serve to identify white blood cell count, red blood cell count, hematocrit, hemoglobin, various red blood cell indices, platelet count, and other blood chemistry measurements. The resulting indications, typically in the form of levels or ranges, are then compared to known normal or abnormal levels and ranges as an indication of health or potential disease states. Over time, the comparisons may be based upon the patient's own normal or abnormal levels as an indication of progression of disease or the results of treatment or the bodies own reaction to infection or other medical events.

The specific types of measurements made in blood analysis may be indicative of wide range of medical conditions. For example, elevated white blood count levels may be an indication of infection or the body's response to certain types of treatment, such as cancer treatment. The white blood cells may be differentiated from one another to identify major types of white blood cells, including neutrophils, lymphocytes, monocytes, eosinophils, and basophils. Each of these types of cells plays a different role in response by the body. The numbers of each of these white blood cell types may provide important information into the immune system and the immune response. Thus, levels and changes in the white blood cell counts can identify infection, allergic or toxic reactions, as well as other specific conditions.

Analysis of red blood cells serves numerous purposes. For example, because the red blood cells provide exchange of oxygen in carbon dioxide for tissues, their relative count may provide an indication of whether sufficient oxygen is being provided to the body, or, if elevated, whether there is a risk of polycythemia, a condition that can lead to clumping and blocking of capillaries. Hematocrit measures the volume occupied by red blood cells in the blood. The hematocrit value is generally provided as a percentage of the red blood cells in a volume of blood. Hemoglobin tests measure the relative amount of hemoglobin in the blood, and provide indication of the blood's ability to carry oxygen throughout the body. Other red blood indices include mean corpuscular volume, mean corpuscular hemoglobin, and mean corpuscular hemoglobin concentration. These indices are generally determined during other measurements of the CBC, and provide indications of the relative sizes of red blood cells, the hemoglobin content of the cells, and the concentration of hemoglobin in an average blood cell. Such measurements may be used, for example, to identify different types of anemia.

The platelet or thrombocyte count provides an indication of the relative levels of platelets in the blood, and may be used to indicate abnormalities in blood clotting and bleeding.

In addition to the foregoing analyses, blood smear examinations may be performed, in which blood is smeared and dyed for manual or automated visual inspection. The counts and types of cells contained in the blood may ascertained from such examination, including the identification of various abnormal cell types. Moreover, large variety of chemical compositions may be detected and analyzed in blood tests, including levels of albumin, alkaline, phosphatase, ALT (SGPT), AST (SGOT), BUN, calcium-serum, serum chloride, carbon dioxide, creatinine, direct bilirubin, gamma-GT glucose, LDH, phosphorous-serum, potassium, serum sodium, total bilirubin, total cholesterol, total protein, uric acid, and so forth.

Blood testing is also used to identify the presence or changes in levels of tumor biomarkers. For example, the presence of cancers such as colon, prostate, and liver cancer are directly linked to elevated blood levels of specific biomarkers, such as carcinogenic embryonic antigen (CEA), prostate specific antigen (PSA), and alpha-fetoprotein (AFP), respectively, which can be detected by enzyme-linked immunosorbent assay (ELISA) tests, as discussed more fully below.

Urine

A wide variety of analysis may be performed on urine samples. Certain of these analyses based upon the overall appearance and characteristics of the sample, while others are based upon chemical or microscopic analysis. Of the analyses which are based on macroscopic features of urine samples, are tests of color, clarity, odor, specific gravity, and pH.

Factors affecting color of urine samples include fluid balance, diet, medications, and disease states. Color may be, for example, an indication of the presence of blood in the urine, indicative of conditions such as kidney ailments. The relative clarity (i.e. opacity or turbidity) of the urine may be an indication of the presence of bacteria, blood, sperm, crystals or mucus that, in turn, may be indicative of abnormal physical conditions. Certain disease states or physical conditions can also lead to abnormal odors which can be detected in the blood, such as E. coli. The specific gravity of the urine provides and indication of relative amounts of substances dissolved in the sample. In general, higher specific gravities may be indicative of higher levels of solid materials dissolved in the urine, and may provide an indication of the state of functioning of the kidneys. The pH of the sample (i.e. acidity and alkalinity) of the sample may be an indication of kidney conditions and kidney function. For example, urine pH may be adjusted by treatment, such as to prevent formation of certain types of kidney stones.

Chemical analyses of urine samples may be performed to provide indications of such constituents as proteins, glucose and ketones. The presence of proteins in the blood, can be an indication of certain physical conditions and states, such as fever, normal pregnancy, as well as diseases such as kidney disorders. Glucose, which is normally found in the blood, is generally not present in the urine. The presence of glucose in urine samples can be an indication of diabetes or certain kidney damage or disease. Ketones, a by-product of the metabolization of fat, are normally present in the urine. However, high ketone levels can signal conditions such as diabetic ketoacidosis. Other abnormal conditions, such as low sugar and starch diets, starvation, and prolonged vomiting can also cause elevated ketone levels in the urine.

Microscopic analysis of urine samples can be used to detect the presence of a variety of materials, including red and white blood cells, casts, crystals, bacteria, yeast cells and parasites. Such solid materials are generally identified by placing the urine sample in a centrifuge to cause the materials to form sediments. Casts and crystals may be signs of abnormal kidney function, while the presence of bacteria, yeast cells or parasites can indicate the presence of various types of infection.

Saliva

Analyses of saliva can serve a number of clinical purposes. For example, sex hormone testing may be performed by different methods including saliva and serum. The sex hormones typically tested include estradiol, estrone, estriol, testosterone, progesterone, DHEA, melatonin, and cortisol. In using the saliva testing, the free fraction of hormones is calculated to arrive at a baseline value. Saliva reflects the biological active (free) fraction of steroids in the bloodstream (unlike blood or urine which measures total levels). The free fraction of hormones can easily pass from the blood into the salivary glands. A drop in the free fraction of sex steroid hormones specifically leads to perimenopause and menopause. Such tests may be performed, for example, to determine whether hormone replacement therapy should be considered to bring hormone levels and balance from current levels back into the protective range.

Saliva testing is also used to identify the presence or changes in levels of tumor biomarkers. For example, the presence of breast malignancies in women is directly linked to elevated levels of c-erbB-2 in saliva, which can be detected by enzyme-linked immunosorbent assay (ELISA) tests, as discussed more fully below.

Similarly, sputum-based tests can be used in the diagnosis of disease states, such as lung cancer. Such diagnosis is based upon the fact that cancer cells may be present in fluid a patient expels from the airways. In a typical implementation, clinicians analyze sputum samples as a screening tool by determining whether the samples contain atypical cells from the lungs before they develop into cancer cells.

Gastrointestinal Fluids

The analysis of gastrointestinal fluids can similarly be important in detecting and diagnosing certain disease states or abnormalities in function of various internal organs. For example, liver function tests (LFTs) afford detection of both primary and secondary liver diseases, although the tests are generally not specific. That is, the results must be intelligently selected and interpreted to provide the maximum useful information. Indeed, certain of the common tests may be characterized as functional tests rather than tests for diseases.

In one exemplary test, bilirubin is sampled and analyzed. Bilirubin results from breakdown of hemoglobin molecules by the reticuloendothelial system. Bilirubin is carried in plasma to the liver, where it is extracted by hepatic parenchymal cells, conjugated with two glucuronide molecules to form bilirubin diglucuronide, and excreted in the bile. Bilirubin can be measured in the serum as total bilirubin, including both conjugated and unconjugated bilirubin, and as direct bilirubin which is conjugated bilirubin. Abnormal conditions, such as hemolysis can cause increased formation of unconjugated bilirubin, which can rise to levels that cannot be properly processed by the liver. Moreover, obstructive jaundice may result from extrahepatic common bile duct obstruction by stones or cancer, as evidenced by an increase in serum bilirubin. Long term obstruction may result in secondary liver damage. Jaundice due to liver cell damage, such as is found in hepatitis or decompensated active cirrhosis, can also be evidenced by elevated levels of bilirubin.

As a further example, analysis of the enzyme alkaline phosphatase may provide an indication of liver damage. The enzyme mainly produced in liver and bone, and is very sensitive to partial or mild degrees of biliary obstruction. In such circumstances, alkaline phosphatase levels may be elevated with a normal serum bilirubin. While little or no elevation may be present in mild cases of acute liver cell damage, in cirrhosis, the alkaline phosphatase may vary depending upon the degree of compensation and obstruction. Moreover, different isoenzymes of alkaline phosphatase are found in liver and bone, which may be used to provide an indication of the source of elevated serum alkaline phosphatase.

Aspartate aminotransferase (AST) is an enzyme found in several organs, especially in heart, skeletal muscle, and liver. Damage to hepatocytes releases AST, and in cases of acute hepatitis, AST levels are usually elevated according to the severity and extent of hepatocyte damage at the particular time the specimen is drawn. In conditions such as passive congestion of the liver, variable degrees of AST elevation may be detected, especially if the episode is severe and acute.

Similarly, alanine aminotransferase (ALT) is an enzyme found mostly, although not exclusively, in the liver. In liver disease, ALT is elevated in roughly the same circumstances as the AST, although ALT appears somewhat less sensitive to the concitoin, except with more extensive or severe acute parenchymal damage. An advantage of ALT analysis is that it is relatively specific for liver cell damage.

A number of other constituents of gastrointestinal fluids may provide similar indications of abnormal conditions and disease states. For example, lactate dehydrogenase, although somewhat less sensitive than AST, may provide an indication of liver damage or hepatitis. Gamma glutamyl transpeptidase is another enzyme found primarily in the liver and kidney, and may be elevated in a wide variety of hepatic diseases. Serum proteins, such as albumin are synthesized chiefly in the liver, and acute or chronic destructive liver diseases of at least moderate severity show decreased serum albumin on electrophoresis. Similarly, coagulation factors are synthesized in the liver, so that certain coagulation tests (such as the prothrombin time or PT) are relatively sensitive indicators of hepatic function. Elevated levels of AMM (ammonia) may occur with liver dysfunction, hepatic failure, erythroblastosis fetalis, cor pulmonale, pulmonary emphysma, congestive heart failure and exercise. Decreased levels may occur with renal failure, essential or malignant hypertension or with the use of certain antibiotics (e.g. neomycin, tetracycline). Further, hepatitis-associated antigen (HAA) may aid in the diagnosis of hepatitis A, B, non-A and non-B, tracking recovery from hepatitis and to identify hepatitis "carriers." Immunoglobulin G (IgG) level is used in the diagnosis and treatment of immune deficiency states, protein-losing conditions, liver disease, chronic infections, as well as specific diseases such as multiple sclerosis, mumps, meningitis, while immunoglobulin M (IgM) levels are used in the diagnosis and treatment of immune deficiency states, protein-losing conditions, Waldenstrom's Macroglobinema, chronic infections and liver disease. Other constituents which may be analyzed include alkaline phosphatase, used, for example, to distinguish between liver and bone disease, and in the diagnosis and treatment of parathyroid and intestinal diseases, leucine amiopeptidase, used to diagnose liver disorders, amylase, used to diagnose pancreatitis and disorders affecting salivary glands, liver, intestines, kidney and the female genital tract, and lipase, used to diagnose pancreatitis and pancreatic carcinoma.

Reproductive Fluids

A number of tests may be performed on reproductive fluids to evaluate the function of the reproductive system, as well as disease states or abnormal function due to a wide variety of events and conditions including disease, trauma, and aging. Among the many tests available, are cervical mucus tests, designed to evaluate infertility by predicting the day of ovulation and determining whether ovulation occurs. Similarly, semen analyses are commonly performed to assess male fertility and document adequate sterilization after a vasectomy by checking for abnormal volume, density, motility and morphology which can indicate infertility. The Papanicolaou smear test (commonly referred to as a Pap Smear, Pap Test, or Cytologic Test for Cancer) is used to detect neoplastic cells in cervical and vaginal secretions or to follow certain abnormalities (e.g. infertility).

Specific tests or analyses of reproductive fluids may be directed to corresponding specific disease states. For example, gonorrhea cultures are used to diagnose gonorrhea, while chlamydia smears are used to diagnose chlamydia infections, indicated if a gram stain of the smear exhibits polymorphonuclear leukocytes.

Cerebrospinal Fluids

Cerebrospinal fluids are the normally clear, colorless fluids that surround the brain and spinal cord. Cerebrospinal fluids are typically analyzed to detect the presence of various infectious organisms. The fluid is generally collected by performing a lumbar puncture, also called a spinal tap. In this procedure, a needle is inserted into the spinal canal to obtain a sample of the cerebrospinal fluid. The pressure of cerebrospinal fluid is measured during a lumbar puncture. Samples are then collected and later analyzed for color, blood cell counts, protein, glucose, and other substances. A sample of the fluid may be used for various cultures that promote the growth of infectious organisms, such as bacteria or fungi, to check for infection.

PCR

Polymerase chain reaction refers generally to a method of detecting and amplifying specific DNA or RNA sequences. Typically, certain known genetic regions are targeted in clinical applications, although a number of entire genomes have been and continue to be sequences for research and clinical purposes. In general, particular genes, which may be the root of abnormal conditions, disease states, or predispositions for development of particular conditions, exhibit unique sequences of constituent molecules. Moreover, infectious organisms, including viruses and bacteria, possess specific DNA or RNA sequences that are unique to the particular species or class of organism. These can be detected by such targeted sequences.

The PCR technique is utilized to produce large amounts of a specific nucleic acid sequence (DNA/RNA) in a series of simple temperature-mediated enzymatic and molecular reactions. Beginning with a single molecule of the genetic material, over a billion similar copies can be synthesized. By testing for the presence or absence of the unique sequence in a clinical specimen, PCR can be used for a great many purposes, such as to diagnose certain viral infections. PCR has also been used as one of the methods to quantify the amount of viral material in a clinical specimen. The technique may also be used for forensic purposes, for analyzing paternity and lineages, and so forth. Moreover, PCR assays are available for diagnostic, quantitative, and research purposes for a variety of viruses and viral diseases.

Gene Markers

As an outgrowth of genetic testing and genomic sequencing, increasing reference to gene markers has permitted very specific predispositions to conditions and diseases to be evaluated. The Human Genome Project has significantly advanced the understanding of the specific genetic material and sequences making up the human genome, including an estimated 50,000 to 100,000 genes as well as the spaces between them. The resulting maps, once refined and considered in conjunction with data indicative of the function of individual and groups of genes, may serve to evaluate both existing, past and possible future conditions of a patient.

While several approaches exist for genetic mapping, in general, scientists first look for easily identifiable gene markers, including known DNA segments that are located near a gene associated with a known disease or condition, and consistently inherited by persons with the disease but are not found in relatives who are disease free. Research then targets the exact location of the altered gene or genes and attempts to characterize the specific base changes. Maps of the gene markers are then developed that depict the order in which genes and other DNA landmarks are found along the chromosomes.

Even before the exact location of a mutation is known, probes can sometimes be made for reliable gene markers. Such probes may consist of a length of single-stranded DNA that is linked to a radioactive molecule and matches an area near a gene of interest. The probe binds to the area, and radioactive signals from the probe are then made visible on X-ray film, showing where the probe and the DNA match.

Predictive gene tests based upon probes and markers will become increasingly important in diagnosis of gene-linked diseases and conditions. Predictive gene tests are already available for some two dozen disorders, including life-threatening diseases such as cystic fibrosis and Tay Sachs disease. Genes also have been found to be related to several types of cancer, and tests for several rare cancers are already in clinical use. More recently, scientists have identified gene mutations that are linked to an inherited tendency toward developing common cancers, including colon cancer and breast cancer. In general, it should be noted that such gene markers and tests do not generally guarantee that a future conditions may develop, but merely provide an indication (albeit perhaps strongly linked) that a particular sequence or mutation exists.

Radioimmunoassay

Radioimmunoassays (RIA) is a technique used to detect small amounts of antibodies (Abs) or antigens (Ags), and interactions or reactions between these. The Abs or Ags are labeled with a radioisotope, such as iodine-125, and the presence of the antibodies or antigens may then be detected via a gamma counter. In a typical procedure, an Ab is bound to a hormone attached to a filter. A serum sample is added and any hormone (Ag) is allowed time to bind to the Ab. To detect the binding, a radiolabeled hormone is added and allowed time to bind. All unbound substances are washed away. The amount of bound radio activity is measured in the gamma counter. Because the presence of the hormone in the serum sample inhibits binding of the radiolabeled hormone, the amount of radio activity present in the test is inversely proportional to the amount of hormone in the serum sample. A standard curve using increasing amounts of known concentrations of the hormone is used to determine the quantity in the sample.

RIAs may be used to detect quite small quantities of Ag or Ab, and are therefore used to measure quantities of hormones or drugs present in a patient's serum. RIAs may also be performed in solution rather than on filters. In certain cases, RIAs are replaced by enzym-linked immunosorbent assays (ELISAs) or fluorescence polarization immunoassays (FPIAs). Such assays have similar sensitivities. FPIAs are highly quantitative, and leases can be appropriately designed to be similarly quantitative. RIAs can also be used to measure quantity of serum IgE antibodies specific for various allergens, in which case the assays may be referred to as radioallergosorbent tests (RAST).

ELISAs employ enzymes to detect binding of Ag and Ab. The enzyme converts a colorless substance called chromogen to a colored product indicating Ag/Ab binding. Preparation protocols may differ based upon whether Abs or Ags are to be detected. In general, the combination of Ag and Ab is attached to a surface, and a sample being tested is added and allowed to incubate. An antiglobulin or a second Ab that is covalently attached to an enzyme is added and allowed to incubate, and the unbound antiglobulins or enzyme-linked Abs are washed from the surface. A colorless substrate of the enzyme is added and, if the enzyme-linked substance is on the surface, the enzyme will be converted to a colored product for detection.

Variations on the ELISA technique include competitive ELISA, in which Abs in a sample will bind to an Ag and then inhibit binding of an enzyme-linked Ab that reacts with the Ag, and quantitative ELISAs, in which intensities of color changes that are roughly proportional to the degree of positivity of the sample are quantified.

Chromatography

Chromatography includes a broad range of techniques used to separate or analyze complex mixtures by separating them into a stationery phase bed and a mobile phase which percolates through the stationery bed. In such techniques, the components are past through a chromatography device at different rates. The rates of migration over absorptive materials provide the desired separation. In general, the smaller the affinity a molecule has for the stationery phase, the shorter the time spent in a separation column.

Benefits of chromatography include the ability to separate complex mixtures with high degrees of precision, including separation of very similar components, such as proteins differing by single amino acids. The techniques can thus be used to purify soluble or volatile substances, or for measurement purposes. Chromatography may also be employed to separate delicate products due to the conditions under which the products are separated.

Chromatographic separation takes place within a chromatography column, typically made of glass or metal. The column is formed of either a packed bed or a tubular structure. A packed bed column contains particles which make up the stationary phase. Open tubular columns may be lined with a thin filmed stationary phase. The center of the column is hollow. The mobile phase is typically a solvent moving through the column which carries the mixture to be separated. The stationary phase is typically a viscous liquid coded on the surface of solid particles which are packed into the column, although solid particles may also be taken as the stationary phase. Partitioning of solutes between the stationery and mobile phases renders the desired separations.

Several types of chromatography exist and may be employed for medical data collection purposes. In general, these types include adsorption chromatography, partition chromatography, ion exchange chromatography, molecular exclusion chromatography and affinity chromatography.

Receptor Assays

Neurons transmit impulses based upon an electrical phenomenon in which the nerve fibers are sequentially polarized and depolarized. In general, a potential across a cell boundary, typically of approximately 80 mv, results from concentrations of potassium ions within the neuron and sodium ions external to the neuron. When a stimulus is applied to the cells, a change in potential results, resulting in a flow of ions in depolarization. Neurotransmitters then cross the synaptic cleft and propagate the neural impulse.

Assays have been designed to determine the presence or absence of substances, including neurotransmitters, toxins, and so forth, which can provoke the nerve response. In general, such assays are used to measure the presence of chemicals which provoke responses of particular interest. By way of example, domoic acid receptor binding assays can be used to identify substances which bind to a glutamate receptor in the brain.

In the case of the domoic acid receptor binding assay, for example, a cainic acid preparation is made that includes a radioactive marker, such as $^3$H. By allowing the radioactive cainic acid to attach to cells containing glutamate receptors, radioactivity present in cells which may bind the cainic acid (which functions in a manner similar to glutamic acid (a common amino acid neurotransmitter) as well as domoic acid can be measured. In practice, a standard curve is typically generated based upon addition of a known amount of domoic acid to the cells, and this standard curve is then employed to estimate the concentrations of the assayed substance in a prepared sample.

Histologic Data Resources

Tissue Analysis

Histology is the microscopic study of the structure and behavior of tissue. It is classified into two categories based on the living state of the specimen under study: non-living and living specimens. The first category is the traditional study of a nonliving specimen. Many different methods may be used in preparing a specimen for study, usually dictated by the type of tissue being studied. Some common preparation methods are: a thinly sliced section on a glass slide or metal grid, a smear on a glass slide; a sheet of tissue stretched thinly; and fibers that have been separated from a strand. Some common specimen types on which these methods are used include tissue of an organ, blood, urine, mucus, areolar connective tissue, and muscle.

Most of the preparation methods for non-living specimens are fairly straightforward, while the actual method used to prepare a section can be quite involved. The specimen must first be preserved to prevent decay, preserve the cellular structure, and intensify later staining. The specimen is generally either be frozen or imbedded in wax or plastic so that it will cut properly. A section of interest is cut, typically to a thickness dictated by the viewing means, such as 1–150 microns for light microscopy or 30–60 nanometers for electron microscopy. The section is mounted on a glass slide or metal grid. The section is then generally stained, possibly in several stages by chemical dyes, or reagents. If the specimen is to be viewed under an optical microscope, excess water and dye will then be removed and the specimen on the slide will be covered by a glass slip. Finally, the specimen will be observed, analyzed, and observed data are recorded.

Specimen types and methods of study for living specimens are seriously limited by the requirement to keep the specimen alive. In general, specimens may be viewed in vivo or in vitro. A typical in vitro specimen is a tissue culture system. A typical in vivo specimen must also be available in an observable situation, i.e. ear or skin tissue. Because staining and other methods of preparation are inappropriate, specialized phase-contrast or dark-field microscopy are typically used to provide enhanced contrast between the natural structures.

Cytology

Cytology is the study of the structure, function, pathology, and life history of cells. The advantages of cytology, as compared to other histological data collection techniques, include the speed with which it can be performed, its relatively low cost, and the fact that it can lead to a specific diagnosis. Disadvantages include the relatively small sample sizes generally observed, the lack of information regarding tissue architecture, and the relatively high level of skill required of clinicians performing the studies. The specimen collection method used generally depends upon the type of specimen to be collected. Such methods include fine needle aspiration, solid tissue impression smears or scrapings, and fluid smears. Aspiration is essentially specimen collection by suction. Some common specimen types collected by these various methods include thyroid, breast, or prostrate specimens, uterus, cervix or stomach tissues, and excretions (urine or feces) or secretions (sputum, prostatic fluid or vaginal fluid).

The specimen preparation method for cytology is relatively straightforward. The sample is first removed from the area being examined, is then placed on a glass slide, stained, and studied. When the sample is a solid, an additional step may be appropriate, called squash preparation. In this procedure the sample is placed on a first glass slide, squashed with a second glass slide, and then spread across the first glass slide using the second slide.

Analysis of a cytologic specimen typically includes comparison of the specimen to normal cells for the anatomic location of the sample. The cells are then classified as normal or abnormal. Abnormality is typically determined by the presence of inflammation, hyperplasia, or neoplasia. Hyperplasia is an increase in size of a tissue or organ due to the formation of more cells, independent of the natural growth of the body. Neoplasia is the formation of an abnormal growth, i.e. a tumor. Abnormal cells may be sub-classified as inflammatory or non-inflammatory, and the type of inflammatory cells that predominate is determined. Inflammation may be determined by a high, or greater than normal, presence of leukocytes or macrophages. Leukocytes are classified by their physical appearance into two groups: granular or nongranular. Examples of granular leukocytes are neutrophils and eosinophils. Nongranular leukocytes include lymphocytes. If the specimen cells are non-inflammatory, they are then checked for malignancy. If the cells are malignant, type of malignant tissue is determined.

Tissue Typing

Tissue typing is the identification of a patient's human leukocyte antigen (HLA) pattern. The HLA pattern is located on a region of chromosome 6, called the major histocompatibility complex (MHC). The HLA system is crucial to fighting infections because it distinguishes between foreign and native cells for the body's immune system. Thus, this pattern is also crucial for the organ transplant field, because if the donor's and donee's HLA patterns are not similar enough, the donee's immune system will attack ("reject") the transplanted organ or tissue. There are five groups, called loci, of antigens that make up the HLA pattern: HLA-A, HLA-B, HLA-C, HLA-D, and HLA-DR. Each locus of antigens contains many variations, called alleles, identified, if known, with a number, i.e. HLA-A2. Provisionally identified alleles are designated with a letter and number, i.e. HLA-Cw5. Each person inherits an allele of each locus from a parent. Thus, the chance of two siblings having identical HLA patterns is 25%. The closer the relation between two people, the greater the similarity will be in their two respective HLA patterns. Thus, tissue typing has been used to determine the likelihood that two people are related. Also, patients with certain HLA patterns are more prone to certain diseases; however, the cause of this phenomenon is unknown. All that is typically needed to perform the tissue typing test is a blood sample.

Two common methods for testing for the tissue type include serology and DNA testing. Until recently, only serology tests were performed. However, since the amino acid sequences of the alleles of the HLA-A, B, Cw, and DR loci have been determined, DNA testing has become the most widely used testing method for these loci of the HLA pattern. The serology test is generally performed by incubating lymphocytes from a blood sample in a dish containing an antiserum that will destroy, or lyse, a certain allele. A dye is then added to show whether any lysed cells are present. If so, the test is positive for that specific allele.

Immunocytochemistry

Cytochemistry is the study of the chemical constituents of tissues and cells involving the identification and localization of the different chemical compounds and their activities within the cell. Immunocytochemistry comprises a number of methods, where antibodies are employed to localize antigens in tissues or cells for microscopic examination. There are several strategies to visualize the antibody.

For transmitted light microscopy, color development substrates for enzymes are often used. The antibody can be directly labeled with the enzyme. However, such a covalent link between an antibody and an enzyme might result in a loss of both enzyme and antibody activity. For such reasons several multistep staining procedures have been developed, where intermediate link antibodies are used.

Stereology is a quantitative technique providing the necessary mathematical background to predict the probability of an encounter between a randomly positioned, regularly arranged geometrical probe and the structure of interest. Stereological methods have been introduced in quantitative immunocytochemistry. Briefly, a camera may be mounted on a microscope with a high precision motorized specimen stage and a microcator to monitor movements. The camera is coupled to a computer configured to execute stereological software. The analysis is performed at high magnification using an objective with a high numerical aperture, which allows the tissue to be optically dissected in thin slices, such as to a thickness of 0.5 µm. Quantitative analysis requires thick sections (40 µm) with an even and good penetration of the immunohistochemical staining.

Electron microscopy is also commonly used in immunocytochemistry. In a typical sample preparation method the sample is first preserved. In one assembly type, the specimen is embedded in an epoxy resin. Several samples are then assembled into a laminar assembly, called a stack, which facilitates simultaneous sectioning of multiple samples. Another assembly type, called a mosaic, can be used when the stack assembly is infeasible. The mosaic assembly involves placing several samples side-by-side and then imbedding them in an epoxy resin. After the stack or mosaic is assembled, it is then sectioned and examined.

Histopathological Analysis

Histopathological analysis involve in making diagnoses by examination of tissues both with the naked eye and the microscope. Histopathology is classified into three main areas: surgical pathology, cytology, and autopsy. Surgical pathology is the examination of biopsies and resected specimens. Cytology comprises both a major part of screening programs (e.g. breast cancer screening and cervical cytology programs), and the investigation of patients with symptomatic lesions (e.g. breast lumps or head and neck lumps).

Electron Microscopy

Electron Microscopes are scientific instruments that use a beam of highly energetic electrons to examine objects on a very fine scale. There are two common types of electron microscopes: transmission and scanning. Further, specimen sections must be viewed in a vacuum and sliced very thinly, so that they will be transparent to the electron beam.

Two main indicators are used in microscopy: magnification and resolution. Magnification is the ratio of the apparent size of the specimen (as viewed) to the actual size. Electron microscopes allow magnification of a specimen up to 200 times greater than that of an optical microscope. Resolution measures the smallest distance between two objects at which they can still be distinguished. The resolution of an electron microscope is roughly 0.002 µm, up to 100 times greater than that of an optical microscope.

The examination of a specimen by an electron microscope can yield useful information on a specimen, such as topography, morphology, composition, and crystallographic information. The topography of a specimen refers to the surface features of an object. There is generally a direct relation between these features and the material properties (hardness, reflectivity, and so forth) of the specimen. The morphology of a specimen is the shape and size of the particles making up the specimen. The structures of the specimen's particles are generally related to its material properties (ductility, strength, reactivity, and so forth). The composition comprises the elements and compounds comprising a specimen, and the relative amounts of these. The composition of the specimen is generally indicating of its material properties (melting point, reactivity, hardness, and so forth). The crystallographic information relates to the atomic arrangement of the specimen. The specimen's atomic arrangement is also related to its material properties (conductivity, electrical properties, strength, and so forth).

In situ Hybridization

In situ hybridization (ISH) is the use of a DNA or RNA probe to detect the presence of the complementary DNA sequence in cloned bacterial or cultured eukaryotic cells. Eukaryotic cells are cells having a membrane-bound, structurally discrete nucleus, and other well developed subcellular compartments. Eukaryotes include all organisms except viruses, bacteria, and bluegreen algae. There are two common types of ISH: fluorescence (FISH) and enzyme-based.

ISH techniques allow specific nucleic acid sequences to be detected in morphologically preserved chromosomes, cells or tissue sections. In combination with immunocytochemistry, in situ hybridization can relate microscopic topological information to gene activity at the DNA, mRNA, and protein level. Moreover, preparing nucleic acid probes with a stable nonradioactive label can remove major obstacles which hinder the general application of ISH. Furthermore, this may open new opportunities for combining different labels in one experiment. The many sensitive antibody detection systems available for such probes further enhances the flexibility of this method.

Several different fluorescent or enzyme-based systems are used for detecting labeled nucleic acid probes. Such options provide the researcher with flexibility in optimizing experimental systems to achieve highest sensitivity, to avoid potential problems such as endogenous biotin or enzyme activity, or to introduce multiple labels in a single experiment. Such factors as tissue fixation, endogenous biotin or enzyme activity, desired sensitivity, and permanency of record are all considered when choosing both the optimal probe label and subsequent detection system.

Combinations

Any combination in whole or in part of the above methods can be used to optimally diagnose a patient's malady or, more generally, a physical condition, or risk or predisposition for a condition.

Pharmacokinetic Data Resources

Therapeutic Drug Monitoring

Therapeutic drug monitoring (TDM) is the measurement of the serum level of a drug and the coordination of this serum level with a serum therapeutic range. The serum therapeutic range is the concentration range where the drug has been shown to be efficacious without causing toxic effects in most people. Recommended therapeutic ranges can generally be found in commercial and academic pharmaceutical literature.

Samples for TDM must be obtained at the proper elapsed time after a dose for valid interpretation of results to avoid errors. Therapeutic ranges are established based on steady state concentrations of a drug, generally achieved about five half-lives after oral dosing has begun. In some instances, it may be useful to draw peak and trough levels. Peak levels are achieved at the point of maximum drug absorption. Trough levels are achieved just before the next dose. The type of sample used for TDM is also important. For most drugs, therapeutic ranges are reported for serum concentrations. Some TDM test methods may be certified for use with both serum and plasma. Manufactures generally indicate which samples are acceptable.

A number of drugs can be subject to TDM. For example, common anticonvulsant drugs which require therapeutic monitoring include phenytoin, carbamazepine, valproic acid, primidone, and phenobarbital. Anticonvulsant drugs are usually measured by immunoassay. Immunoassays are generally free from interferences and require very small sample volumes.

As a further example, the cardioactive drug digoxin is a candidate for therapeutic monitoring. The bioavailability of different oral digoxin preparations is highly variable. Digoxin pharmacokinetics follow a two-compartment model, with the kidneys being the major route of elimination. Patients with renal disease or changing renal function are typically monitored, since their elimination half life will change. The therapeutic range for digoxin is based on blood samples obtained a predetermined amount of time, such as eight hours, after the last dose in patients with normal renal function. Particular periods may also be specified as a basis for determining steady state levels before the samples are drawn. Immunoassays, typically available in kits, indicate significant interferences or cross-reactivities for the tests.

As a further example, theophylline is a bronchodilator with highly variable inter-individual pharmacokinetics. Serum levels are be monitored after achievement of steady-state concentrations to insure maximum therapeutic efficacy and to avoid toxicity. Trough levels are usually measured, with immunoassays being the most common method used for monitoring this drug. Similarly, for lithium compounds used to treat bipolar depressive disorders, serum lithium concentrations are measured by ion selective electrode technology. An ion selective electrode has a membrane which allows passage of the ion of interest but not other ions. A pH meter is an example of an ion selective electrode which responds to hydrogen ion concentrations. A lithium electrode will respond to lithium concentrations but not to other small cations such as potassium.

As yet a further example, tricyclic antidepressant drugs include imipramine, its pharmacologically active metabolite desipramine; amitriptyline and its metabolite nortriptyline, as well as doxepin and its metabolite nordoxepin. Both the parent drugs and the metabolites are available as pharmaceuticals. These drugs are primarily used to treat bipolar depressive disorders. Imipramine may also be used to treat enuresis in children, and severe attention deficit hyperactivity disorder that is refractory to methylphenidate. Potential cardiotoxicity is the major reason to monitor these drug levels. Immunoassay methods are available for measuring imipramine and the other tricyclics, but high performance liquid chromatography (HPLC) methods are generally preferred. When measuring tricyclic antidepressants which have pharmacologically active metabolites, the parent drug and the metabolite are generally measured.

Receptor Characterization and Measurement

Receptor characterizations are traditionally performed using one of several methods. These methods include direct radioligand binding assays, radioreceptor assays, and agonist and antagonist interactions, both complete and partial. A radioligand is a radioactively labeled drug that can associate with a receptor, transporter, enzyme or any protein of interest. Measuring the rate and extent of binding provides information on the number of binding sights and their affinity and pharmacological characteristics.

Three commonly used experimental protocols include saturation binding experiments, kinetic experiments, and competitive binding experiments. Saturation binding protocols measure the extend of binding in the presence of different concentrations of the radioligand. From an analysis of the relationship between binding and ligand concentration, parameters, including the number of binding sites, binding affinity, and so forth can be determined. In kinetic protocols, saturation and competitive experiments are allowed to incubate until binding has reached equilibrium. Kinetic protocols measure the time course of binding and dissociation to determine the rate constants of radioligand binding and dissociation. Together, these values also permit calculation of the KD. In competitive binding protocols, the binding of a single concentration of radioligand at various concentrations of an unlabeled competitor are measured. Such protocols permit measurement of the affinity of the receptor for the competitor.

Due to expense and technical difficulty, direct radioligand binding assays are often replaced with competitive binding assays. The latter technique also permits radiolabeling of drugs to promote an understanding of their receptor properties. Techniques for drug design and development, based upon combinatorial chemistry often employ radioreceptor assays. Radioreceptor assay techniques are based upon the fact that the binding of a ligand having high affinity for a macromolecular target may be measured without the need for equilibrium dialysis, as long as the ligand-receptor complex can be separated from the free ligand. By labeling the ligands with appropriate radioactive substances, the ligand-receptor combination can be measured. Such assays are both rapid and highly sensitive. Antagonism is the process of inhibiting or preventing an agonist-induced receptor response. Agents that produce such affects are referred to as antagonists. The availability of selective antagonists has provided an important element for competitive binding protocols.

Miscellaneous Resources

Physical Exam

A comprehensive physical examination provides an opportunity for a healthcare professional to obtain baseline information about the patient for future use. The examination, which typically occurs in a clinical setting, provides an opportunity to collect information on patient history, and to provide information on diagnoses, and health practices. Physical examinations may be complete, that is cover many or virtually all of the body, or may be specific to symptoms experienced by a patient.

In a typical physical examination, the examiner observes the patient's appearance, general health, behavior, and makes certain key measurements. The measurements typically include height, weight, vital signs (e.g. pulse, breathing rate, body temperature and blood pressure). This information is then recorded, typically on paper for a patient's file. In accordance with aspects of the present technique, much of the information can be digitized for inclusion as a resource for compiling the integrated knowledge base and for providing improved care to the patient. Exemplary patient data acquisition techniques and their association with the knowledge base and other resources will be discussed in greater detail below.

In a comprehensive physical examination, the various systems of the patient's body will generally be examined, such as in a sitting position. These include exposed skin areas, where the size and shape of any observable lesions will be noted. The head is then examined, including the hair, scalp, skull and face areas. The eyes are observed including external structures and internal structures via an ophthalmoscope. The ears are similarly examined, including external structures and internal structures via an otoscope. The nose and sinuses are examined, including the external nose structures and the nasal mucosa and internal structures via a nasal speculum. Similarly, the mouth and pharynx are examined, including the lips, gums, teeth, roof of the mouth, tongue and throat. Subsequently, the neck and back are typically examined, including the lymph nodes on either side of the neck, and the thyroid gland. For the back, the spine and muscles of the back are generally palpated and checked for tenderness, the upper back being palpated on right and left sides. The patient's breathing is also studied and noted. The breasts and armpits are then examined, including examination of a woman's breasts with the arms in relaxed and raised positions for signs of lesions. For both men and women, lymph nodes of the armpits are examined, as are the movements of the joints of the hand, arms, shoulder, neck and jaw.

Subsequently, generally with the patient lying, the breasts are palpated and inspected for lumps. The front of the chest and lungs are inspected using palpation and percussion, with the internal breath sounds being again noted. The heart rate and rhythm is then checked via a stethoscope, and the blood vessels of the neck are observed and palpated.

The lower body is also examined, including by light and deep palpation of the abdomen for examination of the internal organs including the liver, spleen, kidneys and aorta. The rectum and anus may be examined via digital examination, and the prostate gland may be palpated. Reproductive organs are inspected and the area is examined for hernias. In men, the scrotum is palpated, while in women the pelvic examination is typically performed using a speculum and a Pap test. The legs are inspected for swelling and pulses in the knee, thigh and foot area are found. The groin area is palpated for the presence of lymph nodes, and the joints and muscles are also observed. The musculoskeletal system is also examined, such as for noting the straightness of the spine and the alignment of the legs and feet. The blood vessels are also observed for abnormally enlarged veins, typically occurring in the legs.

A typical physical examiner also includes evaluation of the patients alertness and mental ability. The nervous system may also be examined via neurologic screening, such as by having the patient perform simple physical operations such as steps or hops, and the reflexes of the knees and feet can be tested. Certain reflex functions, such as of the eye, face, muscles of the jaw, and so forth may also be noted, as may the general muscle tone and coordination.

Medical History

Medical history information is generally collected on questionnaires that are completed upon entry of the patient to a medical facility. As noted below, and in accordance with aspects of the present technique, such information may be digitized in advance of a patient visit, and follow-up information may be acquired, also in advance, or during a patient visit. The information may typically include data relating to an insurance carrier, and names and addresses or phone numbers of significant or recent practitioners who have seen or cared for the patient, including primary care physicians, specialists, and so forth. Present medical conditions are generally of interest, including symptoms and disease states or events being experienced by the patient. Particular interests are conditions such as diabetes, high blood pressure, chronic or acute diseases and illnesses, and so forth. Current medications are also noted, including names, doses, when taken, the prescribing physician name, side effects, and so forth. Finally, current allergies, known to the patient, are noted, including allergies to natural and man-made substances.

Medical history information also includes past medical history, even medical information extending into the patient's childhood, immunization records, pregnancies, significant short-term illnesses, longer term conditions, and the like. Similarly, the patient's family history is noted, to provide a general indication of potential pre-dispositions to medical conditions and events. Hospitalizations are also noted, including in-patient stays and emergency room visits, as are surgeries, both major and minor, with information relating to anesthesia and particular invasive procedures.

Medical history data may also include data from other physicians and sources, such as significant or recent blood tests which provide a general background for conditions experienced by the patient. Similar information, such as in the form of film-based images may also be sought to provide this type of background information.

The information provided by the patient may also include certain information relating to the general social history and lifestyle of the patient. These may include habits, such as alcohol or tobacco consumption, diet, exercise, sports and hobbies, and the like. Work history, including current or recent employment or tasks in occupations may be of interest, particularly information relating to hazardous, risky or stressful tasks.

Psychiatric, Psychological History, and Behavioral Testing

A patient's psychiatric history may be of interest, particularly where symptoms or predispositions to treatable or identifiable psychiatric conditions may be of concern. In particular, psychiatrists can provide medication to control a wide range of psychiatric symptoms. Most psychiatrists also provide psychotherapy and counseling services to patients, as well as, where appropriate, to couples, groups, and families. Moreover, psychiatrists can administer electroconvulsive shock therapy (ECT). Psychiatrists are more likely than psychologists to treat individuals with severe mental disorders, and to work with patients on an in-patient basis in a clinical setting. Psychiatric history may be very generally sought, such as on questionnaires before or during office visits, or may be determined through more extensive questioning or testing.

The psychological history, as opposed strictly to the psychiatric history, may depend upon the special interests of the patient seeking care. In particular, the services provided by psychologists will typically depend upon their training, with certain psychologists providing psychotherapy and counseling to individuals, groups, couples and families. Psychologists are also typically trained in the administration, scoring and interpretation of psychological tests. Such tests can assess a variety of psychological factors, including intelligence, personality traits (e.g. via tests such as the Keirsey Temperament Sorter, the Meyers-Briggs Type Indicator), relationship factors, brain dysfunction, and psychopathology. Neuropsychologists may be also do cognitive retraining with brain injured patients.

Behavioral testing is somewhat similar to psychological testing, and may identify cognitive behavioral disorders or simply behavioral patterns. Such tests may be provided in conjunction with psychiatric or psychological evaluations to determine a root cause, psychiatric, psychological or physiological, to certain observed behavior in a patient. Where appropriate, treatment may include counseling or drug administration.

Demographic Data

Certain of the data collected from a patient may be intended to associate the patient with certain groups or population of known characteristics. Statistical study of human populations generally include such demographic data, specially with reference to size and density, distribution, and vital statistics of populations with particular characteristics. Among the demographic variables which may be typically noted are gender, age, race, ethnicity, religious affiliation, marital status, size of household, native language, citizenship, occupation, life expectancy, birthrate, mortality, education level, income, population, water supply and sanitation, housing, literacy, unemployment, disease prevalence, and health risk factors. As noted below, in accordance with aspects of the present technique, patient-specific or patient-adapted feedback or counseling may be provided, including on an automated basis by the present technique based at least upon such demographic data.

Drug Use

Information relating to drug use, similar to general information collected during an examination is typically of particular interest. Such information may include the use of legal and illegal drugs, prescription medications, over-the-counter medications, and so forth. Also, specific substance, even though not generally considered as a drug by a patient may be noted under such categorizations, including vitamins, dietary supplements, alcohol, tobacco, and so forth.

Food Intake

In addition to the information generally collected from the patient regarding diet and medication, specific food intake information may be of interest, depending upon the patient condition. Such information may be utilized to provide specific nutritional counseling to address specific conditions or the general health of the patient. Food intake information generally also includes information regarding the patient's physical activity, ethnic or cultural background, and home life and meal patterns. Specific information regarding appetite and attitude towards food and eating may also be noted and discussed with the patient. Specific allergies, intolerances and food avoidances are of particular interest to address known and unknown symptoms experienced by patients. Similarly, dental and oral health, gastrointestinal problems, and issue of chronic disease may be of interest in counseling clients for food intake or similar issues. Food intake information may also address specific medications or perceived dietary or nutritional problems known to the patient. Also of particular interest are items relating to remote and recent significant weight changes experienced.

Certain assessments may be made relating to food intake based upon information collected or detected from a patient. Such evaluations may include anthropometric data, biochemical assessments, body mass index data, and caloric requirements. Similarly, from patient anthropometric data, ideal body weight and usual body weight information may be computed for further counseling and diagnostic purposes.

Environmental Factors

Various environmental factors are of particular interest in evaluating patient conditions and predispositions for certain conditions. Similar to demographic information, the environmental factors may aide in evaluating potential conditions which are much more subtle and difficult to identify. Typical environmental factors may include, quite generally, life events, exercise, and so forth. Moreover, information on the specific patient or the patient living conditions may be noted, including air pollution, ozone depletion, pesticides, climate, electromagnetic radiation levels, ultraviolet exposure, chemical exposure, asbestos, lead, radon, or other specific exposures, and so forth. Such information may be associated with population information or known relational data, such as problems with teeth and bones associated with fluoride, potential cancer links associated with volatile organics (e.g. benzene, carbon tetrachloride, and so forth), gastrointestinal illnesses and other problems associated with bacteria and viruses (e.g. *E. coli,* giardia lamblia, and so forth), and lengths of cancer, liver damage, kidney damage, and nervous system damage related to inorganics (e.g. asbestos, mercury, nitrates, and so forth).

Gross Pathology

Gross pathology, in general, relates to information on the structure and function of the primary human systems. Such systems include the skeletal system, the endocrine system, the reproductive system, the nervous system, the muscular system, the urinary system, the digestive system, and the respiratory system. Such gross pathology information may be collected in specific inquiries or examinations, or may be collected in conjunction with other general inquiries such as the physical examination or patient history data collection processes described above. Moreover, certain aspects of the gross anatomy information may be gleaned from reference texts, autopsies, anthropomorphic databases, such as the Visible Human Project, and so forth.

Information from Non-Biologic Models

Information from non-biologic models may also be of particular interest in assessing and diagnosing patient conditions. The information is also of particular interest in the overall management of patient care. Information included in this general category of resources includes health insurance information and healthcare financial information. Moreover, for a medical institution, significant amounts of information are necessary to provide adequate patient care on a timely bases, including careful control of management, workflow, and human resources. In institutions providing living arrangements for patients, the data must also include such items as food service, hospital financial information and patient financial information. Much of the information that is patient-specific may be accumulated by an institution in a general patient record.

Other specific information for institutions which aide in the overall management may include information on the business-related aspects of the institution alone or in conjunction with other associated institutions. This information may include data indicative of geographic locations of hospitals, types of clinics, sizes of clinics, specialties of clinics or departments or physicians, and so forth. Patient education materials may also be of particular interest in this group, and the patient educational materials may be specifically adapted for individual patients as described in greater detail below. Finally, information relating to relationships with physicians, including physician referrals and physician needs and preferences may also be of particular interest in this category of resources.

Processing and Analysis

The processing and analysis functions described above performed by the data processing system 10 may take many forms depending upon the data on which the processing is based, the types of analysis desired, and the purpose for the output of the data. In particular, however, the processing and analysis is preferably performed on a wide range of data from the various resources, in conjunction with the integrated knowledge base 12. Among the various modalities and types of resources, several scenarios may be envisaged for performing the processing and analysis. These include analyses that are performed based upon a single modality medical system or resource, single-type multi-modality combinations, and multi-type, multi-modality configurations. Moreover, as noted above, various computer-assisted processing, acquisition, and analysis modules may be employed for one or more of the modality and type scenarios. The following is a description of certain exemplary implementations of modality-based, type-based and computer-assisted processing-based approaches to the use of the data collected and stored by the present system.

Modalities and Types

In a single modality medical system, a clinician initiates a chain of events for the patient data. The events are broken down into various modules, such as the acquisition module, processing module, analysis module, report module and archive module as discussed above. In the traditional method, the report goes back to the referring clinician.

In the present technique, computer processing may be introduced to perform several data operation tasks. In general, in the present discussion, algorithms for performing such operations are referred to as data operating algorithms or CAX algorithms. While more will be said about currently contemplated CAX algorithms and their interaction and integration, at this point, certain such algorithms will be referred to generally, including computer aided acquisition algorithms (CAA), computer aided processing algorithms (CAP), computer aided detection algorithms (CAD). The implemented software also serves to manage the overall work flow, optimizing parameters of each stage from the knowledge of the same module at the present time or at previous times, and/or data from other modules at the present time or at previous times. Furthermore, as shown in the FIG. 1, the knowledge base 12 is created/updated with new data and essentially drives the various computer-aided modules. Thus, knowledge base 12 creation and updates are linked with the comuter aided methods to implement the single modality unit. The details of the CAX modules, including CAA, CAP, CAD, modules 86, 88, 90 (see, e.g. FIG. 5), and knowledge base 12 are detailed below. Furthermore, it should be noted that each of these modules may be specialized for a given clinical question. Thus, if the same clinical question requires multiple acquisitions, for example, or multiple processing and multiple analyses at different time points, the techniques can be generalized to accommodate the temporal aspects of data.

A single-type, multi-modality medical system, in the present context, may consist of any of the columns of the FIG. 8. In FIG. 7, a diagrammatical representation a single-type, multi-modality system with the temporal attributes is illustrated, considering M modalities at N different time points. Of course, all the attributes of a single modality are also applicable to any of the modalities in the multi-modality context, and the diagram simply highlights the interaction between multiple modalities. In FIGS. 6 and 7, interaction within each type is also evident, such as to optimize acquisition, processing and analysis of data. The temporal aspects of a medical event are also considered in the context, such as to modify acquisition, processing and analysis modules based on the temporal attributes of the data. As discussed below, the logic engine 24 (see, e.g. FIG. 5), or more generally, the processing system 10 may use rules to optimize acquisition, processing, and analysis of data between the modalities using the knowledge base 12.

A multi-type, multi-modality medical system essentially may cover the entire range of resources available, including the types and modalities summarized in FIG. 8 In FIG. 6, a diagrammatical representation of a multi-type, multi-modality system with temporal attributes is illustrated, considering different time points. As before, all of the attributes of single-type, multi-modality systems are applicable for any of the types, and the schematic highlights the interaction between multiple types and multiple modalities. In the multi-type, multi-modality context, the interaction among modalities of different types can be used to optimize acquisition, processing and analysis of the data. Here again, the temporal aspects of a medical event from multiple types may be considered and used to modify acquisition, processing and analysis modules based on the temporal attributes of the data. Logic engine 24, and again more generally processing system 10 may use rules to optimize acquisition, processing, and analysis of data between the modalities using the knowledge base. System 10, uses data from tools or modules, such as CAX modules, or, as shown for certain specific such modules, CAA, CAP, CAD modules 86, 88, 90 and from knowledge base 12, and then establishes the relationship, which could then be part of the knowledge base 12.

While any suitable processing algorithms and programs may be utilized to obtain the benefits of the integrated knowledge base approach of the present technique, certain adaptations and integration of the types of programs available may be made for this purpose. As noted above, exemplary computer-assisted data operating algorithms and modules for analyzing medical-related data include computer-assisted diagnosis modules, computer-assisted acquisition modules, and computer-assisted processing modules. The present technique greatly enhances the ability to develop, refine and implement such algorithms by virtue of the high level of integration afforded. More detail is provided below regarding the nature and operation of the algorithms, as well as their interaction and interfacing in accordance with aspects of the present technique Integrated Knowledge Base As noted above, the integrated knowledge base employed in the present technique can be a highly integrated resource comprised of one or more memory devices at one or more locations linked to one another via any desired network links. The integrated knowledge base may further include memory devices on client components, such as the resources themselves, as will commonly be the case in certain imaging systems. In limited implementations, the integrated knowledge base may combine very few such resources. In larger implementations, or as an implementation is expanded over time, further integration and interrelation between data and resources may be provided. As noted throughout the present discussion, any and all of the resources may not only serve as users of the data, but may provide data where desired.

The presently contemplated integrated knowledge base may include raw data as well as semi-processed data, processed data, reports, tabulated data, tagged data, and so forth. In a minimal implementation, the integrated knowledge base may comprise a subset of raw data or raw data basis. However, in a more preferred implementation, the integrated knowledge base is a superset of such raw databases and further includes filtered, processed, or reduced dimension data, expert opinion information, such as relating to rules of clinical events, predictive models, such as based upon symptoms or other inputs and disease or treatment considerations or other outputs, relationships, interconnections, trends, and so forth. As also noted throughout the present discussion, contents of the integrated knowledge base may be validated and verified, as well as synchronized between various memory devices which provide or draw upon the knowledge present in the knowledge base.

In general, the integrated knowledge base as presently contemplated enables evidence-based medicine to be seamlessly integrated into common practice of medicine and the entire healthcare enterprise. That is, the integrated knowledge base serves to augment the wealth of domain knowledge and experience mentally maintained by the clinicians or users as well as the related clinical and non-clinical communities which provide data and draw upon the data in the various algorithmic programs implemented. Also as described throughout the present discussion, the integrated knowledge base may be distributed and federated in nature, such as to accommodate raw databases, data resources, and controllable and prescribable resources.

Current practice for knowledge base creation is to collect representative data for a particular clinical event, set up a domain-expert panel to review the data, use experts to categorize the data into different valid groupings, and corroborate the expert findings with some reference standard technique. For example, to create an image knowledge base of lung nodule determination from radiography images, the expert panel may group images in terms of degree of subtlety of nodules and corroborate the radiological findings with biopsies. In the present technique, such methodologies may serve as a first basic step for given data of clinical relevance. However, the classification process may then be automated based on the attributes provided by domain experts and adjunct methods. In one embodiment, any clinical data may be automatically categorized and indexed so that it can be retrieved on demand for various intended purposes.

Logic Engine

The logic engine essentially contains the rules that coordinate the various functions carried out by the system. Such coordination includes accessing and storing data in the knowledge base, as well as execution of various computer-assisted data operating algorithms, such as for feature detection, diagnosis, acquisition, processing and decision-support. The logic engine can be rule-based, and may include a supervised learning or unsupervised learning system. By way of example, functions performed by the logic engine may include data traffic control, initiation of processing, linking to resources, connectivity, coordination of processing (e.g. sequencing), and coordination of certain activities such as access control, "handshaking" of components, interface definition, and so forth.

Temporal Processing Module

In accordance with one aspect of the present techniques involves simply performing temporal change analysis on a single modality data. The results can be presented to the user by displaying temporal change data and the current data side-by-side, or by fusing the temporal results on the current data to highlight temporal changes. Another approach is to use data of at least one modality and its temporal counterpart from another modality to perform temporal change analysis. Yet another approach would involve performing temporal analysis on multiple-type data to fully characterize the medical condition in question.

Temporal processing may generally include the following general modules: acquisition/storage module, segmentation module, registration module, comparison module, and reporting module.

The acquisition/storage module contains acquired medical data. For temporal change analysis, means are provided to access the data from storage corresponding to an earlier time point. To simplify notation in the subsequent discussion we describe only two time points $t_1$ and $t_2$, even though the general approach can be extended for any type of medical data in the acquisition and temporal sequence. The segmentation module provides automated or manual means for isolating features, volumes, regions, lines, and/or points of interest. In many cases of practical interest, the entire data can be the output of the segmentation module. The registration module provides methods of registration for disparate medical data. Several examples may assist in illustrating this point.

In case of single modality medical images, if the regions of interest for temporal change analysis are small, rigid body registration transformations, including translation, rotation, magnification, and shearing may be sufficient to register a pair of images from $t_1$ and $t_2$. However, if the regions of interest are large, such as including almost an entire image, warped, elastic transformations may be applied. One way to implement the warped registration is to use a multi-scale, multi-region, pyramidal approach. In this approach, a different cost function highlighting changes may be optimized at every scale. An image is resampled at a given scale, and then it is divided into multiple regions. Separate shift vectors are calculated at different regions. Shift vectors are interpolated to produce a smooth shift transformation, which is applied to warp the image. The image is resampled and the warped registration process is repeated at the next higher scale until the pre-determined final scale is reached.

In the case of multi-modality medical images, maximizing mutual information can perform rigid and warped registration. In certain medical data, there may not be a need to do any spatial registration at all. In such cases, data would be a single scale value or a vector.

The comparison module provides methods of comparison for disparate medical data. For Example, registered image comparison can be performed in several ways. One method involves subtracting two images to produce a difference image. Alternatively, two images $S(t_1)$ and $S(t_2)$ can be compared using an enhanced division method, which is described as $[S(t_1) * S(t_2)]/[S(t_2) * S(t_2)+\Phi]$, where the scalar constant $\Phi>0$. In the case of single scalar values, temporal trends for a medical event can be compared with respect to known trends for normal and abnormal cases.

The report module provides the display and quantification capabilities for the user to visualize and or quantify the results of temporal comparison. In practice, one would use all the available data for the analysis. In the case of medical images, several different visualization methods can be employed. Results of temporal comparisons can be simultaneously displayed or overlaid on one another using a logical operator based on some pre-specified criterion. For quantitative comparison, color look-up tables can be used. The resultant data can also be coupled with an automated pattern recognition technique to perform further qualitative and/or manual/automated quantitative analysis of the results.

Artificial Neural Network

Figure 15:
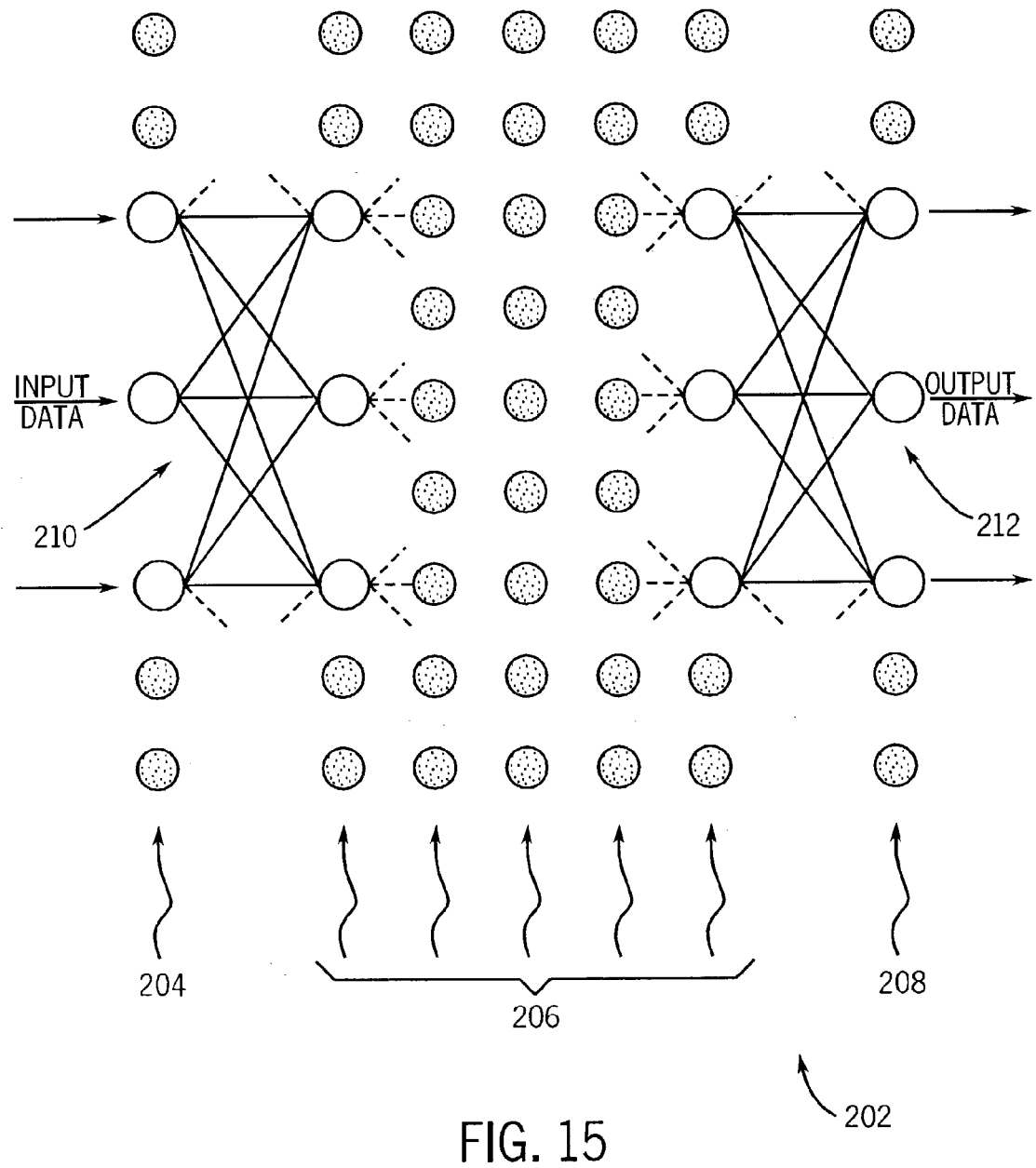
FIG. 15 is a diagrammatical overview of an exemplary neural network system which may be used to establish and configure the knowledge base in accordance with aspects of the present technique.

A general diagrammatical representation of an artificial neural network is shown in FIG. 15 and designated by the reference numeral 202. Artificial neural networks consist of a number of units and connections between them, and can be implemented by hardware and/or software. The units of the neural network may generally be categorized into three types of different groups (layers), according to their functions, as illustrated in FIG. 15. A first layer, input layer 204, is assigned to accept a set of data representing an input pattern, a second layer, output layer 208, is assigned to provide a set of data representing an output pattern, and an arbitrary number of intermediate layers, hidden layers 206, convert the input pattern to the output pattern. Because the number of units in each layer is determined arbitrarily, the input layer and the output layer include sufficient numbers of units to represent the input patterns and output patterns, respectively, of a problem to be solved. Neural networks have been used to implement computational methods that learn to distinguish between objects or classes of events. The networks are first trained by presentation of known data about objects or classes of events, and then are applied to distinguish between unknown objects or classes of events.

Figure 16:
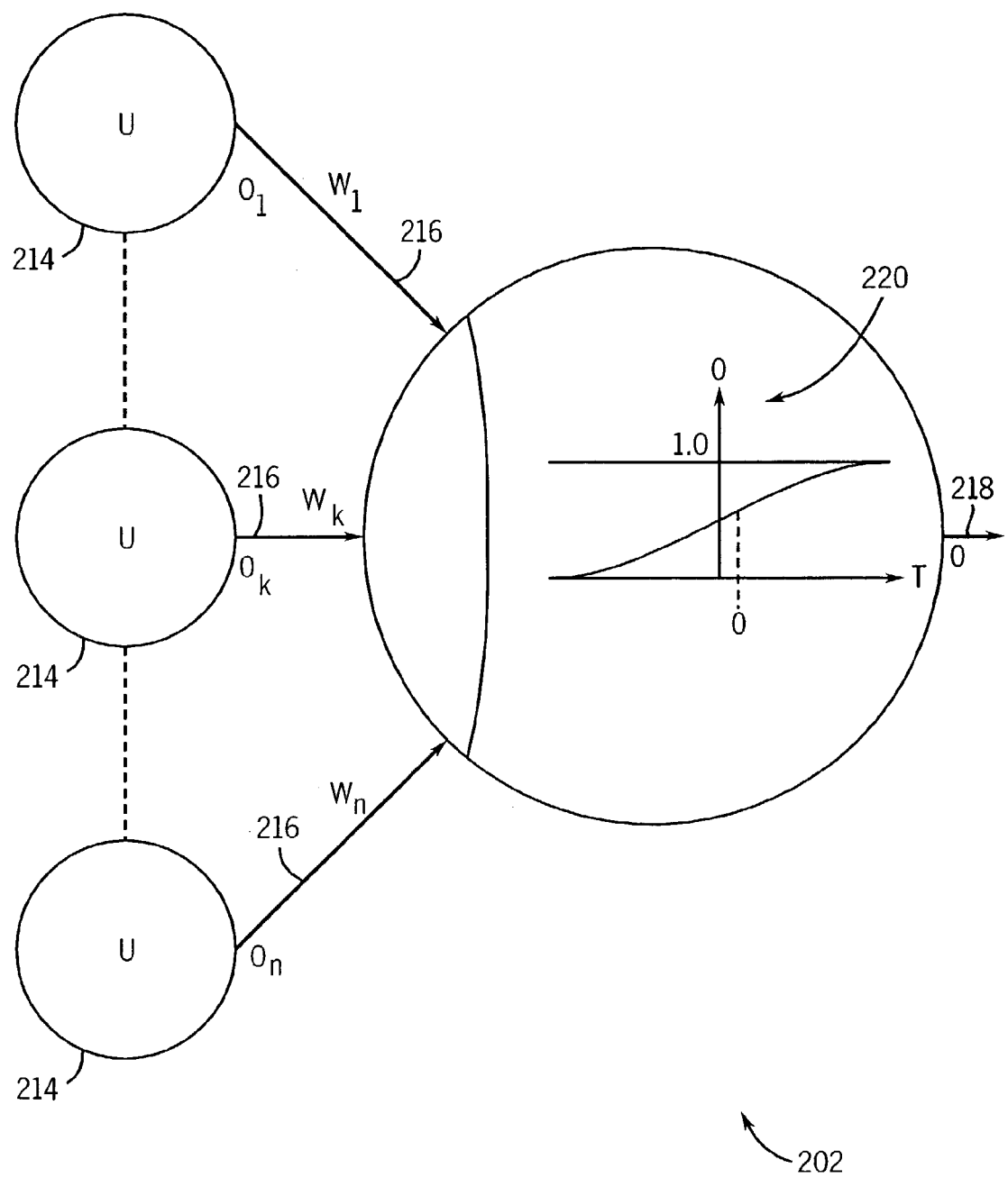
FIG. 16 is a diagrammatical overview of an expert system which may similarly be used to program and configure a knowledge base.

Briefly, the principle of neural network 202 can be explained in the following manner. Normalized input data 210, which may be represented by numbers ranging from 0 to 1, are supplied to input units of the neural network. Next, the output data 212 are provided from output units through two successive nonlinear calculations (in a case of one hidden layer 206) in the hidden and output layers 208, 210. The calculation at each unit in the layer, excluding the input units, may include a weighted summation of all entry numbers, an addition of certain offset terms and a conversion into a number ranging from 0 to 1 typically using a sigmoid-shape function. In particular, as represented diagrammatically in FIG. 16, units 214, which may be labeled $O_1$ to $O_n$, represent input or hidden units, $W_1$ through $W_n$ represent the weighting factors 216 assigned to each respective output from these input or hidden units, and T represents the summation of the outputs multiplied by the respective weighting factors. An output 218, or O is calculated using the sigmoid function 220 given where $\theta$ represents an offset value for T. An example sigmoid function is given by the following expression: $1/[1+\exp(-T+\theta)]$. The weighting factors and offset values are internal parameters of the neural network 202, which are determined for a given set of input and output data.

Two different basic processes are involved in the neural network 202, namely, a training process and a testing process. The neural network is trained by the back-propagation algorithm using pairs of training input data and desired output data. The internal parameters of the neural network are adjusted to minimize the difference between the actual outputs of the neural network and the desired outputs. By iteration of this procedure in a random sequence for the same set of input and output data, the neural network learns a relationship between the training input data and the desired output data. Once trained sufficiently, the neural network can distinguish different input data according to its learning experience.

Expert Systems

One of the results of research in the area of artificial intelligence (AI) has been the development of techniques which allow the modeling of information at higher levels of abstraction. These techniques are embodied in languages or tools, which allow programs to be built to closely resemble human logic in their implementation and are therefore easier to develop and maintain. These programs, which emulate human expertise in well-defined problem domains, are generally called expert systems.

The component of the expert system that applies the knowledge to the problem is called the inference engine. Four basic control components may be generally identified in an inference engine, namely, matching (comparing current rules to given patterns), selection (choosing most appropriate rule), implementation (implementation of the best rule), and execution (executing resulting actions).

To build an expert system that solves problems in a given domain, a knowledge engineer, an expert in AI language and representation, starts by reading domain-related literature to become familiar with the issues and the terminology. With that as a foundation, the knowledge engineer then holds extensive interviews with one or more domain experts to "acquire" their knowledge. Finally, the knowledge engineer organizes the results of these interviews and translates them into software that a computer can use. The interviews typically take the most time and effort of any of these stages.

Rule-based programming is one of the most commonly used techniques for developing expert systems. Other techniques include fuzzy expert systems, which use a collection of fuzzy membership functions and rules, rather than Boolean logic, to reason relationships between data. In rule-based programming paradigms, rules are used to represent heuristics, or "rules of thumb," which specify a set of actions to be performed for a given situation. A rule is generally composed of an "if" portion and a "then" portion. The "if" portion of a rule is a series of patterns which specify the facts (or data) which cause the rule to be applicable. The process of matching facts to patterns is generally called pattern matching. The expert system tool provides the inference engine, which automatically matches facts against patterns and selects the most appropriate rule. The "if" portion of a rule can actually be thought of as the "whenever" portion of a rule, because pattern matching occurs whenever changes are made to facts. The "then" portion of a rule is the set of actions to be implemented when the rule is applicable. The actions of applicable rules are executed when the inference engine is instructed to begin execution. The inference engine selects a rule, and then the actions of the selected rule are executed (which may affect the list of applicable rules by adding or removing facts). The inference engine then selects another rule and executes its actions. This process continues until no applicable rules remain.

Initiation of Processing Functions and Strings

As used herein, the term "processing string" is intended to relate broadly to computer-based activities performed to acquire, analyze, manipulate, enhance, generate or otherwise modify or derive data within the integrated knowledge base or from data within the integrated knowledge base. The processing may include, but is not limited to analysis of patient-specific clinical data. Processing strings may act upon such data, or upon entirely non-clinical data, but in general will act upon both. Thus, processing strings may include activities for acquisition of data (both for initiating acquisition and terminating acquisition, and for setting acquisition settings and protocols, or notification that acquisition is desired or desirable).

A user-initiated processing string, for example, might include launching of a computer-assisted detection routine to identify calcifications possibly visible within cardiac CT data. While this processing string proceeds, moreover, the system, based upon the requested routine and the data available from other resources, may automatically initiate a processing string which fetches cholesterol test results from the integrated knowledge base for analysis of possible relationships between the requested data analysis and the cholesterol test results. Conversely, when analysis of cholesterol test results is requested or initiated, the system may detect the utility in performing imaging that would assist in evaluating or diagnosing related conditions, and inform the user (or a different user) of the need or desirability to schedule acquisition of images that would form the basis for the complementary evaluation.

It should also be noted that the users that may initiate processing strings may include a wide range of persons with diverse needs and uses for the raw and processed data. These might include, for example, radiologists requesting data within and derived from images, insurers requesting information relating or supporting insurance claims, nurses in need of patient history information, pharmacists accessing prescription data, and so forth. Users may also include the patient him or herself, accessing diagnostic information or their own records. Initiation based upon a change in data state may look to actual data itself, but may also rely on movement of data to or from a new workstation, uploading or downloading of data, and so forth. Finally, system-initiated processing strings may rely on simple timing (as at periodic intervals) or may rely on factors such as the relative level of a parameter or resource. System-initiated processing strings may also be launched as new protocols or routines become available, as to search through existing data to determine whether the newly available processing might assist in identifying a condition therefore unrecognized.

Figure 17:
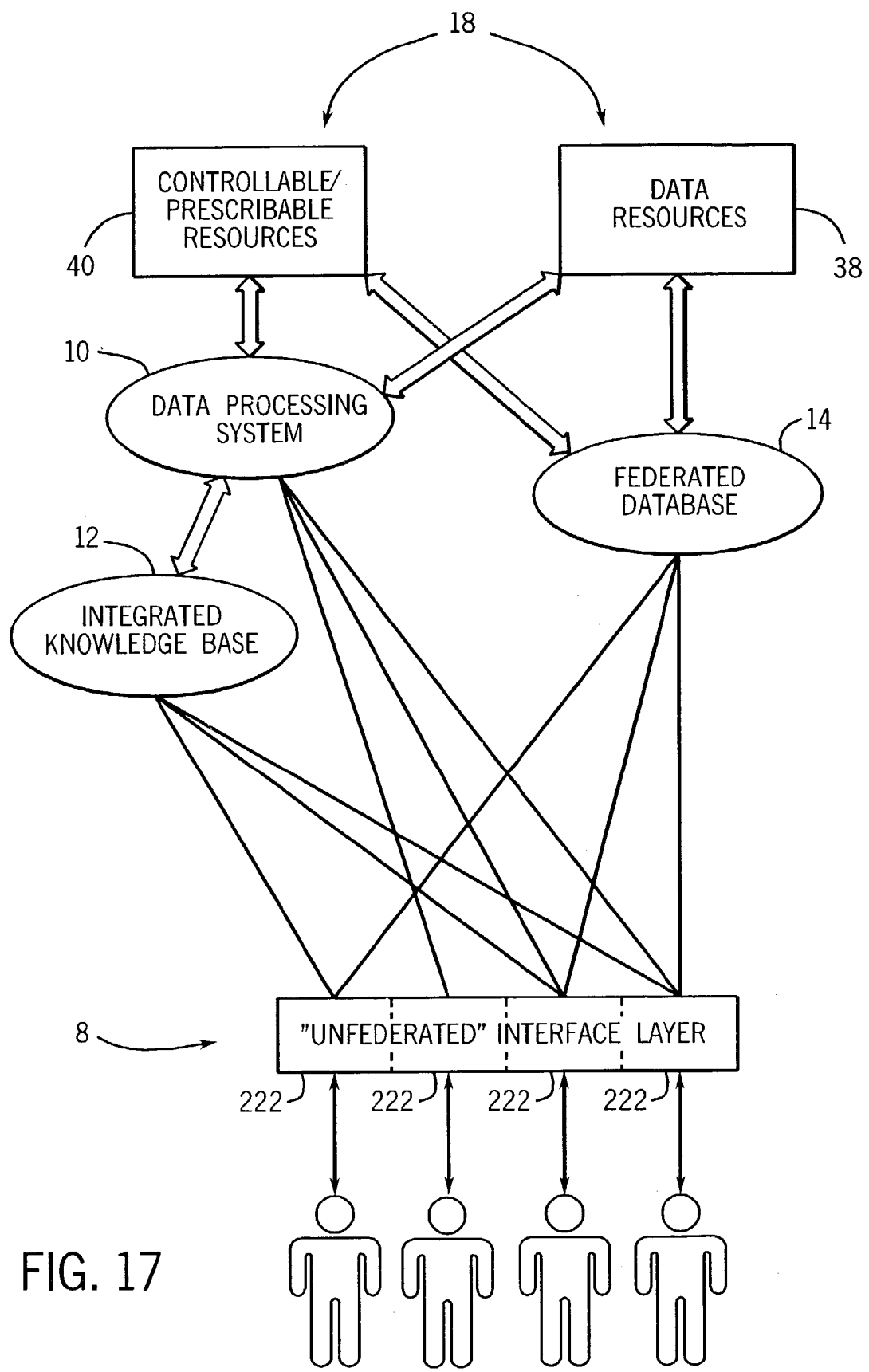
FIG. 17 is a diagrammatical overview of certain components of the system in accordance with the present technique illustrating interaction between the federated database, the integrated knowledge base, data processing system, and an unfederated interface layer for acquiring information from a series of clinicians, and for providing information for output.

As noted above, the data processing system 10, integrated knowledge base 12, and federated database 14 can all communicate with one another to provide access, translation, analysis and processing of various types of data from the diverse resources available. FIG. 17 illustrates this feature of the present technique again, with emphasis upon the interface 8 provided for users, such as clinicians and physicians. The interface 8, while permitting access to the various resources of the system, including the data processing system, the integrated knowledge base, and the federated database, will generally allow for a wide range of interface types and systems. In particular, as designated diagrammatically by the reference numeral 222 in FIG. 17, the "unfederated" interface layer comprising the interface 8 may include a range of disparate and different interface components at single institutions, or at a wide range of different institutions widely geographically dispersed from one another. Moreover, the basic operating systems of the interfaces need not be the same, and the present technique contemplates that various types of interfaces may be united and configured in the unfederated interface layer separately, and nevertheless enable to communicate with one or more of the data processing system, the integrated knowledge base and the federated database. In particular, where an integrated knowledge base and a federated database are provided, these may accommodate the various types of interfaces in the layer, such as through the use of standardized protocols as noted above, including HTML, XML, and so forth. The interface layer may also permit automatic or use-prompted queries of the integrated knowledge base, the data processing system, or the federated database. In particular, where appropriate, the users may not be aware of queries executed by programs implemented on workstations, such as by management of input or output of client data, filing of claims, prescription of data acquisition sequences, medications, and so forth.

Figure 18:
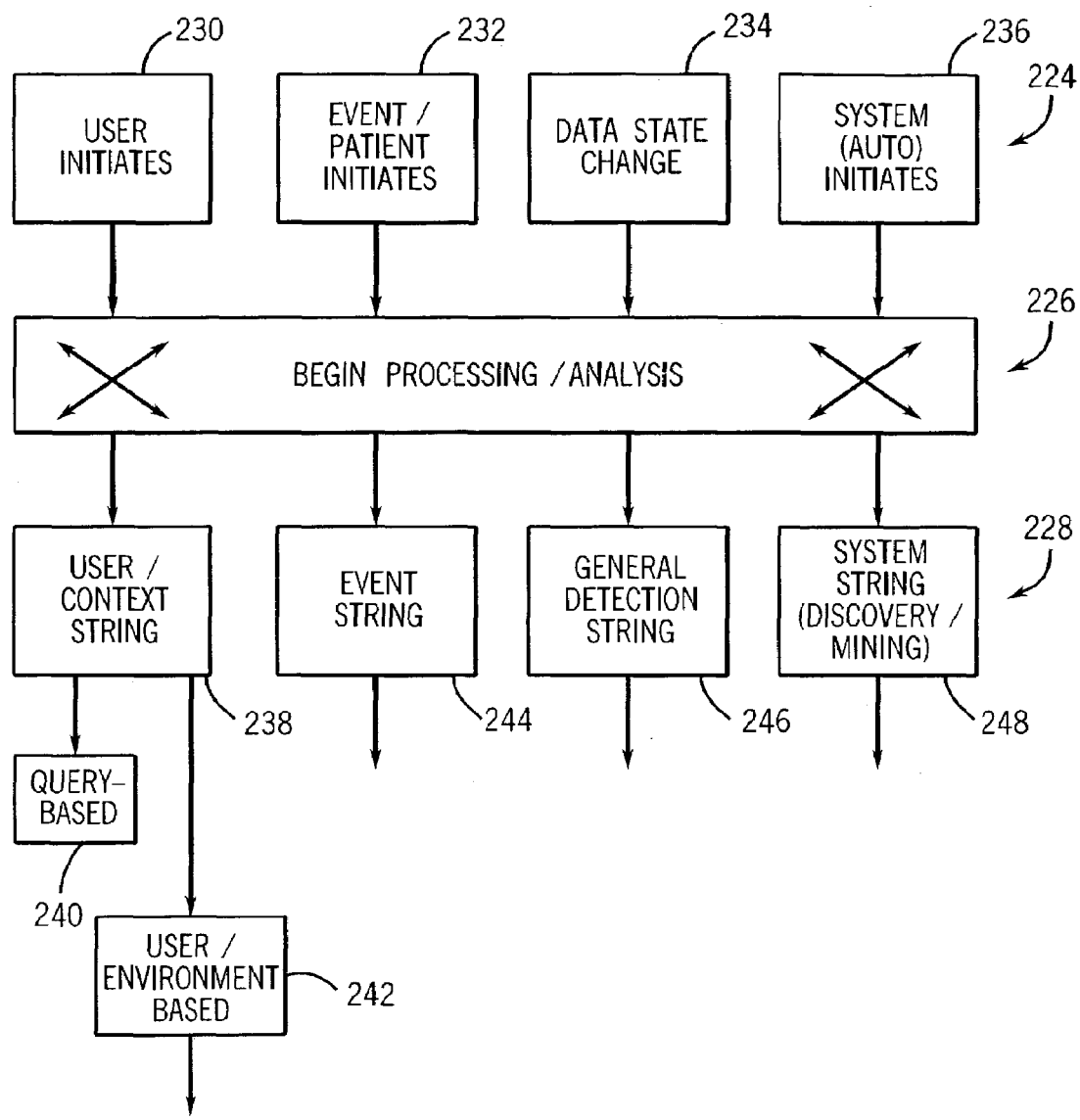
FIG. 18 is a diagrammatical flow chart of a series of processing strings which may be initiated in various manners to acquire, analyze and output information from the resources and knowledge base established by the present techniques.

The interface layer, and the programming included therein and in the data processing system may permit a wide range of processing functions to be executed based upon a range of triggering events. These events maybe initiated and carried out in conjunction with use requests, or may be initiated in various other manners. FIG. 18 diagrammatically illustrates certain of the initiating and processing functions which may be performed in this manner.

As shown in FIG. 18, various initiating sources 224 may be considered for initiating the data acquisition, processing, and analysis on the data from the resources and knowledge base described above. The initiating sources 224 commence processing as indicated generally at reference numeral 226 in FIG. 18, in accordance with routines stored in one or more of the data processing system, integrated knowledge base, and federated database, or further more within the resources, including the controllable prescribable resources and the data resources. The particular processing may be stored, as noted above, and a single computer system comprised in the data processing system, or dispersed through various computer systems which cooperate with one another to perform the data processing and analysis. Following initiation of the processing, processing strings may be carried out as indicated generally at reference numeral 228 in FIG. 18. These processing strings may include a wide range of processing and analysis of functions, typically designed to provide a caregiver with enhanced insights into patient care, to process the data required for the patient care, including clinical and non-clinical data, to enhance function of an institution providing the care, to detect trends or relationships within the patient data, and to perform general discovery and mining of relationships for future use.

The present technique contemplates that a range of initiating sources 224 may commence the processing and analysis functions in accordance with the routines executed by the system. In particular, for such initiating sources are illustrated in FIG. 18, including a user initiating source 230, an event or patient initiating source 232, a data state change source 234, and a system or automatic initiating source 236. Where a user, such as a clinician, physician, insurance company, clinic or hospital employee, management or staff user, and the like initiates a request that draws upon the integrated knowledge base or the various integrated resources described above, a processing string may begin that calls upon information either already stored within the integrated knowledge base or accessible by locating, accessing, and processing data within one or more of the various resources. In a typical setting, a user may initiate such processing at a workstation where a query or other function is performed. As noted above, the query may be obvious to the user, or may be inherent in the function performed on the workstation.

Another contemplated initiating source is the event or patient as indicated at reference numeral 232 in FIG. 18. In general, many medical interactions will begin with specific symptoms or medical events which trigger contact with a medical institution or practitioner. Upon logging such an event by a patient or clinician interfacing with the patient, a processing string may begin which will include a range of interactive steps, such as access to patient records, updating of patient records, acquisition of details relating to symptoms, and so forth as described more fully below. The event to patient initiated processing string, while used to perform heretofore unavailable and highly integrated processing in the present context, may be generally similar to the types of events which drive current medical service provision.

The data processing system 10 may generally monitor a wide range of data parameters, including the very state of the data (static or changing) to detect when new data becomes available. The new data may become available by updating patient records, accessing new information, uploading or downloading data to and from the various controllable and prescribable resources and data resources, and so forth. Where desired, the programs executed by the data processing system may initiate processing based upon such changes in the state of data. By way of example, upon detecting that a patient record has been updated by a recent patient contact or the availability of clinical or non-clinical data, the processing string may determine whether subsequent actions, notifications, reports or examinations are in order. Similarly, the programs carried out by the data processing system may automatically initiate certain processing as indicated at reference numeral 236 in FIG. 18. Such system-initiated processing may be performed on a routine bases, such as predetermined time intervals or at the trigger of various system parameters, such as inventory levels, newly-available data or identification of relationships between data, and so forth.

A particularly powerful aspect of the highly integrated approach of the present technique resides in the fact that, regardless of the initiating source of the processing, various processing strings may result. As summarized generally in FIG. 18, for example, the processing strings 228, while generally aligned with various initiating sources in the figure, may result from other initiating sources and executed programs. For example, a user or context string 238 may include processing which accesses and returns processed information to respond precisely to a user-initiated processing event, or in conjunction with the particular context within which a user accesses the system. However, such processing strings may also result from event or patient initiated processing, data state changes, and system-initiated processing. Moreover, it should be noted that several types of specific strings may follow within the various categories. For example, the user or context string 238 may include specific query-based processing as indicated at reference numeral 240, designed to identify and return data which is responsive to specific queries posed by a user. Alternatively, user or environment-based strings 242 may result in which data accessed and returned is user-specific or environment-specific. Examples of such processing strings might include access and processing of data for analysis of interest to specific users, such as specific types of clinicians or physicians, financial institutions, and insurance companies.

As a further example of the various processing strings which may result from the initiating source processing, event strings 244 may include processing which is specific to the medical event experienced by a patient, or to events experienced in the past or which may be possible in future. Thus, the event strings 244 may result from user initiation, event or patient initiation, data state change initiation, or system initiation. In a typical context, the event string may simply follow the process of a medical event or symptom being experienced by a patient to access information, process the information, and provide suggestions or diagnoses based upon the processing. As noted above, the suggestions may include the performance of additional processing or analysis, the acquisition of additional information, both automatically and with manual assistance, and so forth.

A general detection string 246 might also be initiated by the various initiating sources. In the present context, the general detection string 246 may include processing designed to identify relevant data or relationships which were not specifically requested by a user, event, patient, data state change or by the system. Such general detection strings may correlate new data in accordance with relationships identified by the data processing system or integrated knowledge base. Thus, even where a patient or user has not specifically requested detection of relationships or potential correlations, programs executed by the data processing system 10 may nevertheless execute comparisons and groupings to identify risks, potential treatments, financial management options and so forth under a general detection string.

Finally, a processing string designated in FIG. 18 as a system string 248 may be even more general in nature. The system string may be processing which is executed with the goal of discovering relationships between data available from the various resources. These new relationships may be indicative of new ways to diagnose or treat patients such as based upon recognizable trends or correlations, analysis of success or failure rates, statistical analyses of patient care results, and so forth. As in the previous examples, the system string may be initiated in various manners, including at the automatic initiation of the system, but also with changes in data state, upon the occurrence of newly detected medical event or by initiation of the patient, or by a specific request of a user.

Computer-Assisted Patient Data Capture and Processing

In accordance with one aspect of the present technique, enhanced processing of patient data is provided by coordinating data collection and processing directly from the patient with data stored in the integrated knowledge base 12. For the present purposes, it should be borne in mind that the integrated knowledge base 12 may be considered to include information within various resources themselves, or processed information resulting from analysis of such raw data. Moreover, in the present context the integrated knowledge base is considered to include data which may be stored in a variety of locations both within an institution and within a variety of institutions located in a single location or in quite disparate locations. The integrated knowledge base may, therefore, include a variety of coordinated data collection and repository sites. Exemplary logical action classes and timeframes, with associated exemplary actions, are illustrated generally in FIG. 19.

Figure 19:
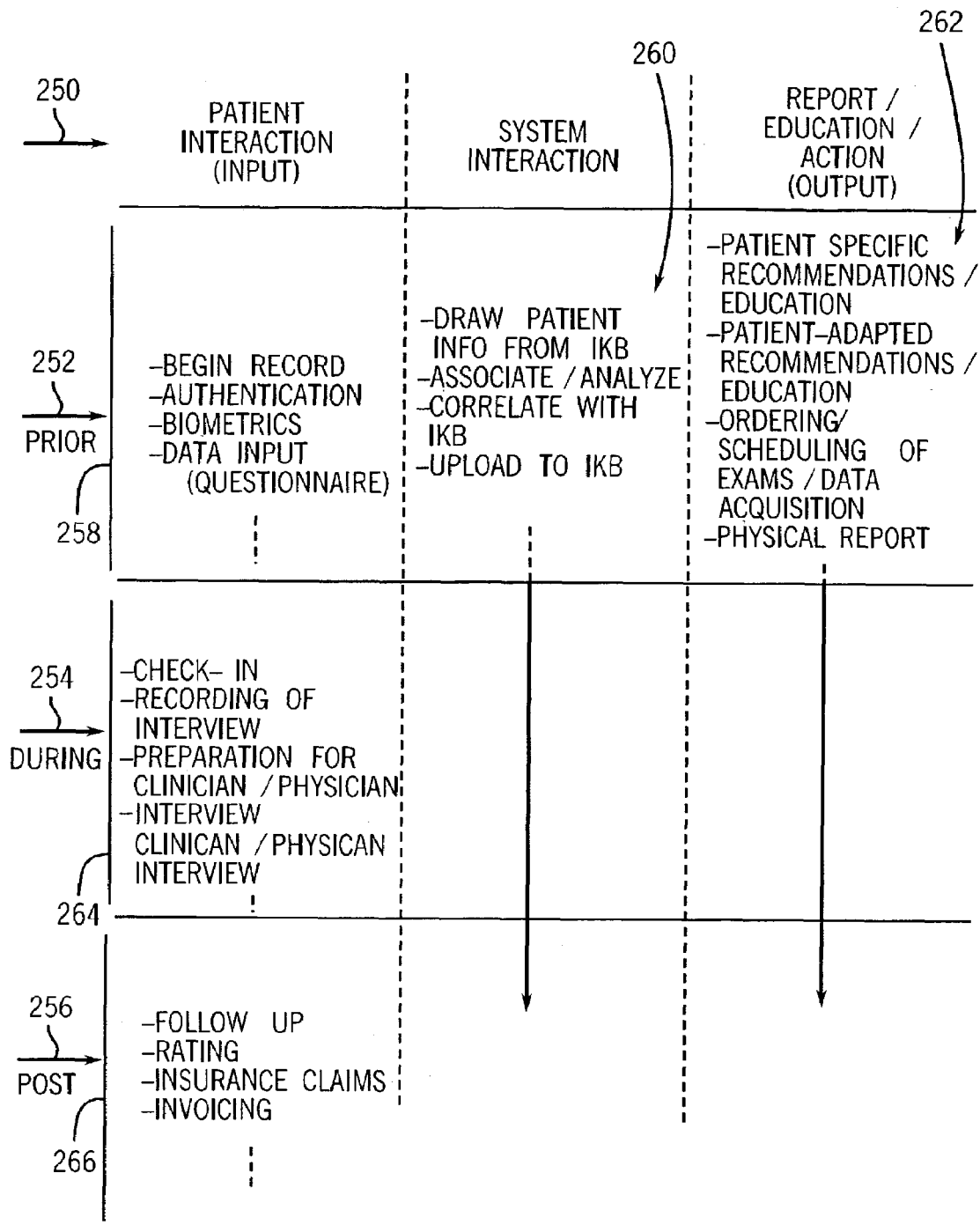
FIG. 19 is a diagrammatical flow chart of certain events and processes which may take place over time to acquire patient information by patient interaction, perform system interactive functions, and output information for users, including patients and clinicians.

Referring to FIG. 19, the patient information which is included in the integrated knowledge base may result from any one or more of the types of modalities described above, and, more generally, of the various resource types. Moreover, as also described above, patient information may result from analysis of this type of data in conjunction with other generally available data in the data resources, such as different graphic information, proprietary or generally accessible databases, subscription databases, digitized reference materials, and so forth. However, the information is particularly useful when coordinated with a patient contact, such as a visit to a physician or facility. In the diagrammatical representation of FIG. 19, different distinct classes of action, designated generally at reference numeral 250, may be grouped logically, such as patient interactions, system interactions, and report or education-type actions. These action classes may be further considered, generally, as inputs, processing, and outputs of the overall system. Moreover, the action classes may be thought of as occurring by reference to a patient contact, such as an on-site visit. In this sense, the actions may be generally classified as those taken prior to a visit or contact, as noted at reference numeral 252, those taken during a contact, as illustrated at reference numeral 254, and post-contact actions, as indicated at reference numeral 256.

It has been found, in the present technique, that by collection of certain patient information at these various stages of interaction, information from the integrated knowledge base may be extremely useful in providing enhanced diagnosis, analysis, patient care, and patient instruction. In particular, several typical scenarios may be envisaged for the collection and processing of data prior to a patient contact or on-site visit.

As an example of the type of information which may be collected prior to a patient contact, sub-classes of actions may be performed, as indicated at reference numeral 258 in FIG. 19. By way of example, prior to a patient visit, a record for the patient contact or medical event (e.g. the reason for the visit) may be captured to begin a new or continuing record. Such initiation may begin by a patient phone call, information entered into a website or other interface, instant messages, chat room messages, electronic messages, information input via a web camera, and so forth. The data relating to the record may be input either with human interaction or by automatic prompting or even through unstructured questionnaires. In such questionnaires, the patient may be prompted to input a chief complaint or symptoms, medical events, and the like, with prompting from voice, textual or graphical interfacing. In one exemplary embodiment, for example, the patient may also respond to graphical depictions of the human body, such as for selection of symptomatic region of the body.

Other information may be gathered prior to the patient contact, such as biometric information. Such information may be used for patient identification and/or authentication before data is entered into the patient record. Moreover, remote vital sign diagnostics may be acquired by patient input or by remote monitors, if available. Where data is collected by voice recording, speech recognition software or similar software engines may identify key medical terms for later analysis. Also, where necessary, particularly in emergency situations, residential or business addresses, cellular telephone locations, computer terminal locations, and the like can be accessed to identify the physical location of a patient. Moreover, patient insurance information can be queried, with input by the patient to the extent such information is known or available.

Based upon the patient interactions 258, various system interactions 260 may be taken prior to the patient visit or contact. In particular, as the patient-specific data is acquired, data is accessed from the integrated knowledge base (including the various resources) for analysis of the patient information. Thus, the data may be associated or analyzed to identify whether appointments for visits are in order, if not already arranged, and such appointments may be scheduled based upon the availability of resources and facilities, patient preferences and location, and so forth. Moreover, the urgency of such scheduled appointments may be assessed based upon the information input by the patient.

Among the various recommendations which may be made based upon the analysis, pre-visit imaging, laboratory examinations, and so forth may be recommended and scheduled to provide the most relevant information likely to be needed for efficient diagnosis and feedback during or immediately after the patient visit. Such recommendations may entail one or more of the various types of resources described above, and one or more of the modalities within each resource. The various information may also be correlated with information in the integrated knowledge base to provide indications of potential diagnoses or relevant questions and information that can be gathered during the patient visit. The entire set of data can then be uploaded to the integrated knowledge base to create or supplement a patient history database within the integrated knowledge base.

As a result of the uploading of data into the integrated knowledge base, various types of structured data may be stored for later access and processing. For example, the most relevant captured patient data may be stored, in a structured form, such as by classes or fields which can be searched and used to evaluate potential recommendations for the procedures used prior to the medical visit, during the visit and after the visit. The data may be used, then for temporal analysis of changes in patient conditions, identification of trends, evaluation of symptoms recognized by the patient, and general evaluation of conditions which may not even be recognized by the patient and which are not specifically being complained of. The data may also include, and be processed to recognize, potentially relevant evidence-based data, demographic risk assessments, and results of comparisons and analyses of hypothesis for the existence or predisposition for medical events and conditions.

Following the system interaction, and resulting from the system interaction, various output-type functions may be performed by the system. For example, as noted at reference numeral 262 in FIG. 19, patient-specific recommendations may be communicated to the patient prior to the patient contact. These recommendations may include appointments for the contact or for other examinations or analyses, educational information relating to such procedures, protocols to be followed prior to the procedures (e.g. dietary recommendations, prescriptions, timing and duration of visits). Moreover, the patient information may be specifically tailored or adapted to the patient. In accordance with one aspect of the technique, for example, educational information may be conveyed to the patient in a specific language of preference based upon textual information available in the integrated knowledge base and the language of preference indicated by the patient in the patient record. Such instructions may further include detailed data, such as driving or public transportation directions, contact information (telephone and facsimile numbers, website addresses, etc.). As noted above, actions may include ordering and scheduling of exams and data acquisition.

A further output action which may be taken by the system prior to and on-site visit might include reports or recommendations for clinicians and physicians. In particular, the reports may include output based upon the indications and designation of symptoms experienced by the patient, patient history information collect, and so forth. The report may also include electronic versions of images, computer-assisted processed (e.g. enhanced) images, and so forth. Moreover, such physician reports may include recommendations or prioritized lists of information or examinations which should be performed during the visit to refine or rule out specific diagnoses.

The process summarized in FIG. 19 continues with information which is collected by patient interaction during a contact, such as an on-site visit, as indicated at reference numeral 264. In a present example, the information collected at the time of the contact might begin with biometric information which, again can be used for patient identification and authentication. The visit may thus begin with a check-in process in which the patient is either registered on-site or pre-registered off-site prior to a visit. Coordinated system interactions may be taken during this time, such as automatic access to the patient record established during the pre-visit phase. Additional information, similar to or supplementing the information collected prior to the visit may then be entered into the patient record. Patient conversation and inputs may be recorded manually or automatically during this interview process in preparation for a clinician or physician interview. As before, where voice data is collected, speech recognition engines may identify key medical terms or symptoms which can be associated with information in the integrated knowledge base to further enhance the diagnosis or treatment. Video data may similarly be collected to assess patient interaction, mental or physical state, and so forth. This entire check-in process may be partially or fully automated to make optimal use of institutional resources prior to actual interview with a clinician, nurse, or physician.

The on-visit may continue with an interview by a clinician or nurse. The patient conversation or interaction may again be recorded in audio or video formats, with complaints, symptoms and other key data being input into the integrated knowledge base, such as for identification of trends and temporal analysis of advancement of a condition or event. Again, and similarly, vital sign information may be updated, and the updated patient record may be evaluated for identification of trends and possible diagnoses, as well as or recommendations of additional medical procedures, as noted above.

The on-site visit typically continues with a physician or clinician interview. As noted above, during the on-site visit itself, analyses and correlations with information in the integrated knowledge base may be performed with reports or recommendations being provided to the physician at the time of the interview. Again, the reports may provide recommendations, such as rank-ordered proposals for potential diagnoses, procedures, or simply information which can be gathered directly from the patient to enhance the diagnosis and treatment. The interview itself may, again, be recorded in whole or in part, and key medical terms recognized and stored in the patient's record for later use. Also during the on-site visit, reports, recommendations, educational material, and so forth may be generated for the patient or the patient care provider. Such information, again, may be customized for the patient and the patient condition, including explanations of the results of examinations, presentations of the follow-up procedures if any, and so forth. The materials may further include general health recommendations based upon the patient record, interaction during the contact and information from the integrated knowledge base, including general reference material. The material provided to the patient may include, without limitation, text, images, animations, graphics, and other reference material, raw or processed, structured video and/or audio recordings of questions and answers, general data on background, diagnoses, medical regimens, risks, referrals, and so forth.

The form of such output may suit any desired format, including hardcopy printout, compact disk output, portable storage media, encrypted electronic messages, and so forth. As before, the communication may also be specifically adapted to the patient in a language of preference. The output may also include information on financial arrangements, including insurance data, claims data, and so forth.

The technique further allows for post-contact data collection and analysis. For example, following a patient visit, various patient interactions may be envisaged, as indicated generally at reference numeral 266 in FIG. 19. Such interactions may include general follow-up questions, symptom updates, remote vital sign capture, and the like, generally similar to information collected prior to the contact. Moreover, the post-contact patient interaction may include patient rating of an institution or care providers, assistance in filing or processing insurance claims, invoicing, and the like. Again, based upon such inputs, data is accessed, which may be patient-specific or more general in nature, from the integrated knowledge base to permit the information to the coordinated with patient records and all other available data to facilitate the follow-up activities, and to generate any reports and feedback both for the patient and for the care provider.

Integrated Knowledge Base Interface

Figure 20:
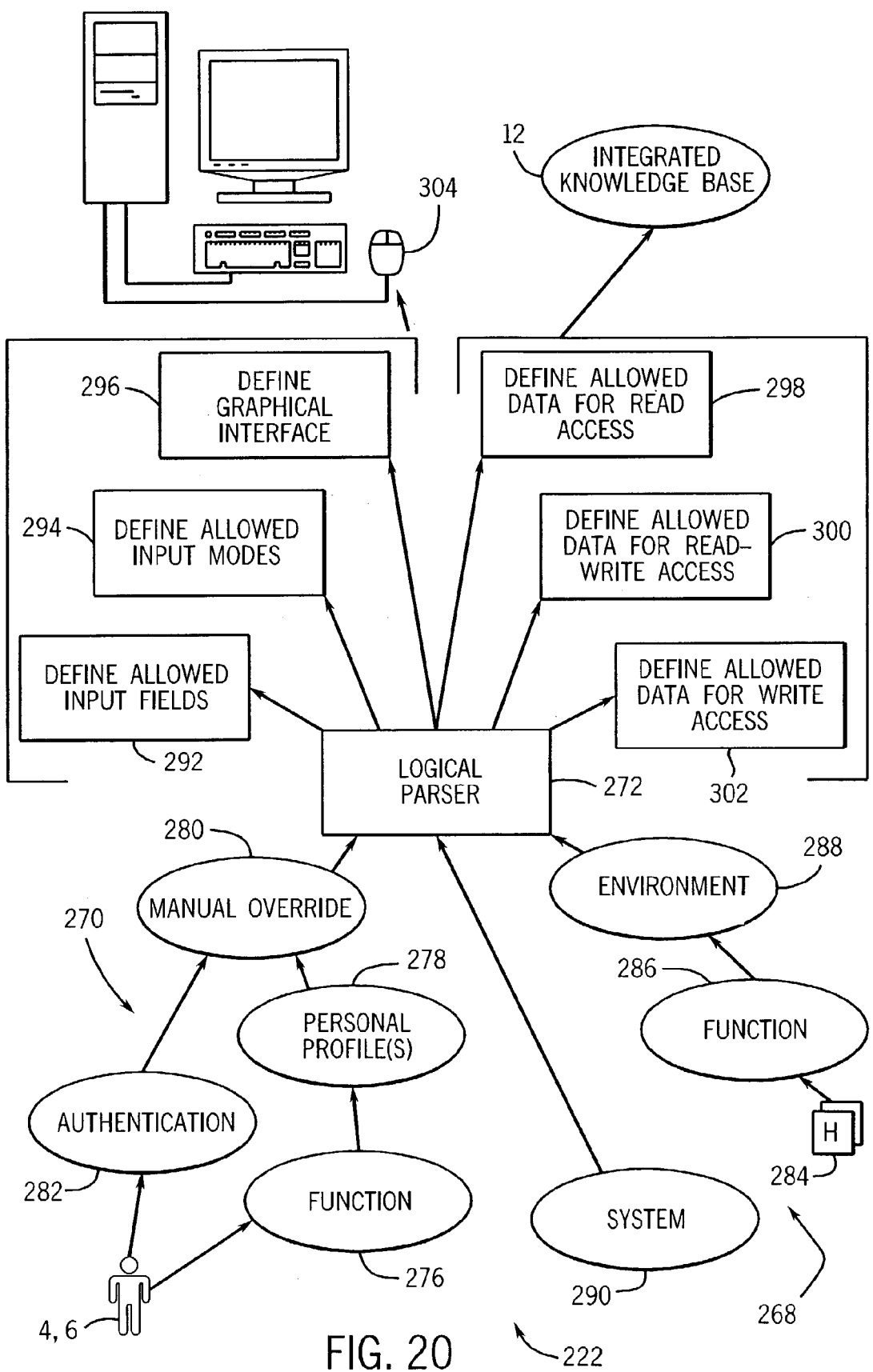
FIG. 20 is a diagrammatical representation of certain components and functions available for refining user access to the integrated knowledge base and for defining user-specific interfaces for interacting with the integrated knowledge base.

As noted above, the "unfederated" interface for the integrated knowledge base and, more generally, for the processing system and resources, may be specifically adapted for a variety of users, environments, functions, and the like. FIG. 20 generally illustrates an interface processing system which facilitates interactions with the integrated knowledge base. The system generally includes a series of input parameters or sources 270, which may be widely varied in nature, location, and utility. Based upon inputs from such sources, a logical parser 272, which may be generally part of the data processing system 10 described above, identifies interfaces and access of for interaction between users, hardware, and systems on one hand, and user workstations on the other, as well as access to the integrated knowledge base. The interface and access output functions, indicated generally at reference numeral 274, are then used to provide customized interfaces and access to the integrated knowledge base depending upon the inputs received by the parser.

As summarized in FIG. 20, input parameters or sources 270 may generally include parameters relating to users, including patients 4 and clinicians 6, as well as to any other users of the system, such as financial or insurance companies, researchers, and any other persons or institutions having the right to access the data. For user-initiated events, or any contact with the integrated knowledge base in which a user is involved, various access levels, functions, profiles, environments and the like may be considered in customizing the user interface and the level of access to the integrated knowledge base data and processing capabilities. By way of example, a radiologist reviewing an image or images at a review workstation, a technologist operating a CT scanner, or an administrator scheduling appointments or entering billing information may all be users to the system. The parameters or characteristics of the user which may be considered by the logical parser 272 may, as noted, vary greatly. In a present exemplary embodiment such characteristics include the function being performed by the user, as noted at reference numeral 276, as well as a personal profile of a user as noted at reference numeral 278. The information relating to functions and personal profiles may, where appropriate, be subject to a manual override as indicated at reference numeral 280 in FIG. 20. Moreover, all of the access by specific users may be filtered through various types of authentication as indicated in reference numeral 282.

In a typical scenario, a user may enter an authentication module, such as on a workstation 304, illustrated in FIG. 20, to enable secure access to the system. Where the function performed by the user is one of the criteria considered for interfacing and access, the user may be prompted to enter a current function, or the function may be recognized for the individual user profile. In this matter, the same user may have multiple functions in the system, such as in the case of thoracic radiologist at a hospital functioning as an interventionalist in one context and having additional functions as a mammographer at other periods, a manager at certain periods, and so forth. As a further example, a general practice nurse may function as a clinician at certain times, such as to input medical history information, and as an appointment scheduler at other times, and as a clerical person for input of billing, record data or insurance data at still other times. Each individual or institution, may customize one or more profiles containing personal preferences or information for each function. The profile may contain data about the user, and information describing the user interface preferences, if any, for different data access modes or functions.

Similarly, certain hardware or modality systems may have direct access to the integrated knowledge base, such as for uploading or downloading information useful in the analysis, processing, or data acquisition functions performed by the system. As illustrated in FIG. 20, such hardware, denoted generally by reference numeral 284, may include imaging systems, patient input stations, general purpose of computers linked via websites, and so forth. The hardware may interface with the parser by similar designation of one or more functions 286, in a matter similar to that described above for the users. Similarly, parameters such as the environment of the hardware, as indicated at reference numeral 288, may be considered. Such environments may provide an indication, for example, of where and how a system is used, such as to differentiate specific functionalities of imaging systems used in emergency room settings from those used in other clinical applications, mobile settings, and so forth. As will be appreciated by those skilled in the art, such function and environment information may influence the type and amount of data which can be accessed from or uploaded to the integrated knowledge base, and may be used, for example, in prioritization or processing of information from the integrated knowledge base depending upon urgency of treatment, and so forth.

A general system input 290 is also illustrated in FIG. 20, which may be considered by the logical parser. General system information may be relative to individual interfacing systems, including a system on which a user or piece of hardware interfaces with the knowledge base. By way of example, a system utilized by a user to interface with the knowledge base may, automatically or with user intervention, provide information relating to specific hardware devices, parameters, system capabilities, functions of the device, environments in which the devices are located or used, and so forth. Such information may indicate, for example, that a device is used as an image review workstation, such that different default interface characteristics may be employed in a radiology reading room and in an intensive care unit. Such interface characteristics may offer unique advantages, such as different presentation modes for similar data, customized resolution and bandwidth utilization, and so forth.

Based upon the information provided to the logical parser 272, the parser determines appropriate user interface definitions, as well as definitions of access to the integrated knowledge base. Among the determinations made by the logical parser 272, may be allowable data state changes which can be initiated by the user, hardware or system, allowed methods and fields for data input and output, defined graphical or other (e.g. audio) presentation modes, and so forth. In providing such definition, the logical parser may draw upon specific levels or classifications of access, as well as upon specific pre-defined graphical interfaces or other fields, which are utilized in formulating the interfaces. In particular, for a given knowledge base request, the logical parser 272 may utilize algorithms embedded within the knowledge base interface software, pre-defined sets of instructions from an interface manager, or self-learning algorithms, in addition to such pre-defined access and interface configurations. Where a user is allowed to manually override characteristic data or configurations, the logical parser may customize the interface or given application or function. For example, an individual user may utilize a review workstation 304 in an intensive care unit to review a trauma case, but utilizing default emergency room settings by overriding the intensive care unit settings. A wide variety of other definitional functions and overrides may be envisioned, all permitting standard and customized interfaces and access levels to the integrated knowledge base.

Among the functions defined by the logical parser are certain functions for defining the user interface, and other functions for defining access to the integrated knowledge base. As illustrated in FIG. 20, such functions may include a definition of allowed input fields, as illustrated at reference numeral 292. Such fields may, in the context of a graphical user interface, be shown, not shown, or "grayed out" in a particular user interface, depending upon the factors discussed above. In addition, allowed input modes, as indicated at reference numeral 294, may be defined, again allowing various types of input, such as through the display or non-display of specific input pages, interactive web pages, and so forth. Similarity, specific graphical interfaces may be defined by the logical parser as indicated at reference numeral 296. It should be noted, that the various interface fields, modes, and presentations identified by the logical parser based upon the input information may be stored remotely, such as in the processing system or system data repository, or locally in a management system or within a workstation 304 itself.

The logical parser may also define specific levels of interaction or access which are permitted between users, systems, and hardware on one hand, and the integrated knowledge base on the other. Such access control may define both the accessing of information from the knowledge base, and the provision of information to the knowledge base. The access control may also define the permitted processing functions associated with the knowledge base via the data processing system. In the examples illustrated in FIG. 20, such functions may include defining allowed data for read access, as indicated at reference numeral 298, defining allowed data for read-write access, as indicated at reference numeral 300, and defining allowed data for write access, as indicated at reference numeral 302.

As noted above, the interface processing system 268 permits various types of authentication to be performed, particularly for users attempting to gain access to the integrated knowledge base. This authentication function may be achieved in a range of manners, including by password comparisons, voice recognition, biometrics, script or files contained within an interface device (e.g. a "cookie") or password file, and so forth. Because a wide range of diverse data may be included in the integrated knowledge base, authentication and security issues can be the focus of specific software and devices to carefully guard access and avoid tampering or unauthorized access. Thus, in addition to the use of standard user authentication protocols, data encryption techniques for knowledge communicated to and from the knowledge base may be employed, and associated infrastructure may be offered at input sides and output sides of the interface.

In general, a user may be responsible for setting the security or access level for data generated or administrated by that user, or other participates may be responsible for such security and access control. Thus, the system can be programmed to implement default access levels for different types of users or user functions, as noted above. Moreover, different privacy levels may be set by a user for different situations and for other users. Specifically, a patient or primary care physician may be in a best position to set access to his or her medical data, such that a specific set of physicians or institutions can access the information, depending upon their need. Access can also be broadened to include other physicians and institutions, such as in the event of accident or incapacitation of a patient. Moreover, access levels can be sorted by individual, situation, institution, and the like, with particular access levels being implemented in particular situations, such as in case of emergency, for clinical visits, during a transfer of control or oversight to an alternative physician during periods of a vacation, and so forth.

In general, the authentication and security procedures may be implemented through software which may question a patient and implement defaults based upon the responses. Thus, a patient may be prompted for classes of individuals, insurance companies, primary care physicians and specialists, kin, and the like, as well as for an indication of what level of access is to be provided to each class. Parsing and access to the information, as well as customization of the interfaces may then follow such designations.

Certain inherent advantages flow from the interface system described above. By way of example, an individual patient can become, effectively, a data or case manager granting access to information based upon the patient's desires and objectives. The mechanism can also be customized, and easily altered, for conformance with local, state and federal or other laws or regulations, particularity those relating to access to patient data. Such regulations may also relate to access to billing and financial information, access by employers, disability information, access to and for insurance claims, Medicare and Medicaid information, and so forth. Moreover, the technique offers automatic or easily adapted compliance with hospital information system data access regulations, such that data can be flagged to insure privacy based upon the user or access method. Finally, the technique provides for rapid and convenient setting, such as by the patient or a physician, of privacy levels for a broad range of users, such as by class, function, environment, and so forth.

Multi-Level System Architecture

As described generally above, the present techniques offer input, analysis, processing, output and general access to data at various levels, for various users, and for various needs. In particular, the system offers the capability of providing various levels of data access and processing, with all of the various levels generally being considered as contributing to, maintaining, or utilizing portions of the integrated knowledge base and functionality described herein. The various levels, rising from a patient or user level may include workstations, input devices, portions of the data processing system, and so forth which contribute the needed data and which extract needed data for the functionality carried out at the corresponding level. Where levels in the system architecture can satisfy the users needs, such as within a specific institution, insurance company, department, region, and so forth, sharing and management of data may take place solely at such levels. Where, however, additional functionality, is desired, the system architecture offers for linking the lower and any intermediate levels as necessary to accommodate such functionality.

Figure 21:
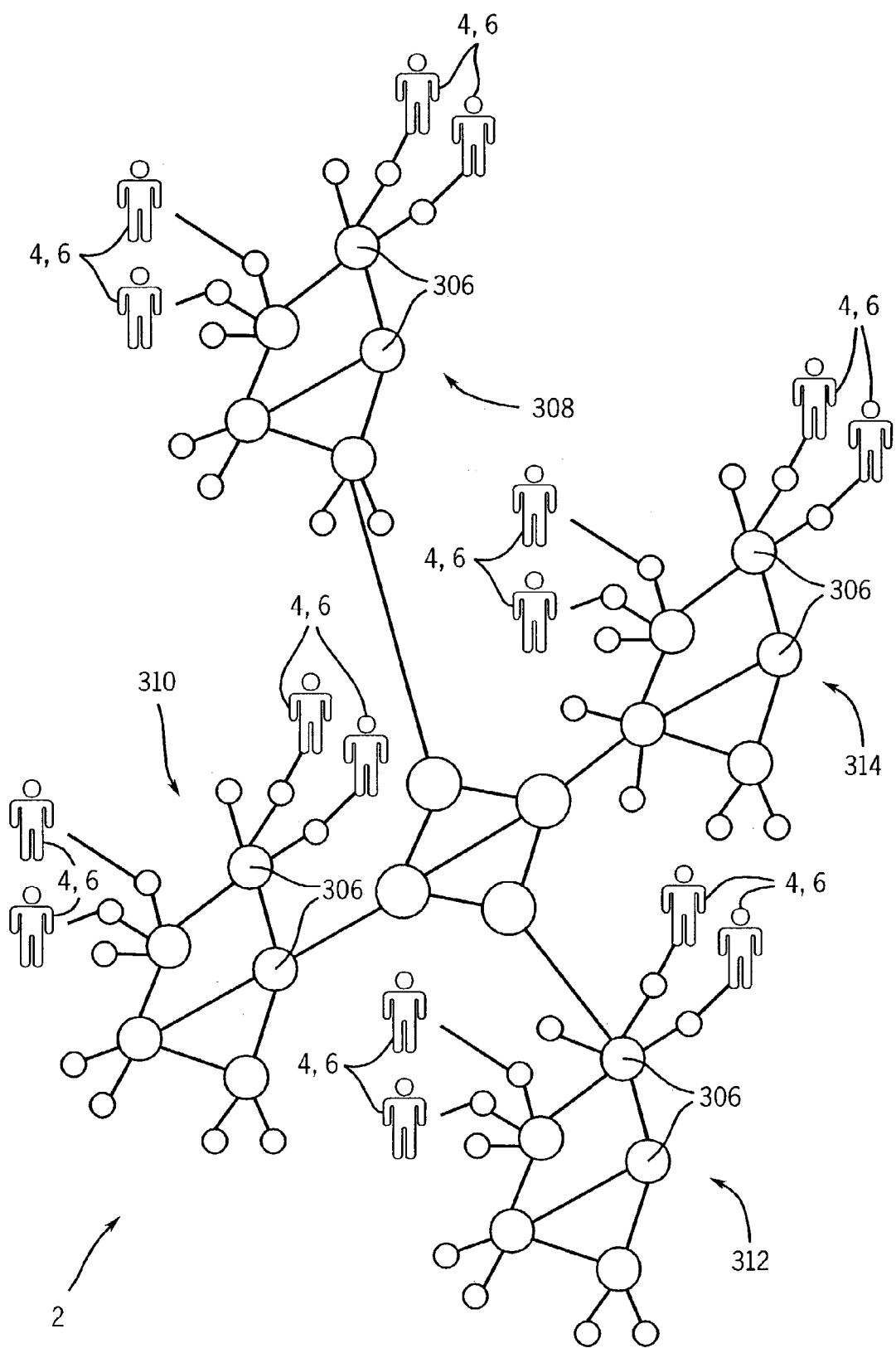
FIG. 21 is a diagrammatical representation of levels in a clustered architecture implemented in aspects of the present technique.
Figure 22:
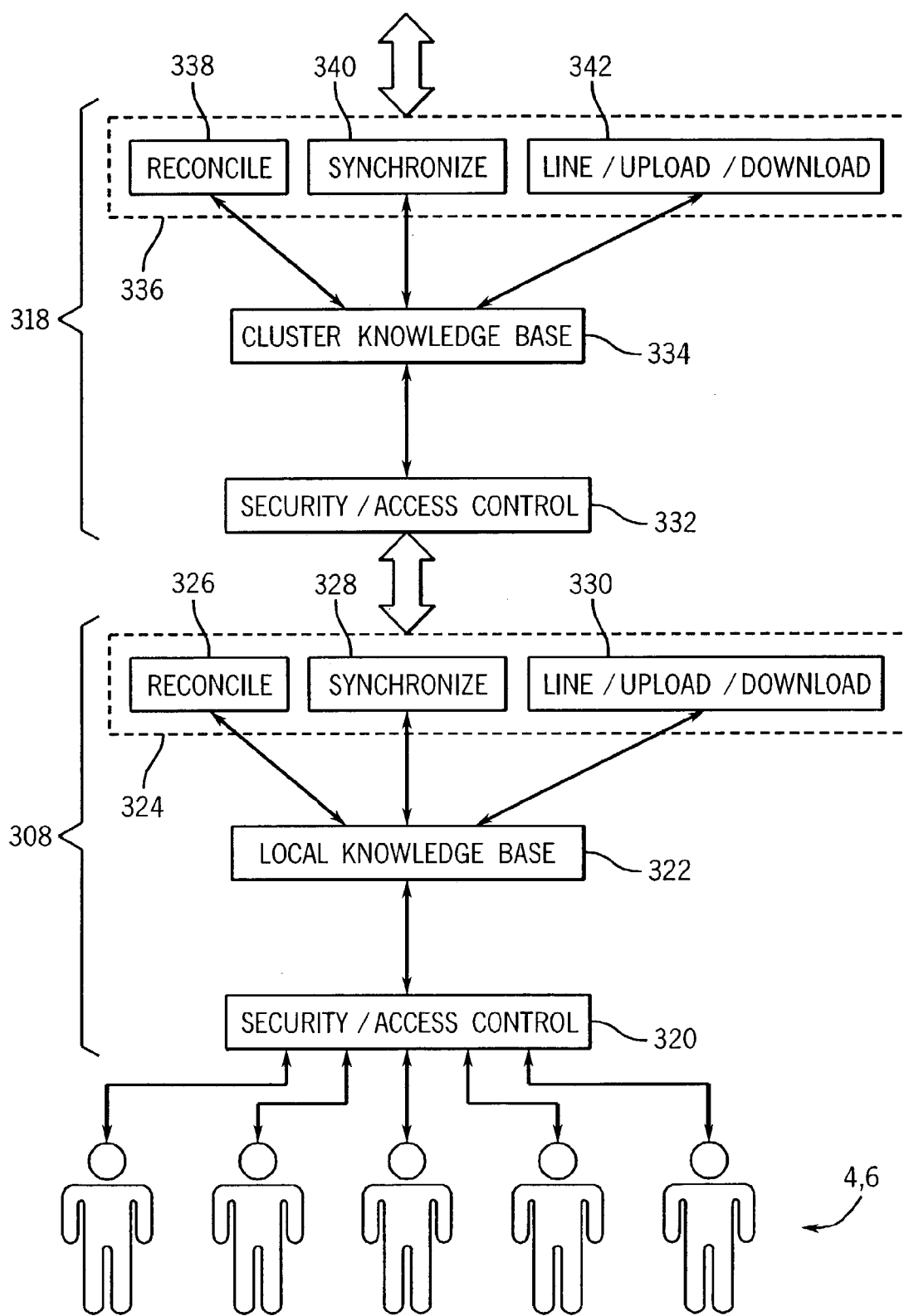
FIG. 22 is flowchart illustrating various functions carried out at different levels of the architecture of FIG. 21.

FIGS. 21 and 22 generally illustrate exemplary architectures and management functions carried out in accordance with such multi-level architectures. FIG. 21 illustrates the present data exchange system 2 as including a number of integrated levels and clusters of input and output stations or users. The users, which would typically be patients 4 or clinicians 6 (including radiologists, nurses, physicians, management personnel, insurance companies, research institutions, and so forth) reside at fundamental or local level 306. As noted above, various functionalities may be carried out at such local levels, including tailoring of data input and output functions, access control, interface customization, and so forth. Within a local group or cluster level 308, then, such users may communicate with one another and with system elements of the type described above. That is, each local group or cluster level 308 may include any or all of the various resources discussed above, including both data resources and controllable and prescribable resources. In a practical implementation, a local group or cluster level 308 may include, by way of example, departments within a particular institution, institutions affiliated in some way, institutions located in a specific geographical region, institutions linked by virtue of their practice area or specialization, and so forth. The linking of the users and components at such local group or cluster levels, then, permits specific functions to be carried out, to the extent possible, fairly locally and without the need to access remote data resources or other local groups or clusters.

Similar remote groups or clusters may then be linked, and may be similar or generally similar internal structures, as indicated at reference numerals 310, 312, and 314 in FIG. 21. It should be noted, however, that each of such clusters may vary widely in size, character, and even in its own network architecture, depending upon the needs and functions of the users within the group or cluster. The various local groups and cluster levels, then, may be linked by one or more central clusters as indicated generally at reference numeral 318.

Although a "centralized/decentralized" system architecture is generally illustrated in FIG. 21, it should also be borne in mind that the functionality of the multi-level system offered by aspects of the present technique may take on various analytical forms. That is, any or all of available network architectures, including centralized architectures, ring structures, hierarchical structures, decentralized structures, centralized structures, and combinations of these may reside at the various levels in the overall system. Moreover, the various remote groups or clusters may, where desired, be linked to one another in alternative fashions without necessarily passing through a central group or cluster. Thus, preferential links between specific institutions or practitioners may be provided such that a "virtual cluster" is defined for the exchange of data and processing of data. Such links may be particularly useful where special relationships or repetitive operations are carried out between such users.

The functions described above, including the data acquisition, processing, analysis, and other functions may be carried out at specific workstations within the architecture of FIG. 21, within local groups or clusters, or by use of more expanded resources incorporating one or more remote group or cluster. Certain of these functions, according to the multi-level architecture scenario, are generally illustrated in FIG. 22. As shown in FIG. 22, certain functions may be carried out at local group or cluster levels 308, with generally similar functions being carried out at higher levels 318. Again, it should be noted that the same or similar functions may even be carried out at an individual terminal or workstation, and that further levels may be provided in the architecture.

As illustrated in FIG. 22, users 4, 6 may be linked to the system and inputs and access filtered through a security/access control modules 320. As noted above, such modules may employ various forms of security and access control, such as based upon passwords, voice recognition, biometrics, and more sophisticated techniques. In general, the modules 320 will maintain a desired level of assurance that those linking to the network have rights to the specific data to be uploaded, downloaded, or processed. The modules 320 allow the users to gain access to a local knowledge base 322 which, from a general standpoint, may be considered to be part of the integrated knowledge base discussed above. It should also be noted that the local knowledge base 322 may also incorporate features of a federated database as discussed above wherein certain data may be pre-processed or translated for use by the programmed functionalities.

A validation or data management module 324 will typically be provided in some form to control access to and quality of data within the local knowledge base 322 and data from the other components of the overall system. That is, certain data, particularly that data which is used at a local level, may be preferential stored within the local knowledge base 322. However, where the overall system functionality requires, such data may be uploaded to higher levels, or to piers in other local groups or clusters. Similarly, data may be downloaded or processed from other remote sources. To maintain the validity and quality of such data, the validation and data management module 324 may carry out specific functions, typically bi-directionally, as indicated in FIG. 22. Such functions may include those of the reconciliation modules as indicated at reference numeral 326, which can reconcile or validate certain data, such as based upon time of entry, source of the data, or any other validating criteria. Where such reconciliation or validation is not available, such as due to conflicting updates or inputs, such matters may be flagged to a user for reconciliation. A synchronizer module 328 provides, similarly, for synchronizing records between the local knowledge base 322 and remote resources. Finally, a link-upload/download module 330 provides for locating, accessing, and either storing up or downloading from other memories or repositories for the data from the local knowledge bases.

Generally similar functionality may be carried out, then, at other levels or within other relationships, as indicated generally by 318 in FIG. 22. Thus, as between local groups or clusters, security and access control modules 332 may, in conjunction with modules 320, provide secure access to data from other users, groups, clusters or levels. Moreover, cluster knowledge base 334 may be maintained which compliment, or even replicate some of the local knowledge base data. As with the local knowledge base 322, the cluster knowledge base 334 may be generally considered to be part of the overall integrated knowledge base. Other functions may be performed at such higher levels as well. Thus, as indicated at reference numeral 336, validation and data management modules may be implemented which, again, may be coordinated with the functionality of similar modules 324 at local levels. Such modules may, again, include reconciler modules 338, synchronizer modules 340 and link/upload/download modules 342 which facilitate exchange of data between groups or clusters.

The multi-level architecture described above offers significant advantages and functionalities. First, data may be readily accessed by specific members of groups or clusters with specifically-tailored access control functions. That is, for such functions as insurance billing, clinical analysis, and so forth, reduced levels of securities may be provided within a specific group or cluster. Access to data by other users in other groups or clusters, then, may be more regulated, such as by application of different security or access control mechanisms. Moreover, certain functionalities may be provided at very basic levels, such as at patient or clinician workstations, with additional access to data and processing capabilities being linked as necessary.

Moreover, it should be noted that in presently contemplated embodiments, the overall network topology tends to mirror the underlying data structure which in itself mirrors and facilitates computer-assisted data operation algorithms discussed below. That is, where functionality or data are related by specific relationships, processing needs, access needs, validation needs, and so forth, the establishment of groups or clusters may follow similar structures. That is, as noted above, "typical" access, use, needs, and functionalities may reside at more or less tight nodes or clusters, with more distant or infrequent structures or functionalities being more distributed.

The linking of various clusters or groups also permit functionalities to be carried out that were heretofore unavailable in existing systems. For example, analysis for trends, relationships and the like between data at various groups or cluster levels may be facilitated which can aid in identifying traditionally unavailable information. By way of example, where a specific prevalence level of a disease state occurs at a specific institution, department within an institution, or a geographic region, existing systems tend to not recognize or belatedly recognize any relationship between such occurrence and similar occurrences in other locations. The present system, on the other hand, permits such data to be operated upon, mined, analyzed, and associated so as to easily and quickly recognize the development of trends at various locations and even related by various data, such as quality of care, and so forth. Thus, coordinated access and analysis of peer information is available for identification of such disease states in overall population.

Similarly, resource management may be improved by) the multi-level architecture offered by the present technique. In particular, trends, both past and anticipated in inventory use, insurance claims, human resource needs, and so forth may also be identified based upon the availability of data and processing resources at the various levels described above.

Patient-Oriented Medical Data Management

Figure 23:
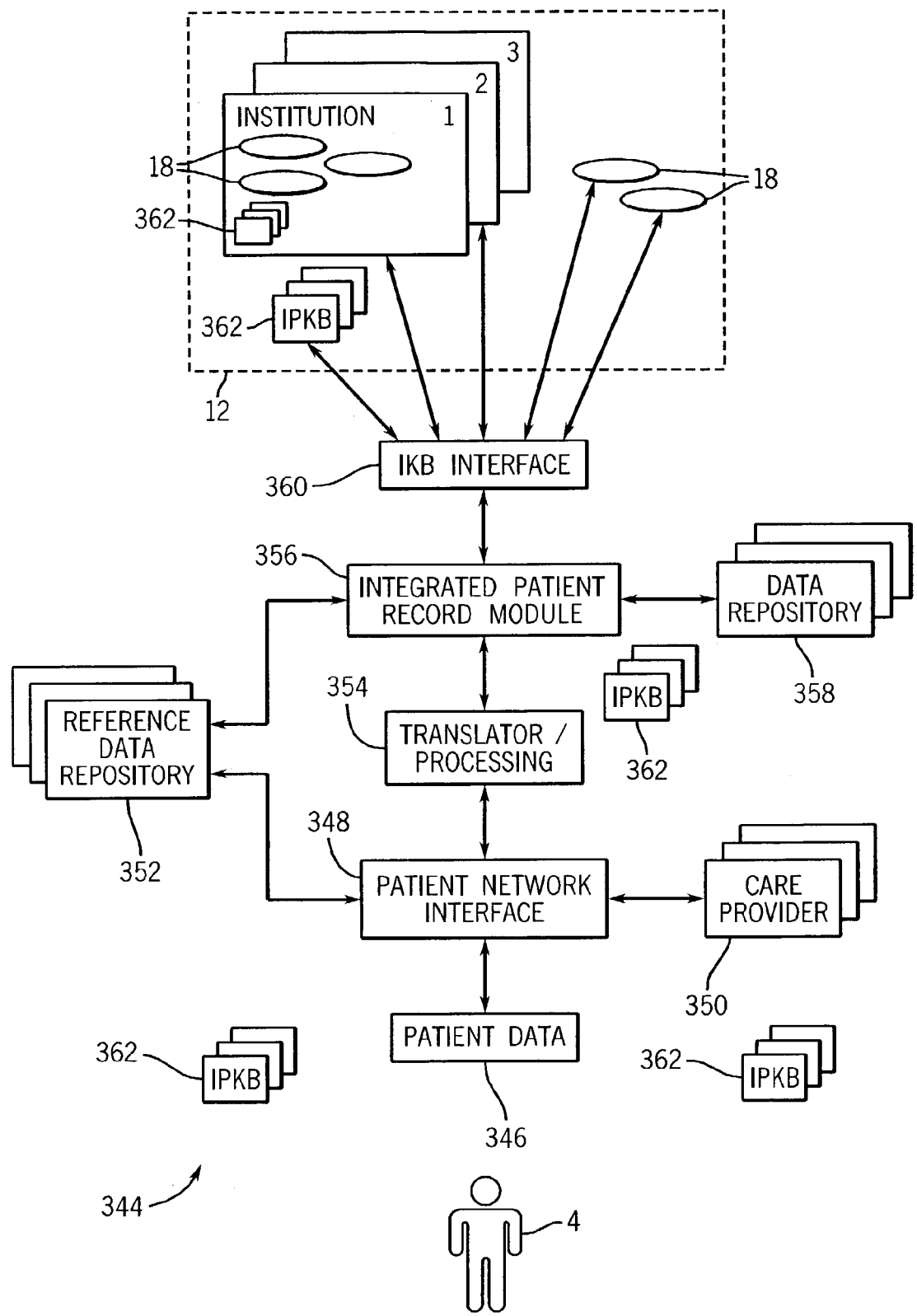
FIG. 23 is a flowchart illustrating components and processes in a patient-managed integrated record system.

The present technique offers further advantages in the ability of patients to be informed and even manage their own respective medical care. As noted above, the system can be integrated in such a manner as to collect patient data prior to medical contacts, such as office visits. The system also can be employed to solicit additional information, where needed, for such interactions. Furthermore, the system can be adapted to allow specific individualized patient records to be maintained that may be controlled by the individual patient or a patient manager. FIG. 23 generally represents aspects of the technique designed for creation and management of integrated patient records.

As shown in FIG. 23, the arrangement of functionalities and modules may be referred to generally as a patient-management knowledge base system 344, which at least partially includes features of the integrated knowledge base and other techniques described above. A patient 4 provides patient data, as indicated generally at reference numeral 346 in FIG. 23. The patient data may be provided in any suitable manner, such as via hard copies, analysis of tissue samples, input devices at institutions or clinics, or input devices which are individualized for the patient. Such input devices may include, for example, devices which are provided to, worn by, implanted in, or directly implemented by the patient as at the patient's home or place of employment. Thus, the patient data 346 may be provided by mobile samplers (e.g. for blood analysis), sensing systems for physiological data (e.g. blood pressure, heart rate, etc.). The patient data may be stored locally, such as within the sensing device or within a patient computer or workstation. Similarly, the patient data may be provided either at the prompting of the patient or through system prompting, such as via accessible Internet web pages. Further, patient data may be extracted from external resources, including the resources of the integrated knowledge base as described more fully below. Thus, the patient data, in implementation, may be exchanged in a bi-directional fashion such that the patient may provide information to the record and access information from the record. Similarly, the patient may manage input to the record of data from outside resources as well as manage access to output of the record to outside resources.

The patient data is exchanged with other element of the system via a patient network interface 348. The patient network interface may be as simple as a web browser, or may include more sophisticated management tools that control access to, validation of, and exchange of data between the patient and the outside resources. The patient network interface may communicate with a variety of other components, such as directly with care providers as indicated at reference numeral 350. Such care providers may include primary care physicians, but may also include institutions and offices that store patient clinical data, and institutions that store non-clinical data such as insurance claims, financial resource data, and so forth. The patient network interface 348 may further communicate with reference data repository 352. Such reference data repositories were discussed above with general reference to the integrated knowledge base. The repositories 352 may be the same or other repositories, and may be useful by the patient network interface for certain processing functions carried out by the interface, such as comparison of patient data to known ranges or demographic information, integration into patient-displayed interface pages of background and specific information relating to disease states, care, diagnoses and prognoses, and so forth. The patient network interface 348 where necessary, may further communicate with a translator or processing module as indicated generally at reference numeral 354. The translator and processing modules may completely or partially transform the accessed data or the patient data for analysis and storage. Again, the translator and processing functions may be bi-directional such that they may translate and process both data originating from the patient and data transferred to the patient from outside resources.

An integrated patient record module 356 is designed to generate an integrated patient record, as represented generally by reference numeral 362 in FIG. 23. As used in the present context, the integrated patient record may include a wide range of information, both acquired directly from the patient, as well as acquired from institutions which provide care to the patient. The record may also include data derived from such data, such as resulting from analysis of raw patient data, image data, and the like both by automated techniques and by human care providers, where appropriate. Similarly, the integrated patient record may include information incorporated from reference data repositories 352. The integrated patient record module preferably stores some or all of the integrated patient record 362 in one or more data repository 358.

As noted above, the system 344 permits creation of an integrated patient record 362 which may include a wide range of patient data. In practice, the integrated patient record, or portions of the patient record, may be stored at various locations, such as at a patient location as indicated adjacent to the patient data block 346, at individual care providers (e.g. with a primary care physician) as indicated adjacent to block 350, or within a data repository 358 accessed by the integrated patient record module 356. It should also be noted that some or all of the functionality provided by the patient network interface 348, the translator and processing module 354 and the integrated patient record module 356 may be local or remote to the patient. That is, software for carrying out the creation and maintenance of the patient record may be stored direct at a patient terminal, or may be fully or partially provided remotely, such as through a subscription service. Similarly, the patient record repository 358 may be local or remote from the patient.

The integrated patient record module 356 also is preferably designed to communicate with the integrated knowledge base 12 via an integrated knowledge base interface 360. The interface 360 may conform to the general functionalities described above with respect to access, validation, tailoring for patient needs or uses, and so forth. The integrated knowledge base interface 360 permits the extraction of information from resources 18, which may be internal to specific institutions as indicated in FIG. 23. The interface also permits data from the patient to be uploaded to such resources and institutions. As also noted in FIG. 23, the integrated patient record 356, fully or in part, may be stored generally within the integrated knowledge base 12 to facilitate access by care providers, for example. The record may also be stored within individual institutions, such as within a hospital or clinic which has or will provide specific patient care.

The system functionality illustrated in FIG. 23 offers significant advantages. By way of example, as noted above, the access to specific information and the creation of records may be controlled and regulated more directly by a patient. That is, the system serves as an enabler for empowering the patient with respect to proactive management of medical records. Such interaction may take the form of patient-controlled access to portions of the patient record provided to specific care providers. Similarly, the system offers the potential for improving the education of the patient as regards to general questions as well as specific clinical and non-clinical issues. The system also provides a powerful tool for accessing patient data, including raw data, processed data, links, updates, and so forth which may be used by care providers for identifying and tracking patient conditions, scheduling patient care visits, and so forth. Such functions may be provided by "push" or "pull" exchange techniques, such as on a timed basis, or through notifications, electronic messages, wireless messages, and so forth. Direct interaction with the patient may include, therefore, uploading of patient data, downloading of patient data, prescription reminders, office visit reminders, screening communications, and so forth. Moreover, the integration of the patient data with other functionality and data from other resources permits the integrated patient record to be created and stored periodically or in advance of specific needs by the patient or by an institution, or compiled at the time of a specific query by linking to and accessing data for response to the query.

Predictive Modeling

The present technique, by virtue of the high degree of integration of the data storage, access and processing functions described above, provides a powerful tool for development of predictive models, both clinical and non-clinical in nature. In particular, data can be drawn from the various resources in the integrated knowledge base or a federated data base, processed, and analyzed to improve patient care by virtue of predictive model development. The development of such predictive models can be fully or partially automated, and such modeling may serve to adapt certain computer-assisted functions of the types described above.

Figure 24:
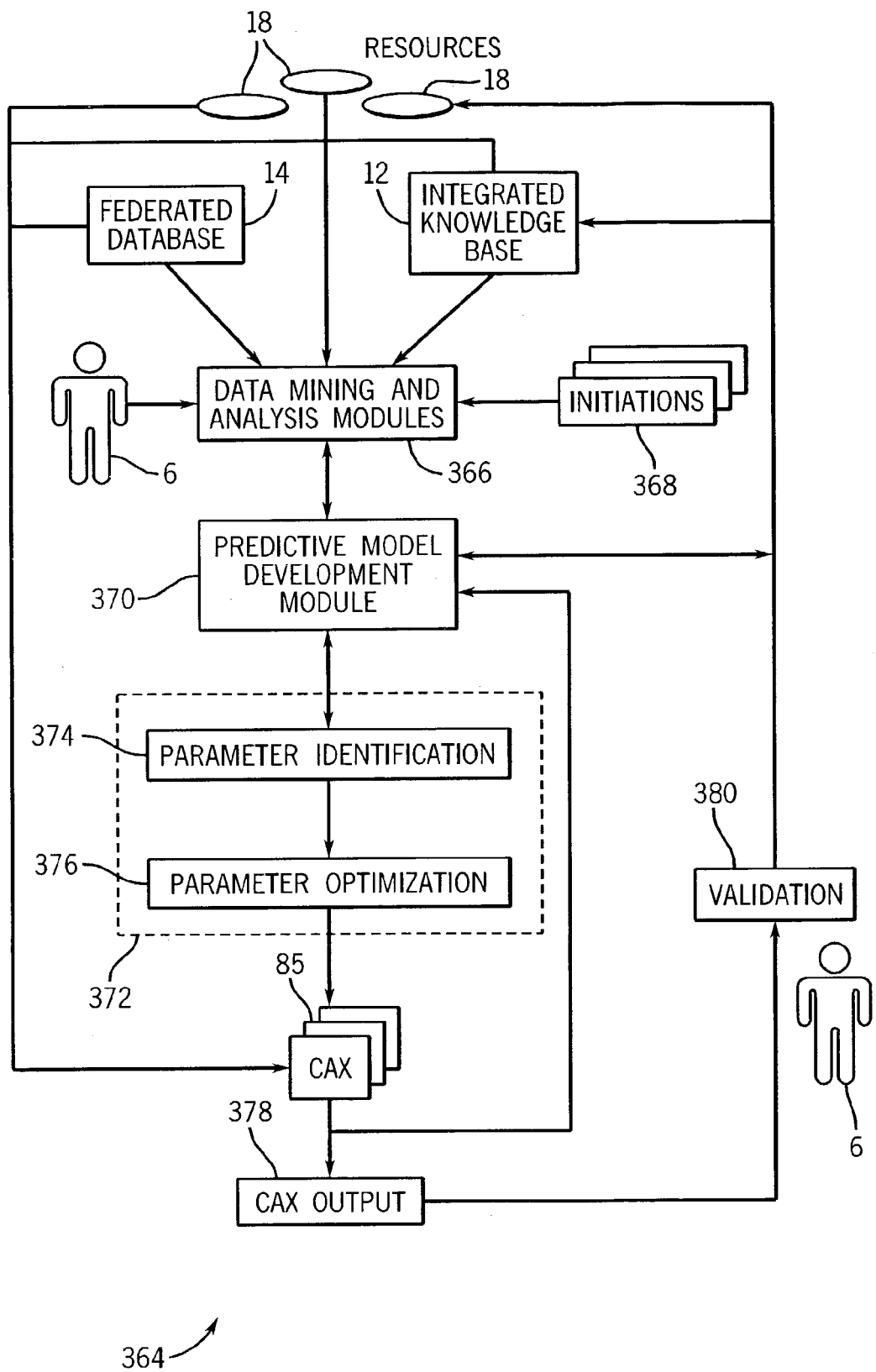
FIG. 24 is a flowchart illustrating exemplary components and steps in a predictive model development system.
Figure 25:
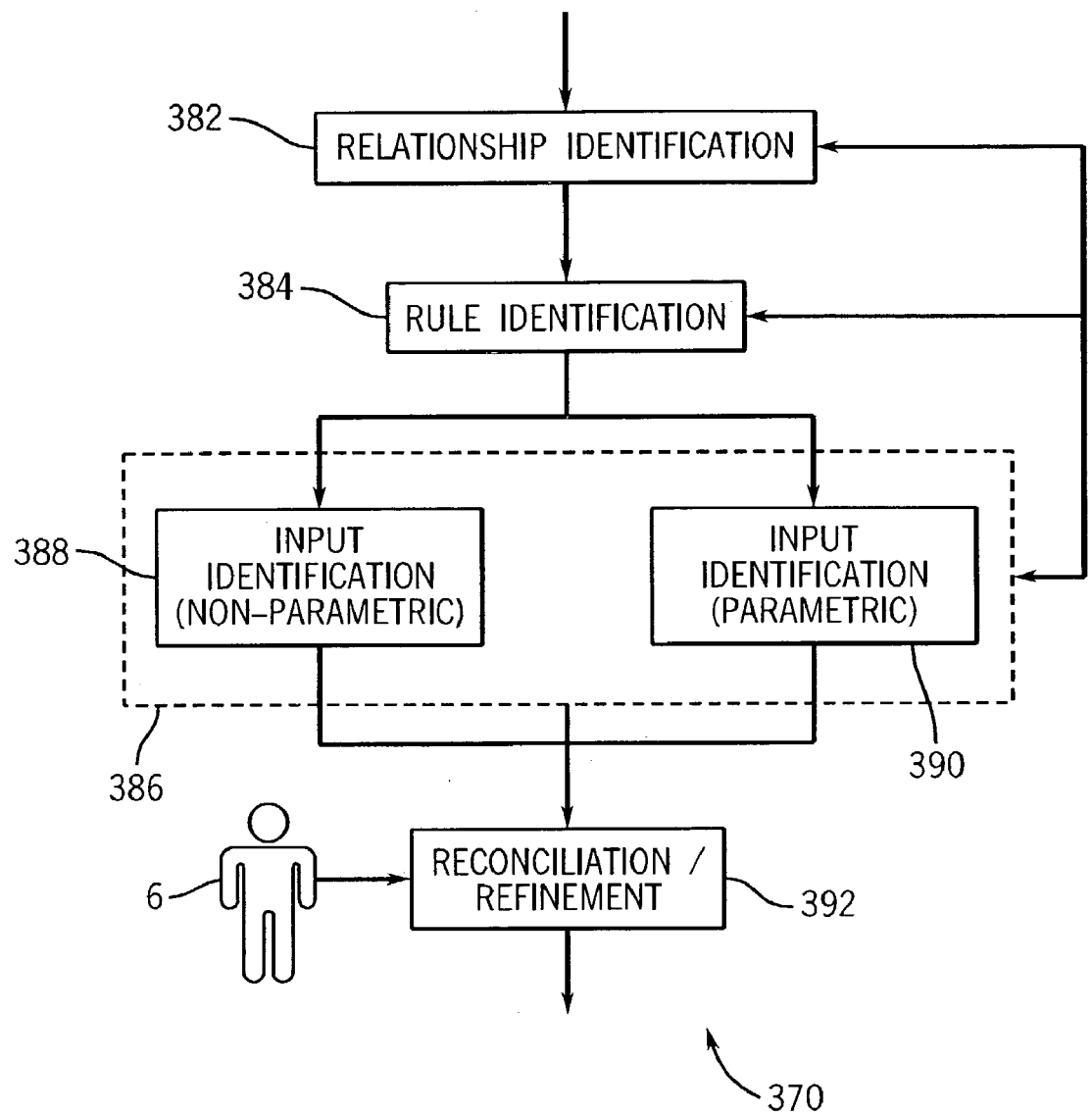
FIG. 25 is a flowchart illustrating functions carried out in a predictive model development module of the type illustrated in FIG. 24.

FIGS. 24 and 25 generally illustrate aspects of predictive model development which may be implemented in accordance with aspects of the present technique. FIG. 24 represents a predictive modeling system 364 that may be built upon or compliment the integrated knowledge base and network functions described above. The predictive modeling system 364 draws upon the resources 18, both data resources and controllable and prescribable resources, as well as upon any federated databases 14 provided in the system and upon the integrated knowledge base 12, which again may be centralized or distributed in nature. The system 364 relies upon software identified in FIG. 24 as data mining and analysis modules 366 designed to extract data from the various resources, knowledge bases and databases, and to identify relationships between the data useful in developing predictive models. The analysis performed by the data mining and analysis modules 366 may be initiated in any suitable manner, as indicated by the initiators block 368 in FIG. 24, including any or all of the initiating events outlined above with reference to FIG. 18. Once processing is initiated, the modules search for and identify data which may be linked to specific disease states, medical events, or to yet unidentified or unrecognized disease states or medical events. Moreover, the modules may similarly seek non-clinical data for development of similar models, such as for prediction of resource needs, resource allocation, insurance rates, financial planning, and so forth. It should be noted that the data mining and analysis functions performed by the modules 366 may operate on "raw" data from the resources and databases (again both clinical and non-clinical), as well as on filtered, validated, reduced-dimension, and similarly processed data from any one of these resources. Moreover, initiation of such processing, or validation of data may be provided by an expert, such as a clinician represented at reference numeral 6 in FIG. 24.

Based upon the mining an analysis performed by modules 366, a predictive model development module 370 further acts to convert the data and analysis into a representative model that can be used for diagnostic, planning, and other purposes. In the clinical context, a wide range of model types may be developed, particularly for refinement of computer-assisted processes referred to above. As noted above, these processes, referred to here in as CAX processes, permit powerful computer-assisted work flow such as for acquisition, processing, analysis, diagnostics, and so forth. The methodologies employed by the predictive model development module 370 may vary depending upon the application, the data available, and the desired output. In presently contemplated embodiments, for example, the processing may be based upon regression analysis, decision trees, clustering algorithms, neural network structures, expert systems, and so forth. Moreover, the predictive model development module may target a specific disease state or medical condition or event, or may be non-condition specific. Where data is known to relate to a specific medical condition, for example, the model may consist in refinement of rules and procedures used to identify the likelihood of occurrence of such conditions based upon all available information from the resources and knowledge base. More generally, however, the data mining and analysis functions, in conjunction with the model development algorithms, may provide for identification of disease states and relationships between these disease states and available data which were not previously recognized.

In applications where the predictive model development module 370 is adapted for refinement of a computer-assisted process CAX, the model may identify or refine parameters useful in carrying out such processes. The output of the module 370 may therefore consist of one or more parameters identified as relating to a specific condition, event or diagnosis. Outputs from the predictive model development module 370, typically in the form of data relationships, may then be further refined or mapped onto parameters available to and used by the CAX processes 85 illustrated in FIG. 24. In a presently contemplated embodiment, therefore, a parameter refinement function 372 is provided wherein parameters utilized in the CAX processes 85 are identified, as indicated at reference numeral 374, and "best" or optimized values or ranges of the values are identified or as indicated at reference numeral 376. The parameters and their values or ranges are then supplied to the CAX process algorithms for future use in the specific process. As a general rule, the CAX processes produce some output as indicated at reference numeral 378.

It should be noted that various functions performed and described above in the predictive modeling system 364 may be performed on one or more processing systems, and based upon various input data. Thus, as mentioned above, the integrated knowledge base and therefore the data available for predictive model development is inherently expandable such that models may be developed differently or enhanced as improved or additional information is available. It should also be noted that the various components of the system illustrated in FIG. 24 provide for highly interactive model development. That is, various modules and functions may influence one another to further improve model development.

By way of example, where a predictive model is developed by module 370 based upon specific data mining, the model development module may identify that additional or complimentary data would also be useful in improving the performance of the CAX processes. The model development module may then influence the data mining and analysis function based upon such insights. Similarly, the identification of parameters and parameter optimization carried out in the parameter refinement process can influence the predictive model development module. Furthermore, the results of the CAX process 85 can similarly affect the predictive model development module, such as for development or refinement of other CAX processes.

The latter possibility of interaction between the components and functions illustrated in FIG. 24 is particularly powerful. In particular, it should be recognized that the predictive model development module 370 may, in some respects, itself serve as a CAX process 85, such as for recognizing relationships between available data and matching such relationships to potential disease states, events, resource needs, financial considerations, and so forth. The process is not limited to any particular CAX process, however. Rather, although model development may focus on the diagnosis of a disease state, for example, the output of the CAX process (e.g. computer-assisted diagnosis or detection) may give rise to improvements in processing and modeling of desired processing of data. Similarly, the results of the CAX process in processing may lead to recognition of improvements in a model implemented for computer-assisted acquisition (CAA) of data. Other computer-assisted processes, including computer-assisted assessment (CAAx) of health or financial states, prognoses, prescriptions, therapy, and other decisions may similarly be impacted both by the predictive model development module, and by feedback from refined other processes.

As illustrated in FIG. 24, certain steps involved in development of clinical and non-clinical predictive models may be subject to validation or input from elements of the system or from experts. Thus, the CAX output 378 would typically be reviewed by an expert 6. Similarly, CAX output which may influence the predictive model development module 370 is preferably subject to validation as indicated at block 380 in FIG. 24. Such validation may be performed by the system itself (such as by cross-checking data or algorithm output, or by one or more experts). The output of the validation may then be linked to the resources, including the original resources themselves 18, and the integrated knowledge base 12. For example, it may be useful to link or pre-process certain data, or flag certain data for use in the CAX processes implemented by the developed model.

In use, the developed or improved model will typically be available for remote processing or may be downloaded to systems, including computer systems, medical diagnostic imaging equipment, and so forth, which employ the model for improving data acquisition, processing, diagnosis, decision support, or any of the other functions served by the CAX process. During such implementation, and as described above, the implementing system may access the integrated knowledge base, the federated database, or the originating resources themselves to extract the data needed for the CAX process.

Within the predictive model development module 370 several functions may be resident and carried out either on a routine basis or as specifically programmed or initiated by a user or by the system. FIG. 25 illustrates an example of certain of these processes carried out by the model development module. As shown in FIG. 25, based upon data mined and analyzed (i.e. acquired or extracted from the resources), the module will typically identify relationships between available data as indicated at block 382 of FIG. 25. The relationships may be based upon known interactions between the data, or based upon identification algorithms as noted above (e.g. regression analysis, decision trees, clustering algorithms, neural networks, expert input, etc.). Moreover, it should be noted that the relationship identification may be based on any available data. That is, the data may be most usefully employed in the system when considered separate from its type, modality, practice area, and so forth. By way of example, clinical data may be employed from imaging systems and used in conjunction with demographic information and with histological information on a particular patient. The data may also incorporate non-patient specific (e.g. general population) data which may be further indicative of risk or likelihood of a particular disease state, and so forth. Based upon the identified relationships, rule identification is carried out as indicated at block 384. Such rules may include comparisons, Boolean relationships, regression equations, and so forth used to link the various items of data or input in the identified relationships.

Input refinement steps are carried out as indicated at block 386 in which the relationships are linked to various data inputs which are available from the resources or database or knowledge base. As noted in FIG. 25, such inputs 388 may be non-parametric, that is, relate to raw or processed data which is not specifically influenced by settings or parameters of the CAX process. Other input identification, as indicated at block 390, is targeted to parametric inputs which can be impacted by alteration of the CAX process. Based upon the input identification, the rule identification and the relationship identification, reconciliation and refinement of the model is possible as indicated at block 392. Again, such reconciliation and refinement may include addition or deletion of certain inputs, placement of certain conditions on inclusion of inputs, weighting of some inputs, and so forth. Such reconciliation and refinement may be carried out by the system or with input from an expert as indicated at reference numeral 6 in FIG. 25. The entire process, then, may be somewhat iterative as indicated by the return arrows in FIG. 25, such that the reconciliation and refinement process may further impact identification of relationships, rules and inputs.

A wide range of models may be developed by the foregoing techniques. In a clinical context for example, different types of data as described above maybe accessible to the CAX algorithms, such as image data, demographic data, and non-patient specific data. By way of example, a model may be developed for diagnosing breast cancer in women residing in a specific region of a country during a specific period of years known to indicate an elevated risk of such conditions. Additional factors that may be considered where available, could be patient history as extracted from questionnaires completed by the patient (e.g. smoking habits, dietary habits, etc.).

As a further example, and illustrating the interaction between the various processes, a model for acquiring data or processing data may be influenced by a computer-assisted diagnosis (CADx) algorithm. In one example, for example, the output from a therapy algorithm with highlighting of abdominal images derived from scanned data may be altered based upon a computer-assisted diagnosis. Therefore, the image data may be acquired or processed in relatively thin slices for a lower abdomen region where the therapy algorithm called for an appendectomy. The rest of the data may be processed in a normal way with thicker slices. Thus, not only can the CAX algorithms of different focus influence one another in development and refinement of the predictive models, but data of different types and from different modalities can be used to improve the models for identification and treatment of diseases, as well as for non-clinical purposes.

Algorithm and Professional Training

Figure 26:
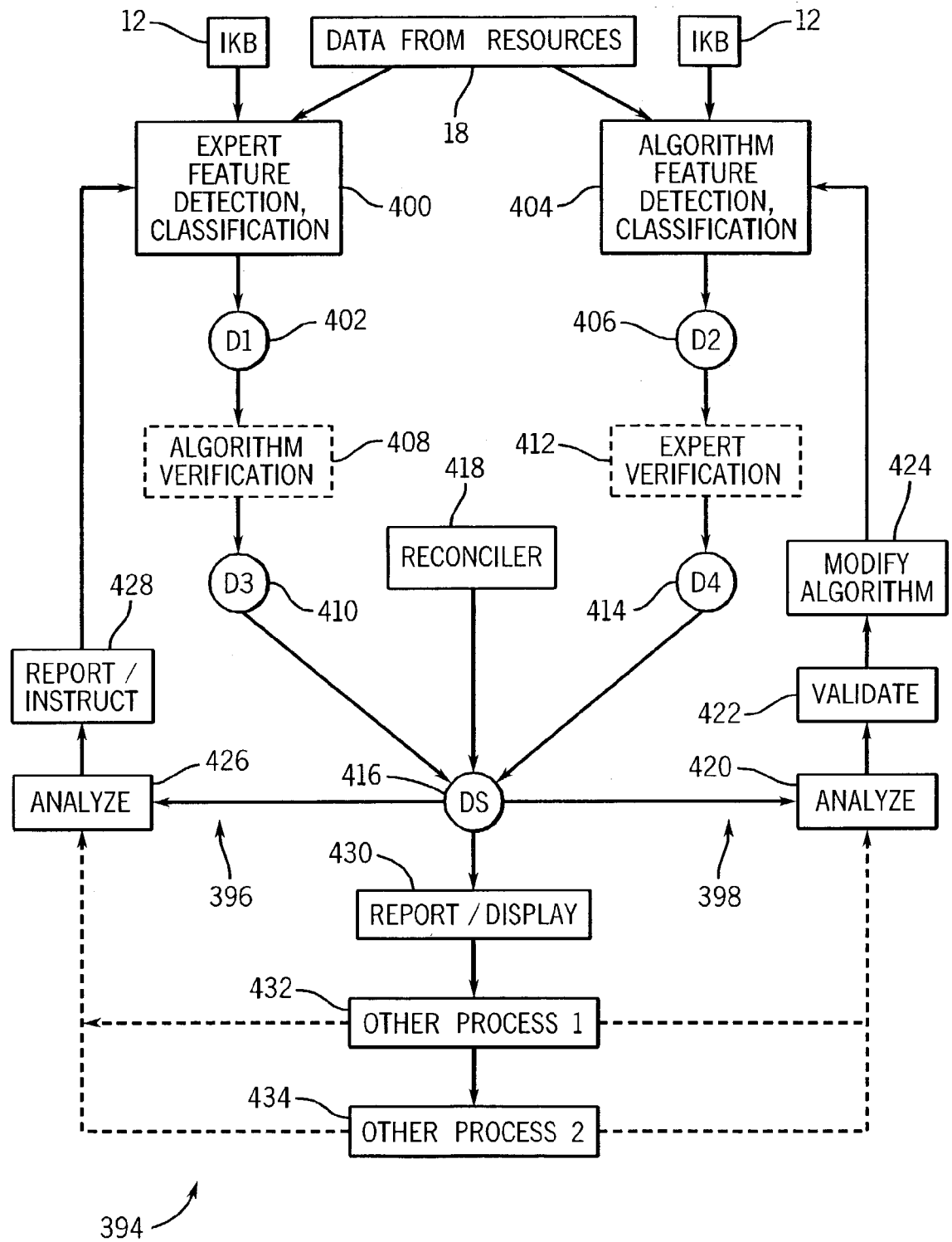
FIG. 26 is a flowchart illustrating a technique for refining or training a computer-assisted algorithm and a medical professional.

As noted above, a number of computer-assisted algorithms may be implemented in the present technique. Such algorithms, generally referred to herein as CAX algorithms, may include processing and analysis of a number of types of data, such as medical diagnostic image data. The present techniques offer enhanced utility in refining such processes as described above, and for refining the processes through a learning or training process to enhance detection, segmentation, classification and other functions carried out by such processes. The present techniques also offer the potential for providing feedback, such as for training purposes, of medical professionals at various levels, including radiologists, physicians, technicians, clinicians, nurses, and so forth. FIG. 26 illustrates exemplary steps in such a training process both for an algorithm and for a medical professional.

Referring to FIG. 26, an algorithm and professional training process 394 is illustrated diagrammatically. The process may include separate, although interdependent modes, such as a professional training mode 396 and an algorithm training mode 398. In general, both modes may be programmed and functioned in one or more operating environments, with the actual functionality performed varying depending upon how the user is currently implementing the process.

In general, the process provides for interaction between computer-assisted algorithms, such as a CAD algorithm, and functions performed by a medical professional. The process will be explained herein in context of a CAD program used to detect and classify features in medical diagnostic image data. However, it should be borne in mind that similar processes can be implemented for other CAX algorithms, and on different types of medical diagnostic data, including data from different modalities and resource types.

The process 394 may be considered to begin at a step 400 where an expert or medical professional performs feature detection and classification. As will be recognized by those skilled in the art, such functions are typically performed as part of a diagnostic image reading process, beginning typically with a reconstructed image or a set of images in an examination sequence. The expert will typically draw the data from the integrated knowledge base 12 or from the various resources 18 and may draw upon additional data from such resources to support the "reading" process of feature detection and classification. The expert then produces a dataset labeled D1, and referred to in FIG. 26 by reference numeral 402, which may be an annotated medical diagnostic image in a particular application. Any suitable technique can be used for producing the dataset, such as conventional annotation, dictation, interactive marking, and similar techniques.

In parallel with the expert feature detection and classification functions, an algorithm, in the example a CAD algorithm, performs similar feature detection and classification functions at step 404. As noted above, various programs are available for such functions, typically drawing upon raw or processed image data, and identifying segmenting and classifying identified features in accordance with parametric settings. Such settings may include mathematically or logically-defined feature recognition steps, intensity or color-based feature detection, automated or semi-automated feature segmentation, and classification based upon comparisons of identified and segmented features with known characteristics of identified pathologies. As a result of step 404, a second dataset D2, referred to in FIG. 26 by reference numeral 406, is produced, which may be similarly annotated for display.

The expert-produced dataset 402 is subjected to verification by the same or a different computer algorithm at step 408. The algorithm verification step 408 is illustrated in broken lines in FIG. 26 due to the optional nature of this step when the system is operating in algorithm training mode. That is, the algorithm verification of the expert reading is preferred where feedback is provided to the expert as described below. Alternatively, the algorithm verification step may be implemented in all cases, such that a subsequently processed dataset includes both the reading by the expert and by the algorithm and the filtering of the expert-identified and classified features as produced by the algorithm verification step. In general, the algorithm verification step will serve to eliminate false positive readings as produced by the expert. It should also be noted that a particular algorithm and/or the parametric settings employed by the algorithm at step 408 may be different from those used in step 404. That is, the algorithm verification step may be performed by a different algorithm, or with different parametric settings, so as to provide a more or less stringent filter at step 408 than was applied for the algorithm feature detection and classification at step 404. Step 408 results in a further refined dataset D3, referred to in FIG. 26 by reference numeral 410, which may constitute a reconstructed image, annotated to indicate, where desired, both the expert feature detection and classification results, and changes in such results as result of the algorithm verification.

Similarly, the dataset 406 resulting from the algorithm feature detection and classification is subjected to expert verification at step 412. As with step 408, step 412 may be an optional step, particularly where the system functions in professional training mode. That is, where feedback is intended to be provided to the medical professional or expert, the step may be eliminated so as to provide comparison of the algorithm feature detection and classification with that produced by the medical professional. It should also be noted that a particular expert and/or the decision thresholds employed by the expert at step 412 may be different from those used in step 400. The resulting dataset D4, referred to in FIG. 26 by reference numeral 414, again, may be reconstructed, when the data represents images, and may be annotated to indicate features identified by the algorithm and the changes made to such identification or classification by the expert or medical professional.

In a present implementation, the datasets 410 and 414 are joined in a union dataset 416, which may again comprise of one or more images displaying the origin of particular features detected and classified, along with changes made by either the algorithm or the expert during verification. Block 418 in FIG. 26 represents a reconciler which may be a medical professional (the same or a different medical professional than carrying out the feature detection and classification or verification), or the reconciler may include automated or semi-automated processing. The purpose of the reconciler 418 is to resolve conflicts between detection and classification by the algorithm and the expert, along with such conflicts that may result from modifications following the verification at steps 408 and 412.

Once the reconciler has acted upon the dataset DS, referred to in FIG. 26 by reference numeral 416, in an algorithm training mode 398, changes made by the expert verification at step 412 and by the reconciler 418 are analyzed as indicated at step 420. The analysis may consist of comparing the changes made and determining why the changes were necessitated. As will be appreciated by those skilled in the art, CAX processing typically includes various settings which can be altered to change the feature identification, detection, segmentation, and classification that may have been performed. The analysis performed at step 420, then, can be directed to identifying how such parametric inputs can be modified to permit the results of the verification and reconciliation to conform. It should be noted, however, the analysis performed at step 420 may not necessarily imply that a change in the algorithm is needed to desired. That is, in certain situations it may be desirable that the algorithm not produce exactly the same results as the expert, in order to enhance the "second reader" or "independent first reader" nature of the algorithm functions. At step 422, then, validation of any possible changes to the algorithm are made, such as by an expert or a team of experts. Where the validation step results in a conclusion that a change in the algorithm may be in order, such modification may be implemented as indicated at step 424. While reference is made in the present process to parametric modification of such algorithms, it should also be noted that such modifications may include identification and consideration of other inputs, such as inputs available from the integrated knowledge base 12, as discussed above with reference to FIG. 24.

When operating in a professional training mode 396, similar analysis of the dataset 416 can be made as indicated at step 426 in FIG. 26. Such analysis, again, may be intended to determine why changes in the expert reading were made by the algorithm in the verification 408, and how such performance can be brought into conformity. Based upon such analysis, at step 428 the results may be reported and instruction provided for the medical professional. It should be noted that such reporting and instruction may simply provide feedback for the medical professional, such as to indicate changes that would have been made to the dataset 402 by algorithm verification. However, the reports or instruction may also provide useful didactic input, references to teaching materials, samples, image-based data retrieval, and so forth, such that the medical professional is apprised of relevant considerations for improvement of performance.

Following creation of the dataset 416, results may be reported and displayed in a conventional manner as indicated at step 430. Moreover, and optionally, other processes may be performed on the resulting data which may similarly provide assistance in refining either the CAX algorithm or teaching the medical professional. Such processes are illustrated in FIG. 26 at reference numerals 432 and 434.

It should be noted that the foregoing processes can be implemented as normal operating procedures, where desired. That is, complimentary algorithm and expert reading procedures, with complimentary algorithm and expert verification procedures, and with the use of a reconciler, may be employed for regular handling of data for diagnostic and other purposes. In a professional training mode, however, a relatively "heavy" filter may be used at the algorithm verification step, such as to identify more positive reads as potential false positive reads for training purposes. A different or "lighter" filter may be used during normal operation and for the algorithm feature detection classification formed at step 404. In addition, the analysis performed either at step 420 or at 426 may further rely upon the integrated knowledge base to identify trends, prognoses, and so forth based upon both patient-specific data, non-patient specific data, temporal data of both a patient-specific and non-patient specific nature, and so forth. It should also be noted that, as discussed above, various changes can be made to the CAX algorithms as a result of the training operations. Such changes may include changes in processing, and may be "patient-specific", with such changes being stored for future analysis of data relating to the same patient. That is, for example, for image data relating to a patient with certain anatomical characteristics (e.g. weight, bone mass, size, implants, prosthesis, etc.), the algorithm may be specifically tailored for the patient by altering parametric settings to enhance the utility of future application of the algorithm and future correction or suggestions made to expert readings based upon the determinations made by the algorithm. In addition, changes can also be made to the integrated knowledge base itself based upon the learning mode outcome, such as to adjust "normal ranges" within the data stored in the knowledge base.

In Vitro Characteristic Identification

As noted above, among the many resources and types of resources available for the present technique, certain resources will produce data or samples which may be subject to in vitro data acquisition and analysis. The present techniques offer a particularly useful tool in the processing of such data and samples for several reasons. First, the samples may be analyzed based upon input of data of multiple types of resources. Various computer-assisted processes, including data acquisition, content-based information retrieval, processing and analyzing of retrieved and/or acquired data, identification of characteristics, and classification of data based upon identified characteristics may be implemented. Moreover, temporal analysis may be performed to analyze characteristics of in vitro samples as they relate to previously-identified characteristics using known data, such as from the integrated knowledge base. The information retrieval processes may furthermore be based upon specific attributes of the in vitro sample, such as spatial attributes (e.g. size of specific components or characteristics), temporal attributes (e.g. change in features over time), or spectral attributes (e.g. energy level, intensity, color, etc.). Such content, also identified, where possible, from information stored in the integrated knowledge base, may include biomarkers, images, relationship tables, standardized matrixes, and so forth. Thus, multiple attributes may be used to enhance the acquisition, processing and analysis of in vitro samples through reference to available data, particularly information in the integrated knowledge base.

Figure 27:
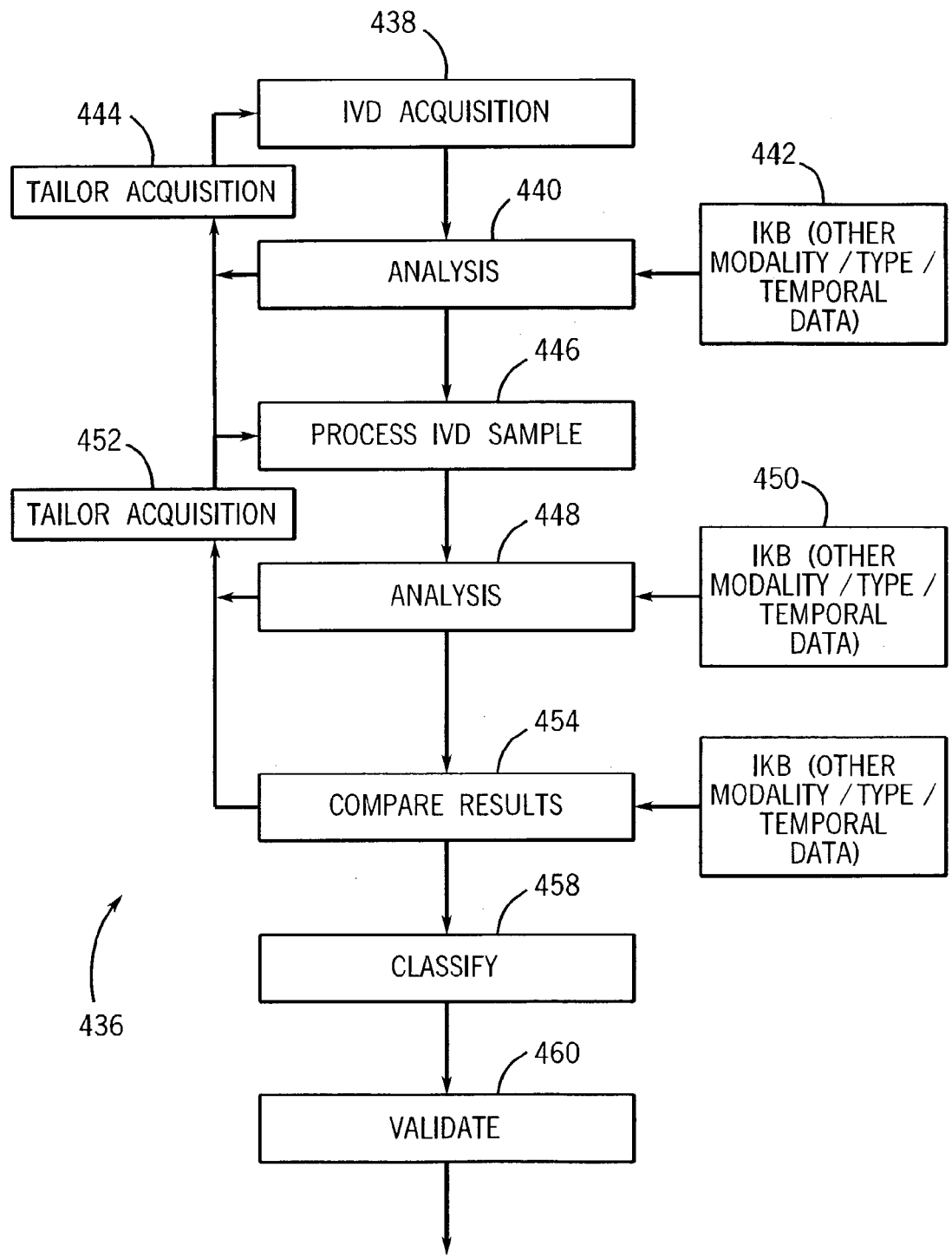
FIG. 27 is a flowchart illustrating processing steps for in vitro sample processing and analysis.

FIG. 27 generally represents steps in processing of an in vitro sample in accordance with such improved techniques. The in vitro characteristic identification process, generally represented by reference numeral 436 in FIG. 27, begins at step 438 where the in vitro diagnostics sample is acquired. As noted above, any suitable technique can be used for acquiring the sample, which may typically include body fluids, tissues, and so forth. At step 440 an analysis is performed on the acquired sample. The analysis is informed by input from the integrated knowledge base as indicated at block 442. The input may include data relating to other modalities, resource types, or temporal data relating to similar samples from the patient. The analysis performed at step 440 may include certain comparisons with such data and may be somewhat preliminary in nature. Thus, without departing from the acquisition step in the overall process, the sample acquisition may be tailored to the needs of the process as indicated at step 444. Such tailoring may include acquisition of other samples, acquisitions of samples under specific conditions (e.g. later in time during an office visit, during patient activity or rest periods, from other regions of the body, and so forth). Thus, the in vitro diagnostics sample acquisition process may be improved by computer analysis that influences the acquisition of the sample itself.

Following acquisition of the sample, processing of the sample may be performed at step 446. The processing performed at step 446, rather than data processing, is typically sample processing to condition the sample for extraction of data either manually or in a semi-automated or fully-automated process. Following the processing at step 446, results of the processing are analyzed at step 448. As before, the analysis performed at step 448 may include consideration of data from the integrated knowledge base, including data from other modalities, resource types, and times. As with the analysis performed at step 440, the analysis at step 448 may be preliminary in nature, or further analysis may be performed by tailoring the processing as indicated at step 452. Thus, prior to final analysis of an in vitro diagnostic sample, additional processing may be in order, such as slide preparation, analysis for the presence of various chemicals, tissues, pathogens, and so forth.

At step 454 results of the analysis are compared to known profiles, such as from the integrated knowledge base, to determine possible diagnoses. As before, the comparisons made at step 454 may be based upon data from different modalities, resource types and times. The comparisons may result in classification of certain data indicative of disease states, medical events, and so forth as indicated at step 458. The comparison and classification may further indicate that a specific patient (or a population of patients) is undergoing certain trends that may be indicative of potential diagnoses, prognoses, and so forth. The results of the classification made at step 458 may be validated, such as by a medical professional, at step 460.

In general, for the present purposes, quantifiable signs, symptoms and/or analytes (e.g. chemicals, tissues, etc.) in biological specimens characteristic of a particular disease or predisposition for a disease state or condition may be referred to as "biomarkers" for the disease or condition. While reference has been made hereinto analysis and comparison in general, such biomarkers may include a wide range of features, including the spatial, temporal and spectral attributes mentioned above, but also including genetic markers (e.g. the presence or absence of specific genes), and so forth.

By way of example, in a typical application, a patient's tissue will be sampled and transmitted to a laboratory for analysis. The laboratory acquires the data with computer assistance using appropriate detectors, such as microscopes, fluorescent probes, micro arrays, and so forth. The data contents, such as biomarkers, image signals, and so forth are processed and analyzed. As noted above, the acquisition and processing steps themselves may influenced by the reference to other data, such as from the integrated knowledge base. Therefore, such data is retrieved from the knowledge base for assisting in the acquisition, analysis, comparison and classification steps.

The comparisons made in the process may be parametric in nature or nonparametric. That is, as noted above, parametric comparisons may be based upon measured quantities and parameters where characteristics are indexed or referenced in parameter space and comparisons are performed in terms of relative similarity of one dataset to another with respect to certain indices, such as a Euclidean distance measure between two feature set vectors. Such indices may include, in the example of microscopy, characteristic cell structures, colors, reagent, indices, and so forth. Other examples may include genetic composition, presence or absence of specific genes or gene sequences, and so forth.

Non-parametric comparisons include comparisons made without specific references to indices, such as for a particular patient over a period of time. Such comparisons may be based upon the data contents of one dataset that is compared for similarity to characteristics from the data contents of another dataset. As will be noted by those skilled in the art, one or both of such comparisons may be performed, and in certain situations one of the comparisons may be preferred over the other. The parametric approach is typically used when a comparison is to be made between a given specimen and a different specimen with known characteristics, such as based upon information from the integrated knowledge base. For example, in addition to deriving textures and shape patterns of cells in a histopathology image, parameters may also be derived from demographic data, electrical diagnostic data, imaging diagnostic data, and concentrations of biomarkers in biological fluid or a combination of these. Thus, the comparisons can be made based upon data from different modalities and different resource types, as noted above. Non-parametric comparisons may generally be made, again, for temporal comparison purposes. By way of example, a specimen may exhibit specific ion concentrations dynamically changing and temporal variations of data attributes (e.g. values, ratios of values, etc.) may need to be analyzed to arrive at a final clinical decision.

Computer-Assisted Data Operating Algorithms

As noted above, the present technique provides for a high level of integration of operations in computer-assisted data operating algorithms. As also noted above, certain such algorithms have been developed and are in relatively limited use in various fields, such as for computer-assisted detection or diagnosis of disease, computer-assisted processing or acquisition of data, and so forth. In the present technique, however, an advanced level of integration and interoperability is afforded by interactions between algorithms both in their development, as discussed above with regards to model development, and in their use. Moreover, such algorithms may be envisaged for both clinical and non-clinical applications. Clinical applications include a range of data analysis, processing, acquisition, and other techniques as discussed in further detail below, while non-clinical applications may include various types of resource management, financial analysis, insurance claim processing, and so forth.

Figure 28:
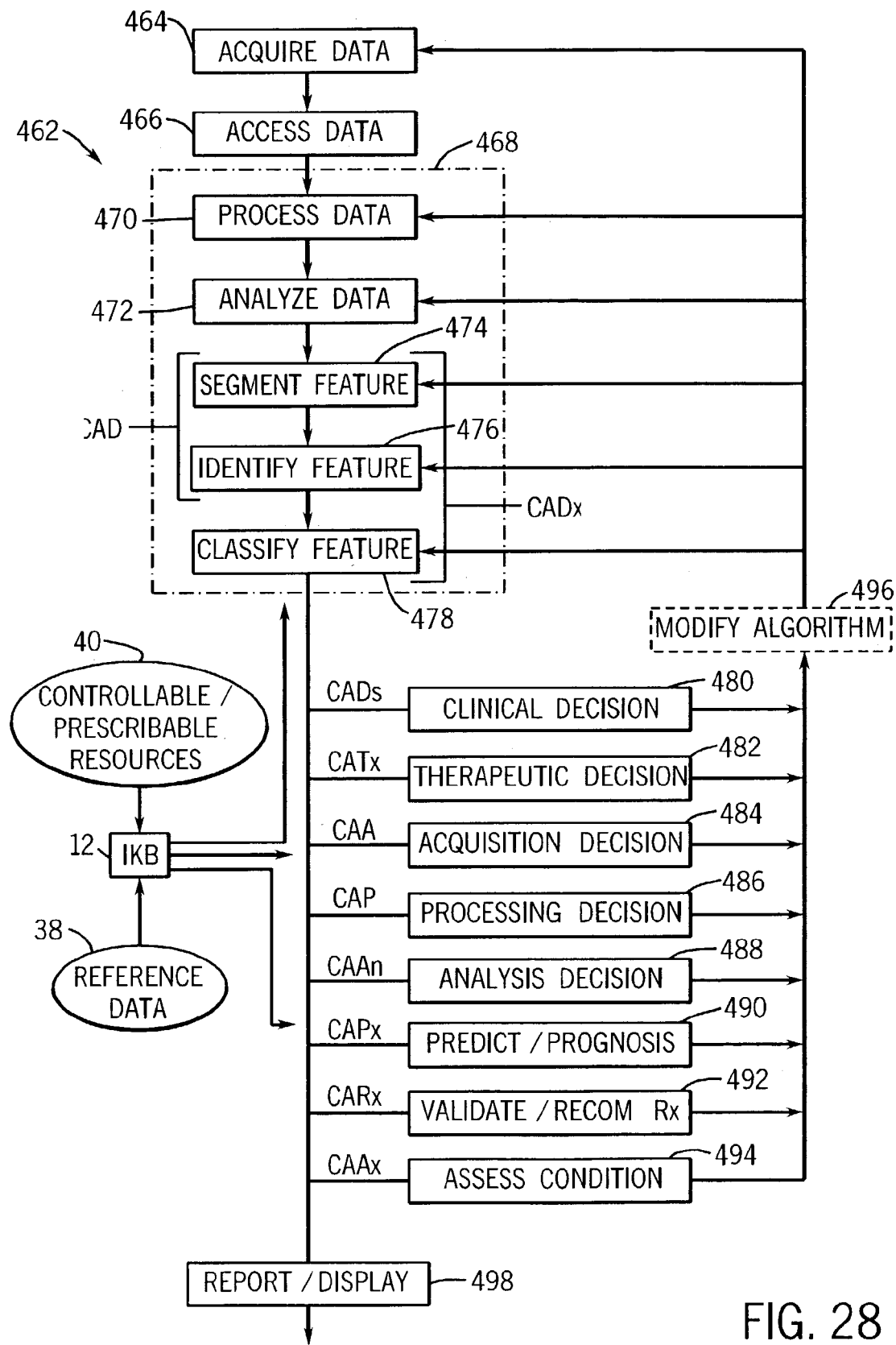
FIG. 28 is a diagrammatical representation of a CAX system including one or more CAX algorithms in accordance with aspects of the present technique.

FIG. 28 provides an overview of interoperability between such algorithms, referred to generally in a present context as computer-assisted data operating algorithms or CAX. As noted above, CAX algorithms in the present context may be built upon algorithms presently in use, or may be modified or entirely constructed on the basis of the additional data resources, integration of such data resources, or interoperability between such resources in the algorithms and between the algorithms themselves as discussed throughout the present description. In the overview of FIG. 28, for example, an overall CAX system 462 is illustrated as including a wide range of steps, processes or modules which may be included in a fully integrated system. As noted above, more limited implementations may also be envisaged in which some or a few only of such processes, functions or modules are present. Moreover, in a presently contemplated embodiment, such CAX systems are implemented in the context of integrated knowledge basis such that information can be gleaned to permit adaptation and optimization of both the algorithms themselves and the data managed in the algorithms. Such development and optimization may be carried out, as noted above, through the model development modules described herein, and various aspects of the individual CAX algorithms may be altered, including rules or processes implemented in the algorithms, as well as various settings. More will be said about such aspects of the CAX algorithms below with regards to FIG. 29.

As summarized in FIG. 28, in general, the CAX algorithms begin at a step 464 in which data is acquired. As noted throughout the present discussion, the acquisition of data may take many forms, particularly depending upon the resource type and the resource modality providing the data. Thus, data may be input manually, such as from forms or conventional terminals, or data may be acquired through laboratory reporting techniques, imaging systems, automatic or manual physiological parameter acquisition systems, and so forth. The data is typically stored in one or more memory devices as discussed above, some of which may be incorporated in the data acquisition systems themselves, such as in imaging systems, picture archiving systems, and so forth.

At step 466 data of interest or utility for the functions carried out by the CAX algorithm is accessed. A series of operations may then be performed on the accessed data as indicated generally at reference numeral 468. Throughout such processing, and indeed at step 466, the integrated knowledge base 12, in full or in part, may be accessed to extract data, validate data, synchronize data, download data or upload data during the functioning of the CAX algorithm.

While many such computer-assisted data operating algorithms may be envisaged, at present, some ten such algorithms are anticipated for carrying out specific functions, again both clinical and non-clinical. Summarized in FIG. 28, therefore, are steps in algorithms for computer-assisted detection of features (CAD), and algorithms for computer aided diagnosis of medical conditions (CADx). Further, computer-assisted clinical decision algorithms (CADs) are implemented in which clinical decisions are automatically made based upon analysis and processing. Similarly, therapeutic or treatment decisions may be implemented through additional routines (CATx). Specific computer-assisted acquisition (CAA) and computer-assisted processing (CAP) algorithms may be implemented of type described in detail above. Further, computer-assisted analysis (CAAn) algorithms may be implemented as discussed below. Computer-assisted prediction or prognosis (CAPx) algorithms are also envisaged in a medical context, as are prescription validation, recommendation or processing algorithms (CARx). Finally, computer-assisted assessment (CAAx) algorithms are envisaged for a range of conditions, both clinical and non-clinical.

Considering in further detail the data operating steps summarized in FIG. 28, at step 470 accessed data is generally processed, such as for digital filtering, conditioning of data, adaptation of dynamic ranges, association of data, and so forth. As will be appreciated both those skilled in the art, the particular processing carried out in step 470 will depend upon the type of data being analyzed in the type of analysis or functions being performed. It should be noted, however, that data may be processed from any of the resources discussed above, and indeed data from more than one modality or even type of resource may be processed, such as for complex analysis of the presence risk, or treatment of medical conditions, and so forth. At step 472, similarly, analysis of the data is performed. Again, such analysis will depend upon the nature of the data and the nature of the algorithm on which the analysis is performed.

Following such processing and analysis, at step 474 features of interest are segmented or circumscribed in a general manner. Again, in image data such feature segmentation may identify the limits of anatomies or pathologies, and so forth. More generally, however, the segmentation carried out at step 474 is intended to simply discern the limits of any type of feature, including various relationships between data, extents of correlations, and so forth. Following such segmentation, features may be identified in the data as summarized at step 476. While such feature identification may be accomplished on imaging data to identify specific anatomies or pathologies, it should be borne in mind that the feature identification carried out at step 476 may be much broader in nature. That is, due to the wide range of data which may be integrated into the inventive system, the feature identification may include associations of data, such as clinical data from all types of modalities, non-clinical data, demographic data, and so forth. In general, the feature identification may include any sort of recognition of correlations between the data that may be of interest for the processes carried out by the CAX algorithm. At step 478 such features are classified. Such classification will typically include comparison of profiles in the segmented feature with known profiles for known conditions. The classification may generally result from parameter settings, values, and so forth which match such profiles in a known population of datasets with a dataset under consideration. However, the classification may also be based upon nonparametric profile matching, such as through trend analysis for a particular patient or population of patients over time.

Based upon the processing carried out by the algorithm, a wide range of decisions may be made. As summarized in step 462, such decisions may include clinical decisions 480, therapeutic decisions 482, data acquisition decisions 484, data processing decisions 486, data analysis decisions 488, condition prediction or prognosis decisions 490, prescription recommendation or validation decisions 492, and assessment of conditions 494. As noted above, the high level of integration of the processing operations provided by the present technique, and the integration of data from a range of resources, permits any one of the categories of functions carried out by the CAX algorithm to be modified or optimized, both for non-patient specific reasons and for patient-specific reasons, as summarized in FIG. 28. Thus, as a result of any one of the decisions made in the algorithm, modifications in the same or different CAX algorithms may be made as summarized at step 496. As also noted below, such modifications may include selection of a different algorithm type, modification, addition or removal of one or more functions carried out by the algorithm, or modification of parameters and settings employed by the algorithm in carrying out the functions. Thus, in the flow diagram of FIG. 28, feedback may be had to any one of the steps summarized above including data acquisition, processing, analysis, feature identification, feature segmentation, feature classification, or any other function carried out within the CAX algorithms. In general, some form of reporting or display of results of the algorithms will be provided as summarized at step 498.

In general, in the present context, each decision submodule has a task (e.g., acquisition) and a purpose (e.g., cancer detection) associated with it. Depending upon the task and the intended purpose, decision rules are established. In one implementation, a domain expert can decide on the rules to be used for a given task and purpose. In another implementation, a library of rules relating to all possible tasks and purposes can be determined by a panel of experts and used by the submodule. In another implementation, the library of rules can be accessed from the integrated knowledge base. In another implementation, new rules may be stored in integrated knowledge base, but are derived from other means prior to storage in the knowledge base. In a typical implementation, the combination of the current data and the rules are used to develop a summary of hypothesized decision options for the data. These options may lead to several outcomes, some of which may be desired and some undesired. To obtain the optimal outcome, a metric is established to provide scores for each of the outcomes. Resultant outcomes are thus evaluated, and the selected (i.e. optimal) outcome determines the function provided in the decision block.

As mentioned, the various CAX algorithms may be employed individually or with some level of interaction. Moreover, the algorithms may be employed in the present technique without modification, or some or a high level of adaptability may be offered by virtue of integration of additional data resources, and processing in the present system. Such adaptation may be performed in real time or after or prior to data acquisition events. Moreover, as noted above, triggering of execution or adaptation of CAX algorithms may be initiated by any range of initiation factors, such as scheduled timing, operator intervention, change of state of data, and so forth. In general, a number of aspects of the CAX system or specific CAX algorithms may be altered. As summarized in FIG. 29, the present technique envisages at a substantially new and different approach to compiling, analyzing and altering such CAX algorithms for the adaptation and optimization provided.

Figure 29:
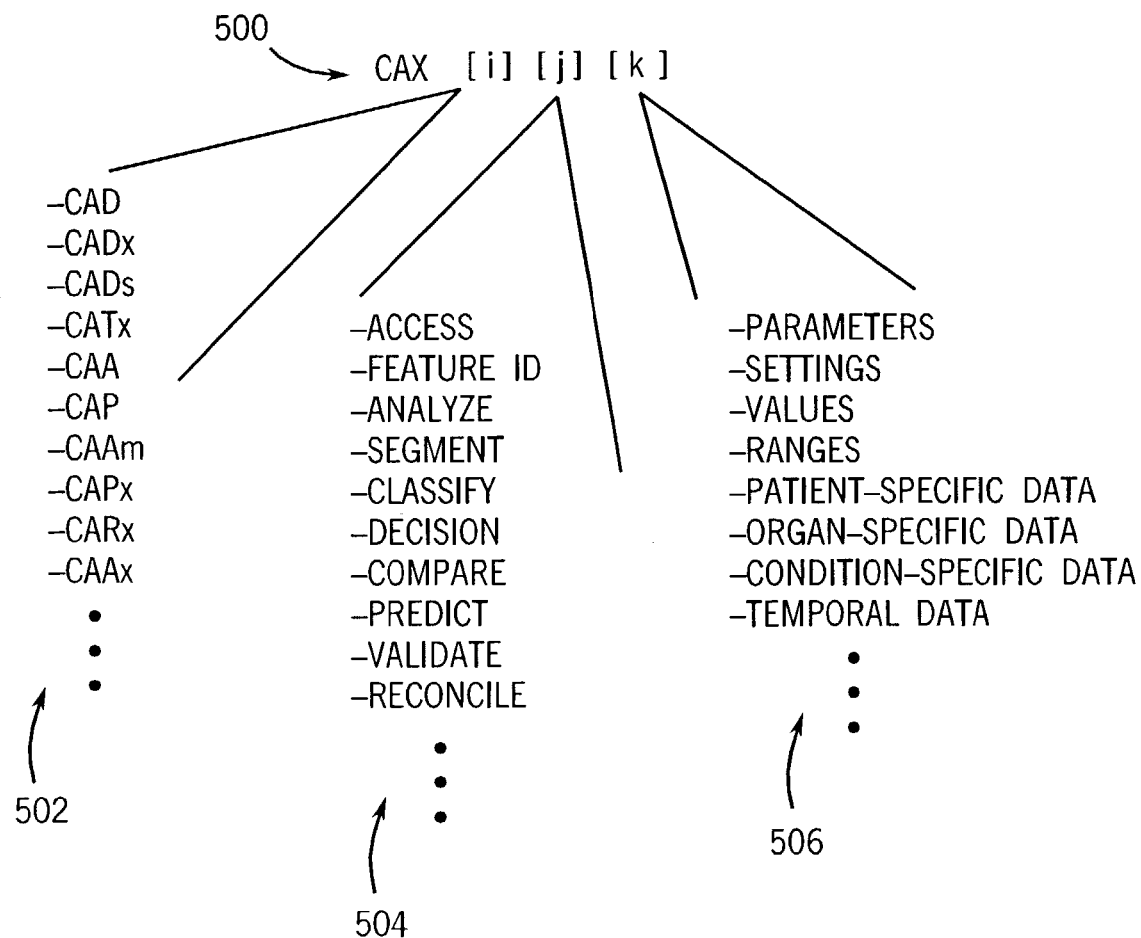
FIG. 29 is a diagrammatical representation of the CAX algorithms of FIG. 28 and functions and operators employed by the algorithms.

Referring to FIG. 29, an overall CAX formulation, designated generally by the reference numeral 500, may be represented by separate functionalities or parameters [i][j][k]. These aspects of the CAX algorithms, in the present formulation, represent first the primary type of function performed by the algorithm, as denoted by the list 502 in FIG. 29, the functions carried out by the algorithm, as denoted by reference numeral 504 in FIG. 29 and the specific data attributes 506 employed in the algorithms. The algorithm designations 502 may follow general lines for functionality in the algorithms, although those skilled in the art will recognize that more than one such functionality may be employed, such as through subroutine, submodules, and the like. The [j] level of functionality in the algorithms may include a wide range of integrated or modular functions that are carried out in the various algorithms, some of which may be shared by a different algorithm. Noted in particular, in FIG. 29 are functions such as data access, feature identification, analysis, segmentation, classification, decision, comparison, prediction, validation, and reconciliation. Other functions may, of course, be employed as well. In general, in the present context such functionalities are implemented as submodules of the algorithms, and may generally be implemented as "tool kits" which are called upon by the algorithm and developed by programming, expert systems, neural networks, and so forth as discussed above.

The [k] level of the CAX algorithm represents generally, variables or inputs that are used by the CAX algorithms for performing the functions specified at the [j] level. By way of example, in presently contemplated embodiments, items at the [k] level may include parameters, settings, values, ranges, patient-specific data, organ-specific data, condition-specific data, temporal data, and so forth. Such parameters and settings may be altered in the manner described above, such as for patient-specific implementation of the CAX algorithm or for more broadly-based changes as for a population of patients, institutions, and so forth. It should also be noted, that, as described above with respect to modeling, alterations made in a CAX algorithm may include consideration of data which was not considered prior to a modification. That is, as new data or new relationships are identified, the CAX algorithm may be altered to accommodate consideration of the new data. As will be appreciated by those skilled in the art then, the high degree of integration of the present technique allows for new and useful relationships to be identified among and between data from a wide range of resources and such knowledge incorporated into the CAX algorithm to further enhance its performance. Where available, the data may then be extracted from the integrated knowledge base or a portion of the knowledge base to carry out the function when called upon by the CAX algorithm.

It should be noted that, while a single CAX algorithm may be implemented in accordance with the present technique, a variety of CAX algorithms may be implemented in parallel and in series for addressing a wide range of conditions. As summarized in FIG. 30, for example, a multi-CAX implementation 508 may include a first type of algorithm 510, which may be any of the algorithms summarized above. Moreover, the selected type of algorithm may be implemented in parallel, such that multiple different or complementary functions may be executed. Each such algorithm will typically include fundamental operations such as noted at reference numeral 512. Such operations may generally resemble those of CAD algorithms, including steps such as feature segmentation 514, feature identification 516, and feature classification 518. Based upon such steps, decisions may be made, such as for specific recommendations for future actions, as indicated at step 520. As noted above, based upon such operations, the algorithm may be modified, as noted at step 522. The modification is then implemented by returning to the system or method employed to generate or process the data, as noted at step 524. As noted above, the modifications may be made as various levels in the algorithms, such as levels [j] and [k] discussed above.

Figure 30:
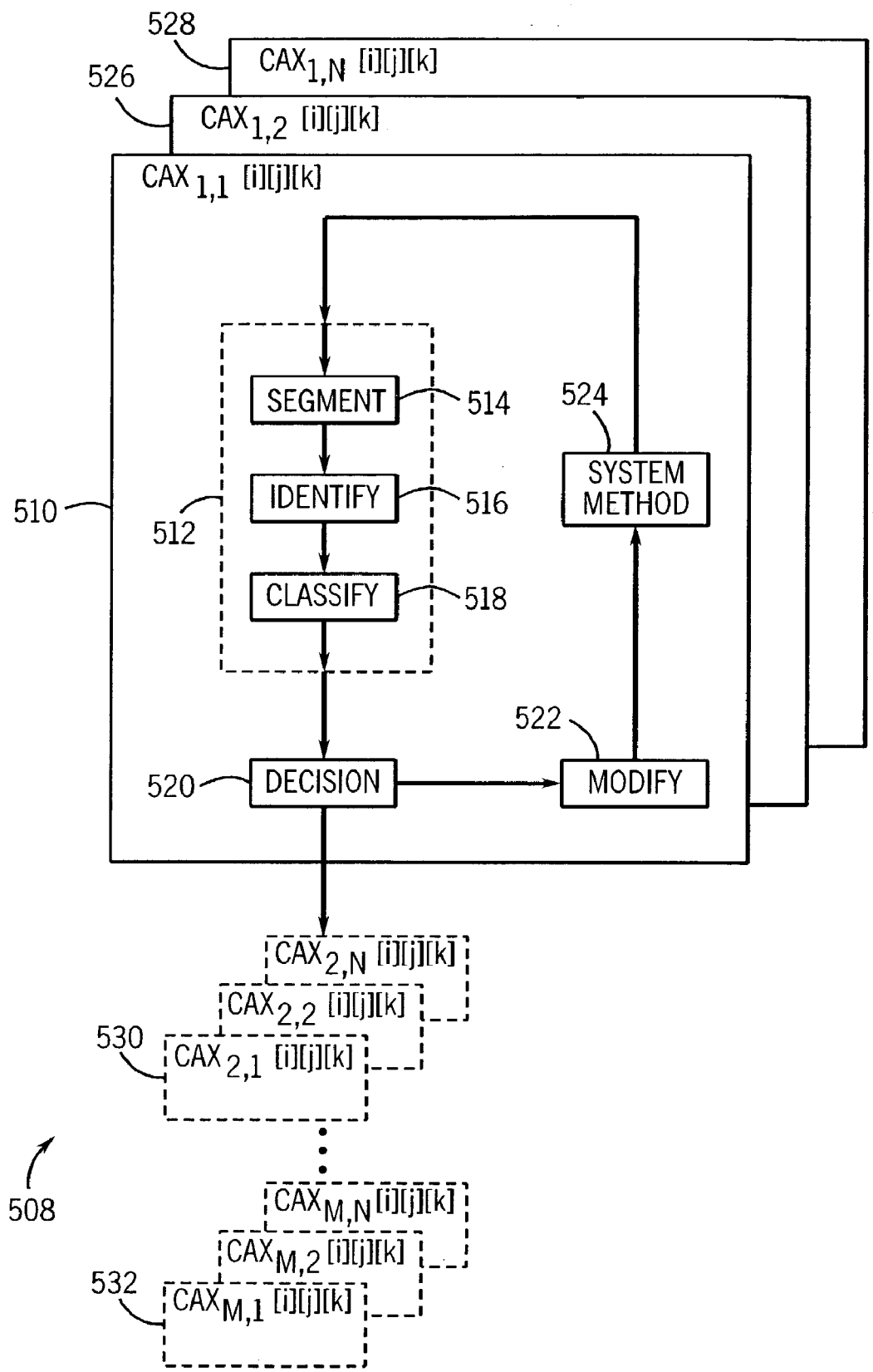
FIG. 30 is a diagrammatical representation of a scheme for implementing CAX algorithms in parallel and/or in series to evaluate a range of conditions and situations.

As also summarized in FIG. 30, a number of CAX algorithms of different type (i.e. CAX[i]) may be executed in parallel, such as to identify features of interest of different type, or from data of different type or modality. Such additional algorithms, designated by reference numerals 526 and 528 may include any of the algorithm types discussed above. Similarly, CAX algorithms of the same or different type may be executed in series, as indicated at reference numerals 530 and 532 in FIG. 30. Such algorithms may, in fact, be selected based upon results of earlier-executed algorithms.

While all of the CAX algorithms discussed above may have application in addressing a range of clinical and non-clinical issues, a more complete discussion of certain of these is useful in understanding the types of data operations performed by the modules or submodules involved.

Computer-Assisted Diagnosis (CADx):

Computer-assisted diagnosis modules aid in identifying and diagnosing specific conditions, typically in the area of medical imaging. However, in accordance with the present technique, such modules may incorporate a much wider range of data, both from imaging types and modalities, as well as from other types and modalities of resources. The following is a general description of an exemplary computer-assisted diagnosis module. As described above and shown in FIG. 28, CADx consists of a computer-assisted detection (CAD) module and a feature classification block.

As described above, the medical practitioner derives information regarding a medical condition from a variety of sources. The present technique provides computer-assisted algorithms and techniques calling upon these sources from multi-modal and multi-dimensional perspectives for the detection and classification of a range of medical conditions in clinically relevant areas including (but not limited to) oncology, radiology, pathology, neurology, cardiology, orthopedics, and surgery. The condition identification can be in the form of screening using the analysis of body fluids and detection alone (e.g., to determine the presence or absence of suspicious candidate lesions) or in the form of diagnosis (e.g., for classification of detected lesions as either benign or malignant nodules). For the purposes of simplicity, one present embodiment will be explained in terms of a CADx module to diagnose benign or malignant lesions.

In the present context, a CADx module may have several parts, such as data sources, optimal feature selection, and classification, training, and display of results. Data sources, as discussed above, may typically include image acquisition system information, diagnostic image data sets, electrical diagnostic data, clinical laboratory diagnostic data from body fluids, histological diagnostic data, and patient demographics/symptoms/history, such as smoking history, sex, age, clinical symptoms.

Feature selection may, itself comprise different types of analysis and processing, such as segmentation and feature extraction. In the data, a region of interest can be defined to calculate features. The region of interest can be defined in several ways, such as by using the entire data "as is," or by using a part of the data, such as a candidate nodule region in the apical lung field. The segmentation of the region of interest can be performed either manually or automatically. The manual segmentation involves displaying the data and delineating the region, such as by a user interfacing with the system in a computer mouse. Automated segmentation algorithms can use prior knowledge, such as the shape and size of a nodule, to automatically delineate the area of interest. A semi-automated method which is the combination of the above two methods may also be used.

The feature extraction process involves performing computations on the data sources. For example, in image-based data and for a region of interest, statistics such as shape, size, density, curvature can be computed. On acquisition-based and patient-based data, the data themselves may serve as the features. Once the features are computed, a pre-trained classification algorithm can be used to classify the regions of interest as benign or malignant nodules. Bayesian classifiers, neural networks, rule-based methods, fuzzy logic or other suitable techniques can be used for classification. It should be noted here that CADx operations may be performed once by incorporating features from all data, or can be performed in parallel. The parallel operation would involve performing CADx operations individually on sets of data and combining the results of some or all CADx operations (e.g., via AND, OR operations or a combination of both). In addition, CADx operations to detect multiple disease states or medical conditions or events can be performed in series or parallel.

Prior to classification, such as, of nodules, in the example, using a CAD module, prior knowledge from training of the module may be performed. The training phase may involve the computation of several candidate features on known samples of benign and malignant nodules. A feature selection algorithm is then employed to sort through the candidate features and select only the useful ones, removing those that provide no information or redundant information. This decision is based on classification results with different combinations of candidate features. The feature selection algorithm is also used to reduce the dimensionality from a practical standpoint. Thus, in the example of breast mass analysis, a feature set is derived that can optimally discriminate benign nodules from malignant nodules. This optimal feature set is extracted on the regions of interest in the CAD module. Optimal feature selection can be performed using a well-known distance measure techniques including divergence measure, Bhattacharya distance, Mahalanobis distance, and so forth.

The proposed method enables, for example, the use of multiple biomarkers for review by human or machine observers. CAD techniques may operate on some or all of the data, and display the results on each kind or set of data, or synthesize the results for display. This provides the benefit of improving CAD performance by simplifying the segmentation process, while not increasing the quantity or type of data to be reviewed.

Again following the lesion analysis example, following identification and classification of a suspicious candidate lesion, its location and characteristics may be displayed to the reviewer of the data. In certain CADx applications this is done through the superposition of a marker (for example an arrow or circle) near or around the suspicious lesion. In other cases CAD and CADx afford the ability to display computer detected and diagnosed markers on any of multiple data sets, respectively. In this way, the reviewer may view a single data set upon which results from an array of CADx operations can be superimposed (defined by a unique segmentation (i.e. regions of interest), feature extraction, and classification procedures).

Computer-Assisted Acquisition (CAA)

Computer-assisted acquisition processing modules may be implemented to acquire further data, again from one or more types of resources and one or more modalities within each type, to assist in enhanced understanding and diagnosis of patient conditions. The acquisition of data may entail one or more patient visits, or sessions (including, for example, remote sessions with the patient), in which additional data is acquired based upon determinations made automatically by the data processing system 10. The information is preferably based upon data available in the integrated database 12, to provide heretofore unavailable levels of integration and acquisition of subsequent for additional data for use in diagnosis and analysis.

In accordance with one aspect of the present technique, for example, initial CAD processing may be used to guide additional data acquisition with or without additional human operator assistance. CT lung screening will serve as an example of this interaction. Assuming first that original CT data is acquired with a 5 mm slice thickness. This is a common practice for many clinical sites to achieve a proper balance between diagnostic accuracy, patient dose, and number of images to review. Once the CAD algorithm identifies a suspicious site, the computer may automatically direct the CT scanner (or recommend to the CT operator) to re-acquire a set of thin slices at the suspected location (e.g., 1 mm slice thickness). In addition, an increased X-ray flux can be used for better signal-to-noise. Because the location is well-defined, the additional dose to the patient is kept to a minimum. The thin slice image provides better spatial resolution and, therefore, improved diagnostic accuracy. Advantages of such interactions include improved image quality and the avoidance of patient rescheduling. It should be noted that most of the diagnostic process generally occurs long after the patient has left the CT scanner room. In conventional approaches, if the radiologist needs thinner slices, the patient has to be called back and re-scanned. Because scan landmarking is performed with a scout image, the subsequent localization of the feature of interest is often quite poor. As a result, a larger volume of the patient organ has to be re-scanned. This leads not only to lost time, but also an increased dose to the patient.

Although this example is for a single modality, the methodology can be applied across modalities, and even across types of resources as discussed above, and over time. For example, the initial CAD information generated with images acquired via a first modality may be used by the CAA algorithm to guide additional data acquisition via a modality B. A specific example of such interaction is the CAD detection of a suspicious nodule in chest x-ray guiding the acquisition of a thin slice helical chest CT exam.

Computer-Assisted Processing (CAP)

Computer-assisted processing modules permit enhanced analysis of data which is already available through one or more acquisition sessions. The processing may be based, again, one or more types of resources, and on one or more modalities within each type. As also noted above, while computer-assisted processing modules have been applied in the past to single modalities, typically in the medical imaging context, the present technique contemplates the use of such modules in a much broader context by use of the various resources available and the integrated knowledge base.

As an example, CAD generated information may be used to further optimize the process of obtaining new images. Following data acquisition and initial image formation (or based upon un-processed or partially processed data without image reconstruction), CAD modules may be used to perform the initial feature detection. Once potential pathology sites are identified and characterized, a new set of images may be generated by a CAA module based upon the findings. The new set of images may be generated to assist the human observer's detection/classification task, or to improve the performance of other CAX algorithms.

For illustration, a CT lung-screening example is considered, although the approach may be, of course, generalized to other imaging modalities, other resource types, and other pathologies. We assume initially that an image is reconstructed with a "Bone" (high-resolution) filter kernel and with a 40 cm reconstruction field of view (FOV). Once a suspicious lung nodule is identified, a CAP module may reconstruct a new set of images at the suspected location with the original scan data. For example, a first images with a "Standard" (lower resolution kernel) filter kernel may first be reconstructed. Although the Standard kernel produces poor spatial resolution, it has the property of maintaining accurate CT numbers. Combining such images with those produced via the Bone algorithm, a CAP algorithm can separate calcified nodules from the non-calcified nodules based on their CT number. Additionally, the CAP module may perform targeted reconstruction at the suspected locations to provide improved spatial resolution, or to improve algorithm performance and/or to facilitate human observer analysis. By way of further example, for a present CT scanner, typical image size is 512×512 pixels. For a 40 cm reconstruction FOV, each pixel is roughly 0.8 mm along a side. From a Nyquist sampling point of view, this insufficient to support high spatial resolutions. When the CAP module re-generates the image, however, with a 10 cm FOV at a suspicious site, each pixel is roughly 0.2 mm along a side and, therefore, can support much higher spatial resolution. Because the additional reconstruction and processing is performed only at the isolated sites, instead of the entire volume, the amount of image processing, reconstruction, and storage becomes quite manageable. It should be noted that a simple example is presented here for the purpose of illustration. Other processing steps (such as image enhancement, local 3D modeling, image reformation, etc.) could also be performed with under the guidance of the CAP module, such as based on the initial CAD result and the results of further processing. The additional images can be used either to refine the original findings of CAD processing, as input to further CAX analyses, or may be presented to the radiologists.

Computer-Assisted Prognosis (CAPx)

Medical prognosis is an estimate of cure, complication, recurrence of disease, length of stay in health care facilities or survival for a patient or group of patients. The simplistic meaning of prognosis is a prediction of the future course and outcome of a disease and an indication of the likelihood of recovery from that disease.

Computational prognostic model may be used, in accordance with the present technique to predict the natural course of disease, or the expected outcome after treatment. Prognosis forms an integral part of systems for treatment selection and treatment planning. Furthermore, prognostic models may play an important role in guiding diagnostic problem solving, e.g. by only requesting information concerning tests, of which the outcome affects knowledge of the prognosis.

In recent years several methods and techniques from the fields of artificial intelligence, decision theory and statistics have been introduced into models of the medical management of patients (diagnosis, treatment, follow-up); in some of these models, assessment of the expected prognosis constitutes an integral part. Typically, recent prognostic methods rely on explicit patho-physiological models, which may be combined with traditional models of life expectancy. Examples of such domain models are causal disease models, and physiological models of regulatory mechanisms in the human body. Such model-based approaches have the potential to facilitate the development of knowledge-based systems, because the medical domain models can be partially obtained from the medical literature.

Various methods have been suggested for the representations of such domain models ranging from quantitative and probabilistic approaches to symbolic and qualitative ones. Semantic concepts such as time, e.g. for modeling the progressive changes of regulatory mechanisms, have formed an important and challenging modeling issue. Moreover, automatic learning techniques of such models have been proposed. When model construction is hard, less explicit domain models have been studied such as the use of case-based representations and its combination with more explicit domain models.

Computer-Assisted Assessment (CAAx)

Computer-assisted assessment modules may include algorithms for analyzing a wide range of conditions or situations. By way of example, such algorithms may be employed to evaluate the outcome of a medical procedure (e.g., surgery), the outcome of therapy due to an injury (e.g. spinal injury), conditions (e.g. pregnancy), situations (e.g. trauma), processes (e.g. insurance, reimbursement, equipment utilization), and individuals (e.g. patients, students, medical professionals).

Figure 31:
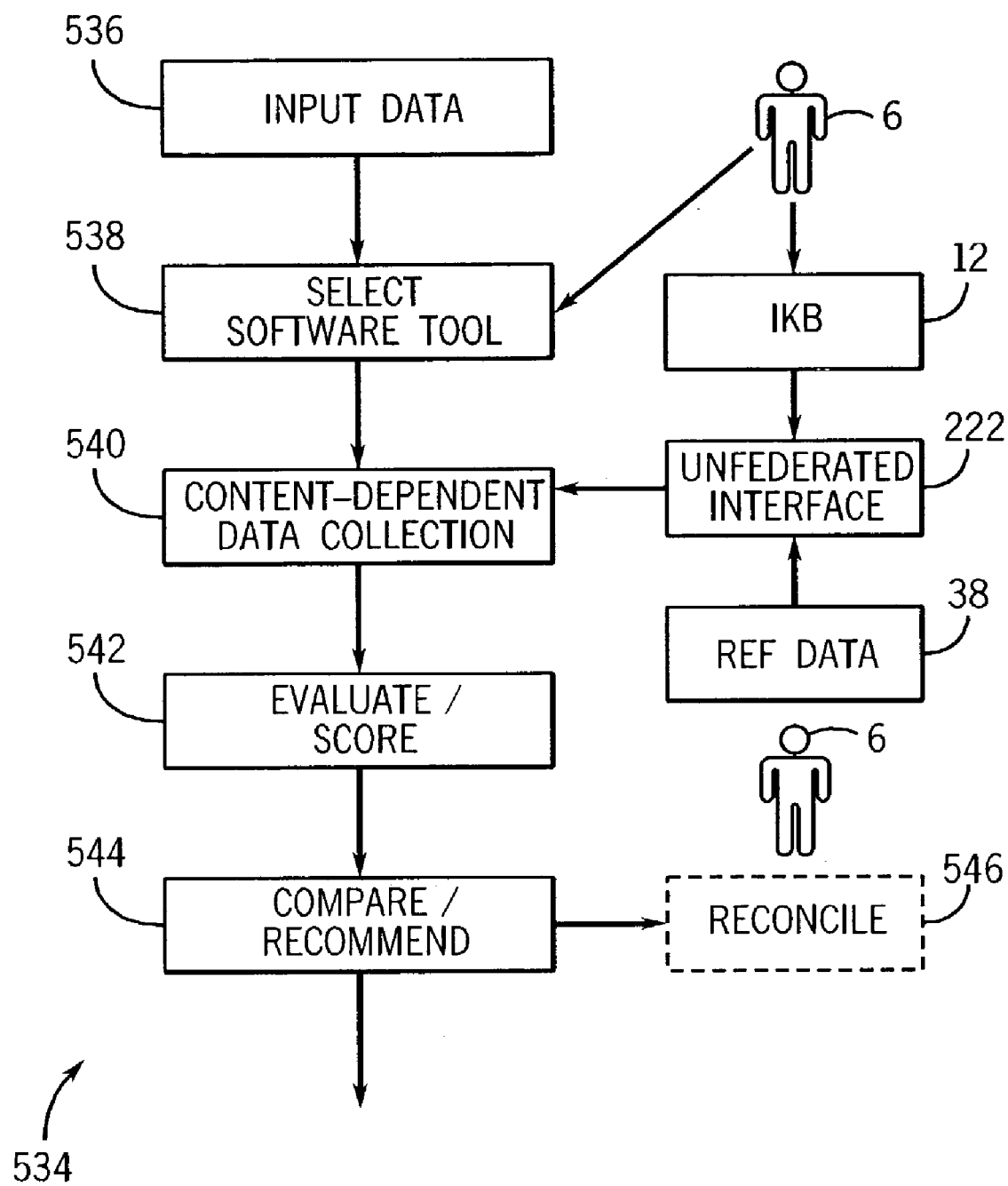
FIG. 31 is a diagrammatical representation of a computer-assisted assessment algorithm which may serve as one of the CAX algorithms implemented.

Certain exemplary steps in a CAAx algorithm are illustrated generally in FIG. 31. The algorithm 534 begins with input of key data at step 536. Depending upon the purpose of the algorithm, such data may include a designation or description of a situation, task, available results, intended person, requested information, and so forth. The data is used to identify a desired software tool, as indicated at step 538, which may take the form of a "wizard" used as an interface to lead a user through the assessment process. The interface may be at least partially based upon input from a professional or expert in the field of the operations executed by the algorithm or in the field of the data or assessment to be performed.

At step 540, more specific information may be evoked from one or more users, or automatically acquired or accessed from the various resources described above. Where the data is input by an individual, a customized interface may be provided in a manner described above, such as via the unfederated interface layer 222, drawing upon information from the integrated knowledge base 12 and data resources 18. As noted above, such interfaces may be customized for the particular user, the function performed, the data to be provided or accessed, and so forth.

Based upon the information provided, assessment is performed, as indicated at step 542. Such assessment will generally vary widely based upon the condition, situation, or other issue being evaluated. In a presently contemplated implementation, a score is determined from the assessment, and a comparison is performed based upon the score at step 544. The comparison is then the basis of a recommendation for further action, or may simply serve as the basis for reported results of the assessment. Moreover, results of the process may optionally be reconciled, where potential conflicts or judgments are in order, as indicated at step 546, including input from a human expert, where desired.

Business Model Implementation

The foregoing techniques permit implementation in a wide range of manners. For example, as noted repeatedly, the use of data and the interaction between data and modules may be implemented on a very small scale, including at a single workstation. Higher levels of integration may be provided by network links between various types of resources and workstations, and at various levels between network components as also described above. It should also be noted that the present techniques may be implemented as overall business models within an industry or a portion of an industry.

The business model implementation for the present techniques may include software installed on one or more memory devices or machine-readable media, such as disks, hard drives, flash memory, and so forth. A user may then employ the techniques individually, or by access to specific sites, links, services, databases, and so forth through a network. Similarly, a business model based upon the techniques may be developed such that the technique is offered on a pay-per-use, subscription, or any other suitable basis.

Such business models may be employed for any or all of the foregoing techniques, and may be offered on a "modular" basis. By way of example, institutions may subscribe or order services for evaluation of patient populations, scheduling of services and resources, development of models for prediction of patient conditions, training purposes, and so forth. Individuals or institutions may subscribe or purchase similar services for maintenance of individual patient records, integration of records, and the like. Certain of the techniques may be offered in conjunction with other assets or services, such as imaging systems, workstations, management networks, and so forth.

As will be appreciated by those skilled in the art, the business models built upon the foregoing techniques may employ a wide range of support software and hardware, including servers, drivers, translators, and so forth which permit or facilitate interaction with databases, processing resources, and the data and controllable and prescribable resources described above. Supporting components which provide for security, verification, interfacing and synchronization of data may be incorporated into such systems, or may be distributed among the systems and the various users or clients. Financial support modules, including modules which permit tracking and invoicing for services may be incorporated in a similar manner.

It is similarly contemplated that certain of the foregoing techniques may be implemented in sector-wide or industry-wide manners. Thus, high levels of integration may be enabled by appropriately standardizing or tagging data for access, exchange, uploading, downloading, translation, processing, and so forth.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for processing medical data comprising:
   accessing first image data from a repository;
   reconstructing and displaying a medical diagnostic image based upon the first image data;
   receiving data from a human image reader regarding a reader feature of interest in the displayed image;
   accessing second image data derived from an integrated knowledge base including data from a plurality of controllable and prescribable data resources;
   analyzing the first and second image data via a computer-assisted data operating algorithm to generate a result data set identifying a computer feature of interest in the image data;
   comparing the result data set to the data from the human image reader; and
   providing feedback to the human image reader based upon the analysis.

2. The method of claim 1, wherein the first image data is derived from data from a first imaging modality and the second image data is derived from data from a second imaging modality different from the first modality.

3. The method of claim 1, wherein the second image data includes data derived from image data for a population of patients exhibiting similar features of interest.

4. The method of claim 1, further comprising accessing and analyzing supplemental data including data selected from a group consisting of electrical resource data, imaging resource data, laboratory data, histologic data, financial data, and demographic data.

5. The method of claim 1, wherein the first and second image data is analyzed after the data is received from the human image reader.

6. The method of claim 1, wherein the computer-assisted data operating algorithm is a computer-assisted diagnosis algorithm.

7. The method of claim 1, wherein the computer-assisted data operating algorithm is a computer-assisted processing algorithm.

8. The method of claim 1, wherein the computer-assisted data operating algorithm is a computer-assisted acquisition algorithm.

9. The method of claim 1, wherein the feedback is based upon a difference between feature detection by the human image reader and feature detection performed by the algorithm.

10. The method of claim 1 wherein the feedback is based upon a difference between feature segmentation by the human image reader and feature segmentation performed by the algorithm.

11. The method of claim 1 wherein the feedback is based upon a difference between feature classification by the human image reader and feature classification performed by the algorithm.

12. A system for processing medical image data comprising:
a data repository for storing medical image data;
a display device for displaying a reconstructed image based upon the image data; and
a programmed computer system configured to access image data from the repository, to reconstruct a medical diagnostic image from based upon the image data, to display the image via the display device, to receive data from a human image reader regarding a reader feature of interest in the displayed image, to access supplemental data from an integrated knowledge base including clinical and non-clinical data from a plurality of controllable and prescribable data resources, to analyze the image data and the supplemental data via a computer-assisted data operating algorithm to generate a result data set, to compare the result data set to the data from the human image reader, and to provide feedback to the human image reader based upon the analysis.

13. The system of claim 12, wherein the image data is derived from data from a first imaging modality and the supplemental data is derived from data from a second imaging modality different from the first modality.

14. The system of claim 12, wherein the supplemental data includes data derived from image data for a population of patients exhibiting similar features of interest.

15. The system of claim 12, wherein the supplemental data includes data selected from a group consisting of electrical resource data, imaging resource data, laboratory data, histologic data, financial data, and demographic data.

16. The system of claim 12, wherein the image data is analyzed after the data is received from the human image reader.

17. The system of claim 12, wherein the computer-assisted data operating algorithm is a computer-assisted diagnosis algorithm.

18. The system of claim 12, wherein the computer-assisted data operating algorithm is a computer-assisted processing algorithm.

19. The system of claim 12, wherein the computer-assisted data operating algorithm is a computer-assisted acquisition algorithm.

20. The system of claim 12, wherein the feedback is based upon a difference between feature detection by the human image reader and feature detection performed by the algorithm.

21. The system of claim 12, wherein the feedback is based upon a difference between feature segmentation by the human image reader and feature segmentation performed by the algorithm.

22. The system of claim 12 wherein the feedback is based upon a difference between feature classification by the human image reader and feature classification performed by the algorithm.

23. The system of claim 12, further comprising a workstation at which the display device is located, and wherein the computer system is at least partially remote from the workstation.

24. A system for processing medical data comprising:
means for accessing first image data from a repository;
reconstructing and displaying a medical diagnostic image from based upon the first image data;
means for receiving data from a human image reader regarding a reader feature of interest in the displayed image;
means for accessing second image data derived from an integrated knowledge base including data from a plurality of controllable and prescribable data resources;
means for analyzing the first and second image data via a computer-assisted data operating algorithm to generate a result data set identifying a computer feature of interest in the image data;
means for comparing the result data set to the data from the human image reader; and
means for providing feedback to the human image reader based upon the analysis.

25. A computer executable program comprising:
at least one machine readable medium;
computer code stored on the at least one machine readable medium comprising instructions for accessing first image data from a repository, reconstructing and displaying a medical diagnostic image from based upon the first image data, receiving data from a human image reader regarding a reader feature of interest in the displayed image, accessing second image data derived from an integrated knowledge base including data from a plurality of controllable and prescribable data resources, analyzing the first and second image data via a computer-assisted data operating algorithm to generate a result data set identifying a computer feature of interest in the image data, comparing the result data set to the data from the human image reader, and providing feedback to the human image reader based upon the analysis.

* * * * *